United States Patent
Gestwicki et al.

(10) Patent No.: US 10,221,171 B2
(45) Date of Patent: Mar. 5, 2019

(54) OXATHIAZOLE THIAZOLIUM HSP 70 INHIBITORS

(71) Applicant: THE REGENTS OF THE UNIVERSITY OF CALIFORNIA, Oakland, CA (US)

(72) Inventors: Jason E. Gestwicki, Moss Beach, CA (US); Xiaokai Li, Ankeny, IA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/536,869

(22) PCT Filed: Jan. 11, 2016

(86) PCT No.: PCT/US2016/012900
§ 371 (c)(1),
(2) Date: Jun. 16, 2017

(87) PCT Pub. No.: WO2016/112394
PCT Pub. Date: Jul. 14, 2016

(65) Prior Publication Data
US 2018/0002325 A1    Jan. 4, 2018

Related U.S. Application Data

(60) Provisional application No. 62/101,749, filed on Jan. 9, 2015.

(51) Int. Cl.
C07D 417/14    (2006.01)
C07D 277/64    (2006.01)

(52) U.S. Cl.
CPC ......... *C07D 417/14* (2013.01); *C07D 277/64* (2013.01)

(58) Field of Classification Search
CPC .................................................... C07D 417/14
USPC ......................................................... 514/338
See application file for complete search history.

(56) References Cited

U.S. PATENT DOCUMENTS

| 5,360,803 A | 11/1994 | Shishido et al. |
| 2014/0275169 A1 | 9/2014 | Finley et al. |

FOREIGN PATENT DOCUMENTS

| WO | WO-96/03393 A1 | 2/1996 |
| WO | WO-2014/134243 A1 | 9/2014 |

OTHER PUBLICATIONS

International Search Report dated Jun. 2, 2016, for PCT Application No. PCT/US2016/012900, filed Jan. 11, 2016, 4 pages.
Written Opinion dated Jun. 2, 2016, for PCT Application No. PCT/US2016/012900, filed Jan. 11, 2016, 8 pages.
Wadhwa, R. et al. (Dec. 15, 2000). "Selective toxicity of MKT-077 to cancer cells is mediated by its binding to the hsp70 family protein mot-2 and reactivation of p53 function," *Cancer Res* 60(24):6818-6821.
Li, X. et al. (Nov. 14, 2013). "Analogs of the Allosteric Heat Shock Protein 70 (Hsp70) Inhibitor, MKT-077, as Anti-Cancer Agents," *ACS Med Chem Lett* 4(11):1042-1047.
Li, X. et al. (Mar. 2015, e-published Jan. 6, 2015). "Validation of the Hsp70-Bag3 protein-protein interaction as a potential therapeutic target in cancer," *Mol Cancer Ther* 14(3):642-648.
Extended European Search Report dated May 28, 2018, for EP Application No. 16735554.4, 8 pages.

*Primary Examiner* — Kahsay Habte
(74) *Attorney, Agent, or Firm* — Mintz

(57) ABSTRACT

Provided herein are compounds of formula (I) which are, inter alia, useful allosteric inhibitors of Hsp70. The compounds and methods provided are useful for the treatment of cancer, infectious and neurodegenerative diseases.

36 Claims, 6 Drawing Sheets

OXATHIAZOLE THIAZOLIUM HSP 70 INHIBITORS

CROSS-REFERENCES TO RELATED APPLICATIONS

This application claims benefit of U.S. Patent Application No. 62/101,749, filed on Jan. 9, 2015, which is hereby incorporated by reference in its entirety.

STATEMENT AS TO RIGHTS TO INVENTIONS MADE UNDER FEDERALLY SPONSORED RESEARCH AND DEVELOPMENT

This invention was made with government support under $R^{01}NS059690$ awarded by the National Institutes of Health. The Government has certain rights in the invention.

BACKGROUND OF THE INVENTION

Heat shock protein 70 (Hsp70) is a molecular chaperone that regulates protein homeostasis (proteostasis). It controls the balance of protein synthesis and folding degradation. Aberrant levels of Hsp70 activity are observed in diseases states, including cancer, bacterial and viral infection, neurodegeneration, and other diseases and disorders that involve cellular stress and protein misfolding. Therefore there is a need in the art for Hsp70 inhibitor compounds and their use to treat, inter alia, cancer, neurodegenerative and infectious diseases. The present invention addresses these and other problems in the art.

BRIEF SUMMARY OF THE INVENTION

In a first aspect, there is provided a compound with structure of formula (I):

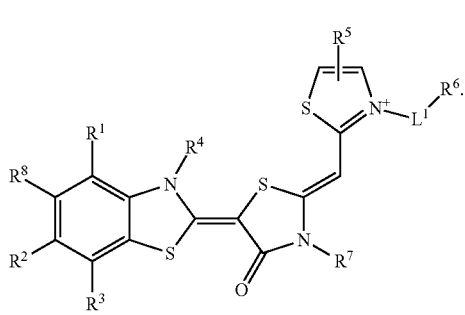

(I)

Regarding compound of formula (I), substituents $R^1$, $R^2$, $R^3$, $R^4$, $R^5$, $R^6$, $R^{6A}$, $R^7$, $R^8$ and $L^1$ are as disclosed herein. In embodiments, if $R^1$, $R^2$, and $R^3$ are independently hydrogen, —Cl, —F, —OCH$_3$, or —CF$_3$, then $R^6$ is not —CH$_2$pyridyl, -benzyl, —CH$_2$-difluorophenyl, —CH$_2$-cyclopropyl, —CH$_2$-4-(CH$_2$NHC(O)-tbutyl)phenyl, —CH$_2$-5-nitrofuranyl, —CH$_2$CH$_2$-5-nitrofuranyl, —CH$_2$-2-(5-CF$_3$)furanyl, —CH$_2$-fluorophenyl, —CH$_2$-chlorophenyl, —CH$_2$-nitrophenyl, —CH$_2$-cyanophenyl, —CH(CH$_3$)C(O)Ph, —CH$_2$-(methyl)phenyl, —CH$_2$-trifluoromethylphenyl, —CH$_2$-trifluoromethoxyphenyl, —CH$_2$-difluoromethoxyphenyl, —CH$_2$-3-(2-CO$_2$CH$_3$)thienyl, —CH$_2$-3-(2-bromo)thienyl, —CH$_2$-3-isoxazolyl, —CH$_2$-5-isoxazolyl, —CH$_2$-5-(3-phenyl)isoxazolyl, —CH$_2$-3-(2-bromo)pyridyl, —CH$_2$-3-thienyl, —CH$_2$-2-(5-CO$_2$CH$_2$CH$_3$)furanyl, —CH$_2$-4-(2-methyl)thiazolyl, —CH$_2$-2-(5-CO$_2$CH$_3$)furanyl, —CH$_2$-5-(3-methyl)isoxazolyl, or —CH$_2$—CH(CH$_3$)phenyl.

In another aspect, there is provided a compound with structure of formula (I):

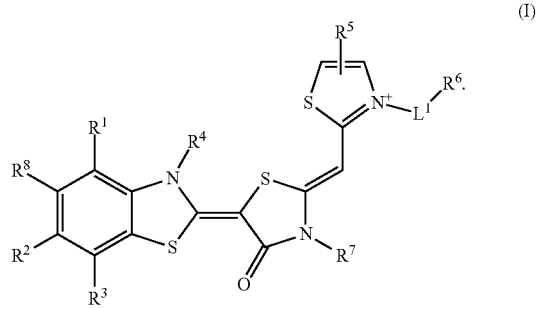

(I)

Regarding compound of formula (I), substituents $R^1$, $R^2$, $R^3$, $R^4$, $R^5$, $R^6$, $R^{6A}$, $R^7$, $R^8$ and $L^1$ are as disclosed herein. In embodiments, if $R^1$, $R^2$, and $R^3$ are independently hydrogen, —Cl, —F, —OCH$_3$, or —CF$_3$, then -$L^1$-$R^6$ is not —CH$_2$pyridyl, -benzyl, —CH$_2$-difluorophenyl, —CH$_2$-cyclopropyl, —CH$_2$-4-(CH$_2$NHC(O)-tbutyl)phenyl, —CH$_2$-5-nitrofuranyl, —CH$_2$CH$_2$-5-nitrofuranyl, —CH$_2$-2-(5-CF$_3$)furanyl, —CH$_2$-fluorophenyl, —CH$_2$-chlorophenyl, —CH$_2$-nitrophenyl, —CH$_2$-cyanophenyl, —CH(CH$_3$)C(O)Ph, —CH$_2$-(methyl)phenyl, —CH$_2$-trifluoromethylphenyl, —CH$_2$-trifluoromethoxyphenyl, —CH$_2$-difluoromethoxyphenyl, —CH$_2$-3-(2-CO$_2$CH$_3$)thienyl, —CH$_2$-3-(2-bromo)thienyl, —CH$_2$-3-isoxazolyl, —CH$_2$-5-isoxazolyl, —CH$_2$-5-(3-phenyl)isoxazolyl, —CH$_2$-3-(2-bromo)pyridyl, —CH$_2$-3-thienyl, —CH$_2$-2-(5-CO$_2$CH$_2$CH$_3$)furanyl, —CH$_2$-4-(2-methyl)thiazolyl, —CH$_2$-2-(5-CO$_2$CH$_3$)furanyl, —CH$_2$-5-(3-methyl)isoxazolyl, or —CH$_2$—CH(CH$_3$)phenyl.

In another aspect, there is provided a pharmaceutical composition including a pharmaceutically acceptable excipient and a compound of formula (I) as disclosed herein, and embodiments thereof.

In another aspect, there is provided a method of treating a Hsp70-mediated disease in a patient in need of such treatment. The method includes administering a therapeutically effective amount of a compound of formula (I) as disclosed herein, and embodiments thereof.

In another aspect, there is provided a method for inhibiting the activity of Hsp70 in a cell. The method includes contacting the cell with a compound of of formula (I) as disclosed herein.

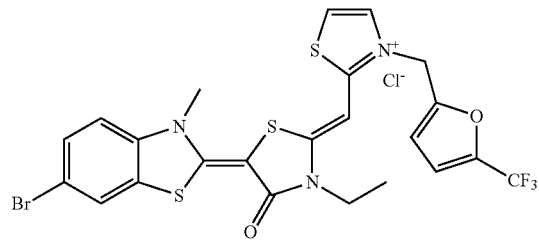 [SMILES: CCn1c(=O)/c(=C2\Sc3cc(Br)ccc3N2C)s/c1=C\c1scc[n+]1Cc1ccc(C(F)(F)F)o1 ; [Cl-]]

Figure 1:
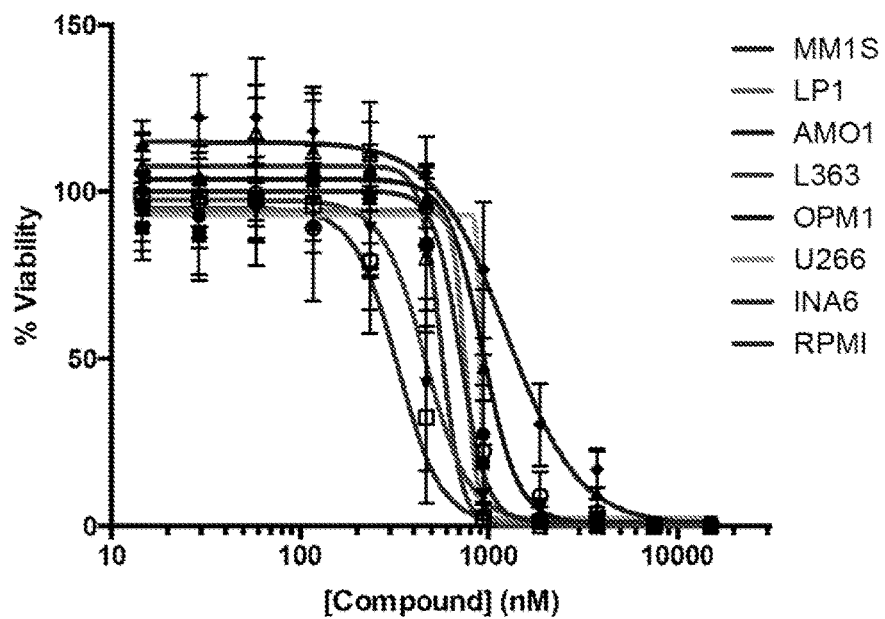
FIG. 1: JG-345 active against multiple myeloma cell lines. JG-345 has anti-proliferative activity against a multiple myeloma cell lines. Cell lines were treated with JG-345 and cell viability measured after 48 hrs by MTT assays. Results are shown as a percentage of a solvent control (1% DMSO). Results are the average of experiments performed in triplicate. Error bars represent SEM.
Figure 2:
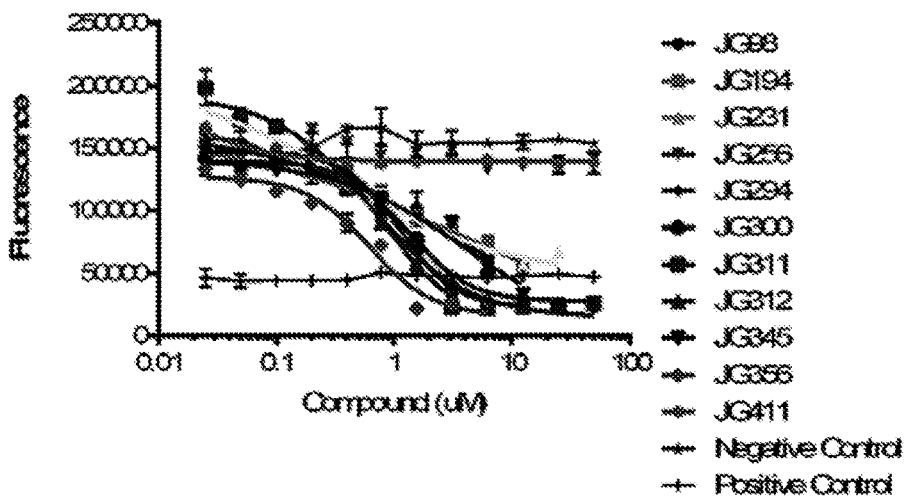
FIG. 2: All analogs retain activity against the Hsp70-Bag3 complex in vitro. Analogs retain the ability to inhibit the physical interaction between purified human Hsp70 and Bag3, as measured by flow cytometry protein interaction assays (FCPIAs). Hsp70 was immobilized on beads and binding to fluorescently labeled Bag3 was measured, using a method reported in Rauch and Gestwicki 2014 J. Biol. Chem. 289:1402. Results are the average of independent triplicates. Error bars represent SEM.
Figure 3:
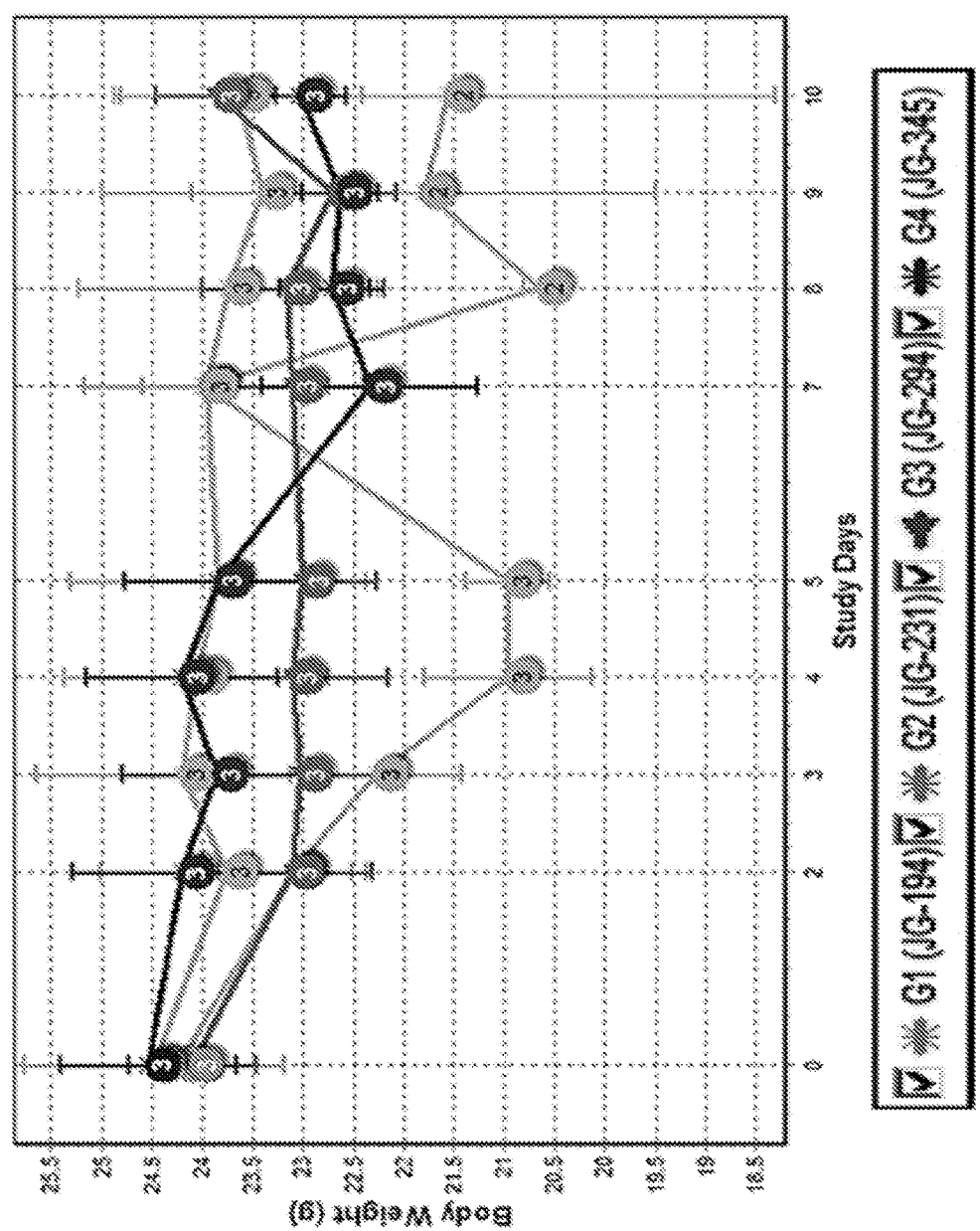
FIG. 3: Compounds JG231, 294 and 345 are tolerated in mice, based on weight. Compounds JG-294 and JG-345 are tolerated in mice. Analogs were delivered daily to male CD1 mice by i.p. at 5 mg/kg/day. Five mice per group. Error bars represent SEM.
Figure 4A:
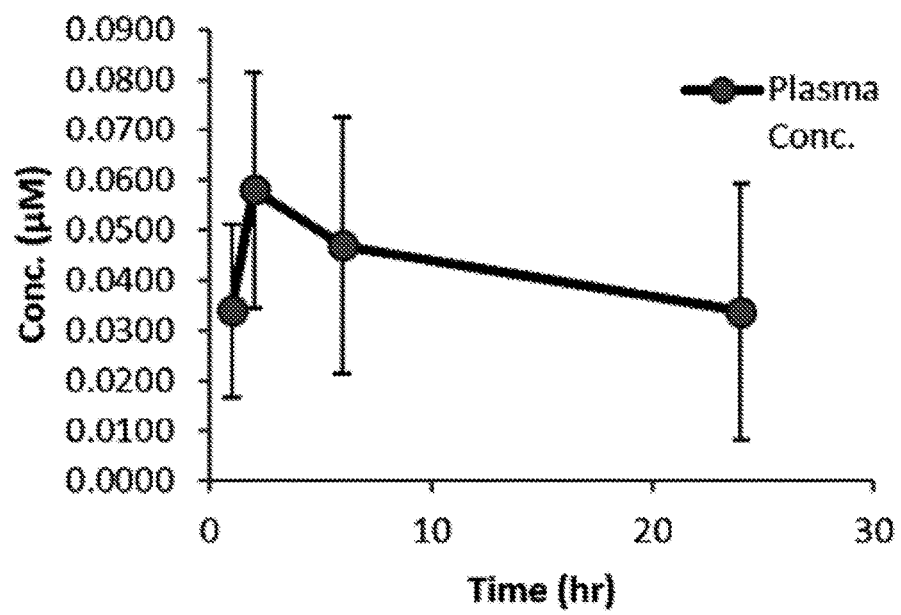
FIG. 4A-4B: Pharmacokinetics of JG-294 (FIG. 4A) having the structure
Figure 4B:
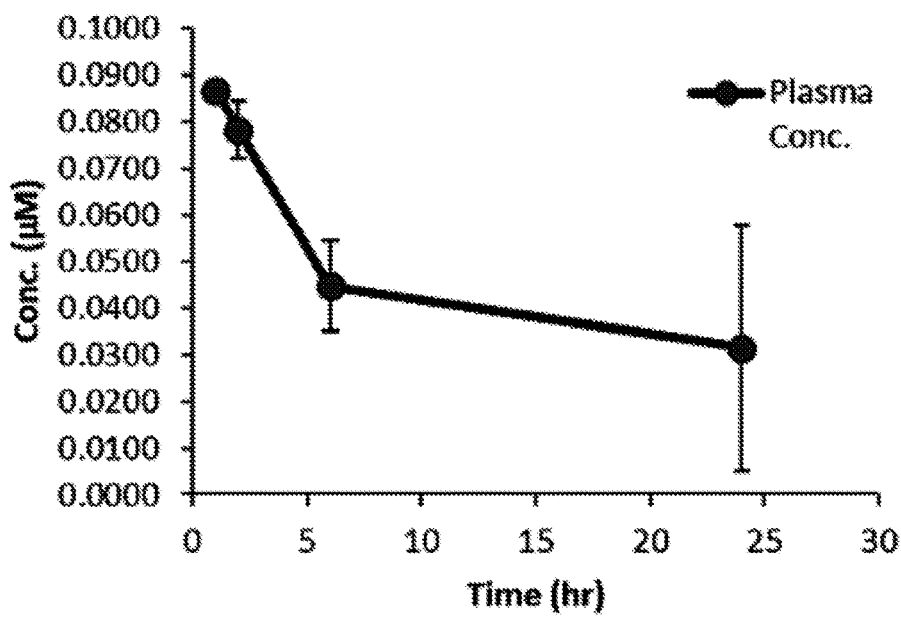

and JG-345 (FIG. 4B) having the structure

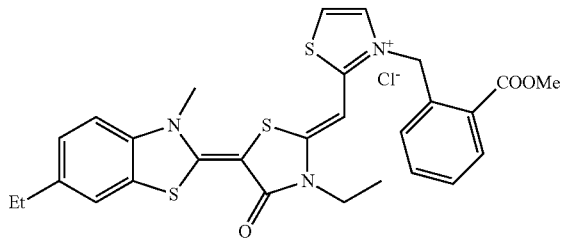 [SMILES: CCc1ccc2c(c1)S/C(=c1/s/c(=C\c3scc[n+]3Cc3ccccc3C(=O)OC)n(CC)c1=O)N2C ; [Cl-]]

A single injection of compound was delivered to CD1 mice by i.p. and the plasma collected at the indicated times. Compound levels were calculated by HPLC, using a standard curve. See also results depicted in Table 3A and 3B.

Figure 5A:
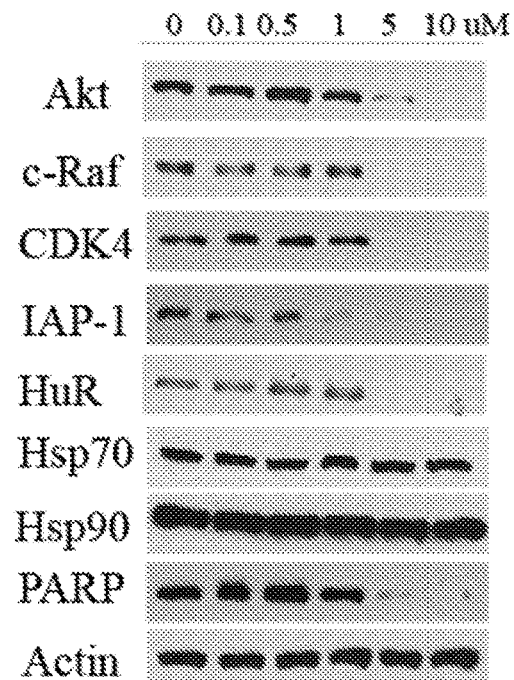
Figure 5B:
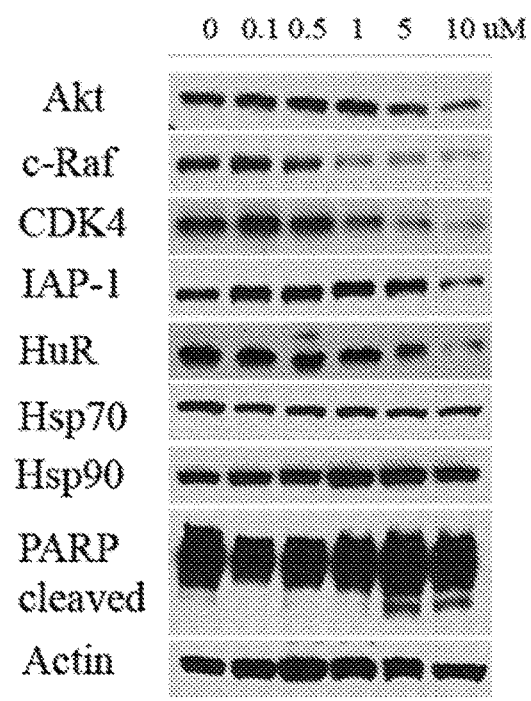
Figure 5C:
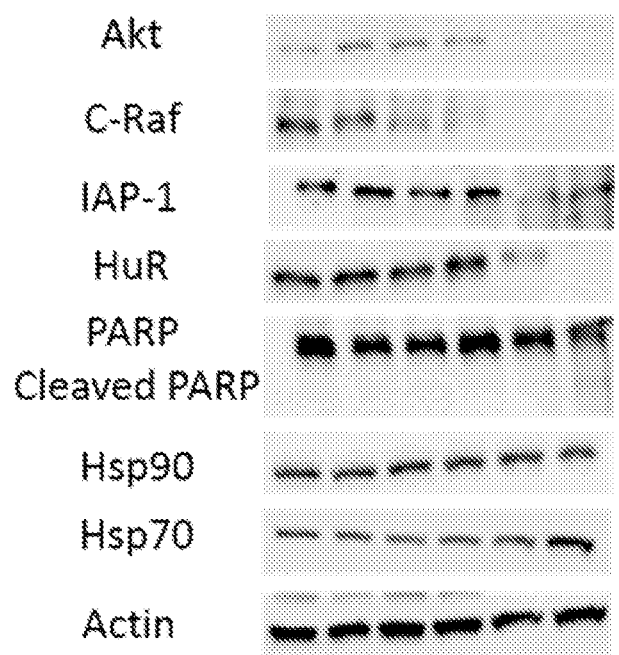

FIG. 5A-5C: JG-345 retains the ability to destabilize Hsp70 clients in MCF7 cells. Cells were treated for 24 hrs with compound, lysed and Western blots performed. Like earlier analogs, such as JG-194 (FIG. 5A) and JG-231 (FIG. 5B), JG-345 (FIG. 5C) could destabilize c-Raf and other clients.

Figure 6:
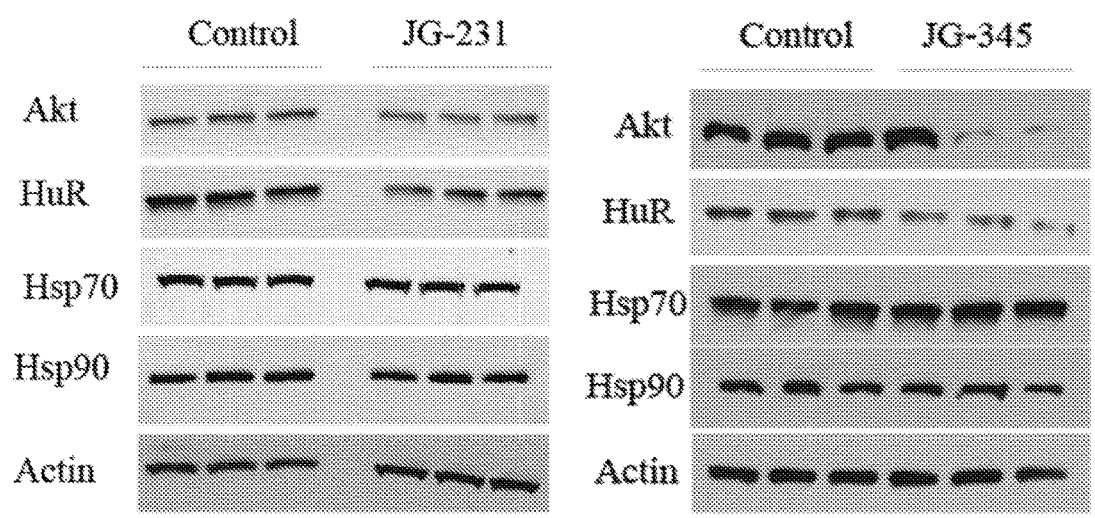

FIG. 6: JG-345 (right panel) destabilized Hsp70 clients in vivo. Xenografts of MCF7 cells were treated by delivery of compound in saline 5 mg/kg/day dosed for three days, after which tumors were harvested for western blot. Results from three separate animals are shown.

DETAILED DESCRIPTION OF THE INVENTION

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom (e.g. selected from the group consisting of O, N, P, Si, and S, and wherein the nitrogen and sulfur atoms may optionally be oxidized, and the nitrogen heteroatom may optionally be quaternized). The heteroatom(s) O, N, P, S, and Si may be placed at any interior position o-NHC(O)R$^9$, f the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$N(R)('R"—NRSO$_2$R'), —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", NR"C(O)$_2$R', NRC(NR'R')=NR'", S(O)R', —S(O)$_2$R', —S(O)$_2$N(R')(R", —NRSO$_2$R'), —CN, —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where variables s and d are independently integers of from 0 to 3, and X is —O—, —NR'—, —S—, —S(O)—, —S(O)$_2$—, or —S(O)$_2$NR'—. The substituents R, R', R", and R' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, NHNH$_2$, ONH$_2$, NHC=(O)NHNH$_2$, NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

In embodiments, a compound as described herein may include multiple instances of $R^2$ and/or other variables. In such embodiments, each variable may optional be different and be appropriately labeled to distinguish each group for greater clarity. For example, where each $R^2$ is different, they may be referred to, for example, as $R^{2.1}$, $R^{2.2}$, $R^{2.3}$, and/or $R^{2.4}$ respectively, wherein the definition of $R^2$ is assumed by $R^{2.1}$, $R^{2.2}$, $R^{2.3}$, and/or $R^{2.4}$. The variables used within a definition of $R^2$ and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

Where a moiety is substituted with an R substituent, the group may be referred to as "R-substituted." Where a moiety is R-substituted, the moiety is substituted with at least one R substituent and each R substituent is optionally different. For example, where a moiety herein is $R^{6A}$-substituted or unsubstituted alkyl, a plurality of $R^{6A}$ substituents may be attached to the alkyl moiety wherein each $R^{6A}$ substituent is optionally different. Where an R-substituted moiety is substituted with a plurality R substituents, each of the R-substituents may be differentiated herein using a prime symbol (') such as R', R'', etc. For example, where a moiety is $R^{6A}$-substituted or unsubstituted alkyl, and the moiety is substituted with a plurality of $R^{6A}$ substituents, the plurality of $R^{6A}$ substituents may be differentiated as $R^{6A'}$, $R^{6A''}$, $R^{6A'''}$, etc. In embodiments, the plurality of R substituents is 3. In embodiments, the plurality of R substituents is 2.

In embodiments, a compound as described herein may include multiple instances of $R^1$, $R^2$, $R^3$, $R^4$, $R^5$, $R^6$, $R^7$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and/or other variables. In such embodiments, each variable may optional be different and be appropriately labeled to distinguish each group for greater clarity. For example, where each $R^1$, $R^2$, $R^3$, $R^4$, R, $R^6$, $R^7$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and/or $R^{22}$ is different, they may be referred to, for example, as $R^{1.1}$, $R^{1.2}$, $R^{1.3}$, $R^{1.4}$, $R^{2.1}$, $R^{2.2}$, $R^{2.3}$, $R^{2.4}$, $R^{3.1}$, $R^{3.2}$, $R^{3.3}$, $R^{3.4}$, $R^{4.1}$, $R^{4.2}$, $R^{4.3}$, $R^{4.4}$, $R^{5.1}$, $R^{5.2}$, $R^{5.3}$, $R^{5.4}$, $R^{6.1}$, $R^{6.2}$, $R^{6.3}$, $R^{6.4}$, $R^{7.1}$, $R^{7.2}$, $R^{7.3}$, $R^{7.4}$, $R^{8.1}$, $R^{8.2}$, $R^{8.3}$, $R^{8.4}$, $R^{9.1}$, $R^{9.2}$, $R^{9.3}$, $R^{9.4}$, $R^{1.1}$, $R^{1.2}$, $R^{1.3}$, $R^{1.4}$, $R^{11.1}$, $R^{11.2}$, $R^{11.3}$, $R^{11.4}$, $R^{12.1}$, $R^{12.2}$, $R^{12.3}$, $R^{12.4}$, $R^{13.1}$, $R^{13.2}$, $R^{13.3}$, $R^{13.4}$, $R^{14.1}$, $R^{14.2}$, $R^{14.3}$, $R^{14.4}$, $R^{15.1}$, $R^{15.2}$, $R^{15.3}$, $R^{15.4}$, $R^{16.1}$, $R^{16.2}$, $R^{16.3}$, $R^{16.4}$, $R^{17.1}$, $R^{17.2}$, $R^{17.3}$, $R^{17.4}$, $R^{18.1}$, $R^{18.2}$, $R^{18.3}$, $R^{18.4}$, $R^{19.1}$, $R^{19.2}$, $R^{19.3}$, $R^{19.4}$, $R^{20.1}$, $R^{20.2}$, $R^{20.3}$, $R^{20.4}$, $R^{21.1}$, $R^{21.2}$, $R^{21.3}$, $R^{21.4}$, $R^{22.1}$, $R^{22.2}$, $R^{22.3}$, and/or $R^{22.4}$, respectively, wherein the definition of $R^1$ is assumed by $R^{1.1}$, $R^{1.2}$, $R^{1.3}$, and/or $R^{1.4}$, the definition of $R^2$ is assumed by $R^{2.1}$, $R^{2.2}$, $R^{2.3}$, and/or $R^{2.4}$, the definition of $R^3$ is assumed by $R^{3.1}$, $R^{3.2}$, $R^{33}$, and/or $R^{3.4}$, the definition of $R^4$ is assumed by $R^{4.1}$, $R^{4.2}$, $R^{4.3}$, and/or $R^{4.4}$, the definition of $R^5$ is assumed by $R^{5.1}$, $R^{5.2}$, $R^{5.3}$, and/or $R^{5.4}$, the definition of $R^6$ is assumed by $R^{6.1}$, $R^{6.2}$, $R^{6.3}$, and/or $R^{6.4}$, the definition of $R^7$ is assumed by $R^{7.1}$, $R^{7.2}$, $R^{7.3}$, and/or $R^{7.4}$, the definition of $R^8$ is assumed by $R^8$, $R^{8.2}$, $R^{8.3}$, and/or $R^{8.4}$, the definition of $R^9$ is assumed by $R^{9.1}$, $R^{9.2}$, $R^{9.3}$, and/or $R^{9.4}$, the definition of $R^{10}$ is assumed by $R^{1.1}$, $R^{10.2}$, $R^{10.3}$, and/or $R^{10.4}$, the definition of $R^{11}$ is assumed by $R^{11.11}$, $R^{11.2}$, $R^{11.3}$, and/or $R^{11.4}$, the definition of $R^{12}$ is assumed by $R^{12.1}$, $R^{12.2}$, $R^{12.3}$, and/or $R^{12.4}$, the definition of $R^{13}$ is assumed by $R^{13.1}$, $R^{13.2}$, $R^{13.3}$, and/or $R^{13.4}$, the definition of $R^{14}$ is assumed by $R^{14.1}$, $R^{14.2}$, $R^{14.3}$, and/or $R^{14.4}$, the definition of $R^{15}$ is assumed by $R^{15.1}$, $R^{15.2}$, $R^{15.3}$, and/or $R^{15.4}$, the definition of $R^{16}$ is assumed by $R^{16.1}$, $R^{16.2}$, $R^{16.3}$, and/or $R^{16.4}$, the definition of $R^{17}$ is assumed by $R^{17.1}$, $R^{17.2}$, $R^{17.3}$, and/or $R^{17.4}$, the definition of $R^{18}$ is assumed by $R^{18.1}$, $R^{18.2}$, $R^{18.3}$, and/or $R^{18.4}$ the definition of $R^{19}$ is assumed by $R^{19.1}$, $R^{19.2}$, $R^{19.3}$, and/or $R^{19.4}$, the definition of $R^{20}$ is assumed by $R^{20.1}$, $R^{20.2}$, $R^{20.3}$, and/or $R^{20.4}$, the definition of $R^{21}$ is assumed by $R^{21.1}$, $R^{21.2}$, $R^{21.3}$, and/or $R^{21.4}$, and the definition of $R^{22}$ is assumed by $R^{22.1}$, $R^{22.2}$, $R^{22.3}$, and/or $R^{22.4}$. The variables used within a definition of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and/or other variables that appear at multiple instances and are different may similarly be appropriately labeled to distinguish each group for greater clarity.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. infectious disease, hyperproliferative disease, cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with infection may be treated with an agent (e.g. compound as described herein) effective as an antibiotic.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease results from an infection.

As used herein, the term "infectious disease" refers to a disease or condition related to the presence of an organism (the agent or infectious agent) within or contacting the subject or patient. Examples include a bacterium, fungus, virus, or other microorganism. A "bacterial infectious disease" is an infectious disease wherein the organism is a bacterium.

In some embodiments, the disease is a disease having the symptom of cell hyperproliferation. In some embodiments, the disease is a disease having the symptom of an aberrant level of androgen receptor activity. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is prostate cancer. In embodiments, the disease is hormone sensitive prostate cancer. In embodiments, the disease is hormone refractory (insensitive) prostate cancer.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the infection causing agent resulting in endocytosis. By using liposomes, particularly where the liposome surface carries receptor ligands specific for target cells, or are otherwise preferentially directed to a specific target, one can focus the delivery of the compositions of the present invention into the target cells in vivo. The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of infection). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

Compositions

In a first aspect, there is provided a compound of formula (I),

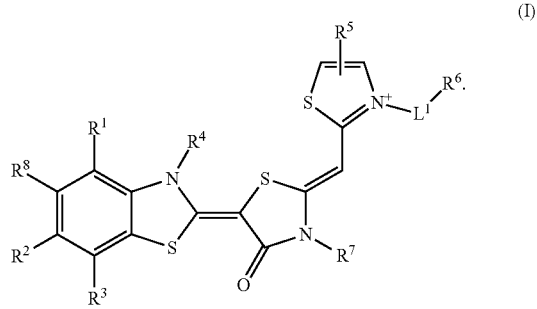

(I)

Regarding the compound of formula (I), $R^1$ is hydrogen, halogen, $-CX^a_3$, $-CN$, $-SR^9$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-NHC(O)R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is hydrogen, halogen, $-CX^a_3$, $-CN$, $-SR^9$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-NHC(O)R^9$, $-C(O)R^9$, $-C(O)-OR^9$, $-C(O)NR^9R^{10}$, or $-OR^9$. In embodiments, $R^1$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^1$ is $R^{1A}$-substituted (e.g., $C_1$-$C_{20}$ or $C_1$-$C_6$) alkyl, $R^{1A}$-substituted (e.g., 2 to 20 membered or 2 to 6 membered) heteroalkyl, $R^{1A}$-substituted (e.g., $C_3$-$C_8$ or $C_5$-$C_7$) cycloalkyl, $R^{1A}$-substituted (e.g., 3 to 8 membered or 3 to 6 membered) heterocycloalkyl, $R^{1A}$-substituted (e.g., $C_5$-$C_{10}$ or $C_5$-$C_6$) aryl, or $R^{1A}$-substituted (e.g., 5 to 10 membered or 5 to 6 membered) heteroaryl. $R^{1A}$ may be independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$R^2$ is hydrogen, halogen, $-CX^b_3$, $-CN$, $-SR^{11}$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-NHC(O)R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is hydrogen, halogen, $-CX^b_3$, $-CN$, $-SR^{11}$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $NR^{11}R^{12}$, $-NH-O-R^{11}$, $-NHC(O)R^{11}$, $-C(O)R^{11}$, $-C(O)-OR^{11}$, $-C(O)NR^{11}R^{12}$ or $-OR^{11}$. In embodiments, $R^2$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^2$ is $R^{2A}$-substituted (e.g., $C_1$-$C_{20}$ or $C_1$-$C_6$) alkyl, $R^{2A}$-substituted (e.g., 2 to 20 membered or 2 to 6 membered) heteroalkyl, $R^{2A}$-substituted (e.g., $C_3$-$C_8$ or $C_5$-$C_7$) cycloalkyl, $R^{2A}$-substituted (e.g., 3 to 8 membered or 3 to 6 membered) heterocycloalkyl, $R^{2A}$-substituted (e.g., $C_5$-$C_{10}$ or $C_5$-$C_6$) aryl, or $R^{2A}$-substituted (e.g., 5 to 10 membered or 5 to 6 membered) heteroaryl. $R^{2A}$ may be independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, unsubstituted (e.g., $C_1$-$C_{20}$ or $C_1$-$C_6$) alkyl, unsubstituted (e.g., 2 to membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$R^3$ is hydrogen, halogen, —$CX^c_3$, —CN, —$SR^{13}$, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —NHC(O)$R^{13}$, —C(O)$R^{13}$, —C(O)—OR, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is hydrogen, halogen, —$CX^c_3$, —CN, —$SR^{13}$, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —NHC(O)$R^{13}$, —C(O)$R^{13}$, —C(O)—$OR^{13}$, —C(O)$NR^{13}R^{14}$ or —$OR^{13}$. In embodiments, $R^3$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^3$ is $R^{3A}$-substituted (e.g., $C_1$-$C_{20}$ or $C_1$-$C_6$) alkyl, $R^{3A}$-substituted (e.g., 2 to 20 membered or 2 to 6 membered) heteroalkyl, $R^{3A}$-substituted (e.g., $C_3$-$C_8$ or $C_5$-$C_7$) cycloalkyl, $R^{3A}$-substituted (e.g., 3 to 8 membered or 3 to 6 membered) heterocycloalkyl, $R^{3A}$-substituted (e.g., $C_5$-$C_{10}$ or $C_5$-$C_6$) aryl, or $R^{3A}$-substituted (e.g., 5 to 10 membered or 5 to 6 membered) heteroaryl. $R^{3A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$R^8$ is hydrogen, halogen, —$CX^d_3$, —CN, —$SR^{15}$, —$SO_2Cl$, —$SO_{n4}R^{15}$, —$SO_{v4}NR^{15}R^{16}$, —$NHNH_2$, —$ONR^{15}R^{16}$, —NHC=(O)$NHNH_2$, —NHC=(O)$NR^{15}R^{16}$, —$N(O)_{m4}$, —$NR^{15}R^{16}$, —NH—O—$R^{15}$, —NHC(O)$R^{15}$, —C(O)$R^{15}$, —C(O)—OR, —C(O)$NR^{15}R^{16}$, —$OR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^8$ is hydrogen, halogen, —$CX^d_3$, —CN, —$SR^{15}$, —$SO_2Cl$, —$SO_{n4}R^{15}$, —$SO_{v4}NR^{15}R^{16}$, —$NHNH_2$, —$ONR^{15}R^{16}$, —NHC=(O)$NHNH_2$, —NHC=(O)$NR^{15}R^{16}$, —$N(O)_{m4}$, —$NR^{15}R^{16}$, —NH—O—$R^{15}$, —NHC(O)$R^{15}$, —C(O)$R^{15}$, —C(O)—$OR^{15}$, —C(O)$NR^{15}R^{16}$ or —$OR^{15}$. In embodiments, $R^8$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^8$ is $R^{8A}$-substituted (e.g., $C_1$-$C_{20}$ or $C_1$-$C_6$) alkyl, $R^{8A}$-substituted (e.g., 2 to 20 membered or 2 to 6 membered) heteroalkyl, $R^{8A}$-substituted (e.g., $C_3$-$C_8$ or $C_5$-$C_7$) cycloalkyl, $R^{8A}$-substituted (e.g., 3 to 8 membered or 3 to 6 membered) heterocycloalkyl, $R^{8A}$-substituted (e.g., $C_5$-$C_{10}$ or $C_5$-$C_6$) aryl, or $R^{8A}$-substituted (e.g., 5 to 10 membered or 5 to 6 membered) heteroaryl. $R^{8A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$R^4$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^4$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^4$ is $R^{4A}$-substituted (e.g., $C_1$-$C_{20}$ or $C_1$-$C_6$) alkyl, $R^{4A}$-substituted (e.g., 2 to 20 membered or 2 to 6 membered) heteroalkyl, $R^{4A}$-substituted (e.g., $C_3$-$C_8$ or $C_5$-$C_7$) cycloalkyl, $R^{4A}$-substituted (e.g., 3 to 8 membered or 3 to 6 membered) heterocycloalkyl, $R^{4A}$-substituted (e.g., $C_5$-$C_{10}$ or $C_5$-$C_6$) aryl, or $R^{4A}$-substituted (e.g., 5 to 10 membered or 5 to 6 membered) heteroaryl. $R^{4A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$R^5$ is hydrogen, halogen, —$CX^e_3$, —CN, —$SR^{17}$, —$SO_2Cl$, —$SO_{n5}R^{17}$, —$SO_{v5}NR^{17}R^{18}$, —$NHNH_2$, —$ONR^{17}R^{18}$, —NHC=(O)$NHNH_2$, —NHC=(O)$NR^{17}R^{18}$, —$N(O)_{m5}$, —$NR^{17}R^{18}$, —NH—O—$R^{17}$, —NHC(O)$R^{17}$, —C(O)$R^{17}$, —C(O)—$OR^{17}$, —C(O)$NR^{17}R^{18}$, —$OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^5$ is hydrogen, halogen, —$CX^e_3$, —CN, —$SR^{17}$, —$SO_2Cl$, —$SO_{n5}R^{17}$, —$SO_{v5}NR^{17}R^{18}$, —$NHNH_2$, —$ONR^{17}R^{18}$, —NHC=(O)$NHNH_2$, —NHC=(O)$NR^{17}R^{18}$, —$N(O)_{m5}$, —$NR^{17}R^{18}$, —NH—O—$R^{17}$, —NHC(O)$R^{17}$, —C(O)$R^{17}$, —C(O)—$OR^{17}$, —C(O)$NR^{17}R^{18}$ or —$OR^{17}$. In embodiments, $R^5$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^5$ is $R^{5A}$-substituted (e.g., $C_1$-$C_{20}$ or $C_1$-$C_6$) alkyl, $R^{5A}$-substituted (e.g., 2 to 20 membered or 2 to 6 membered)

heteroalkyl, $R^{5A}$-substituted (e.g., $C_3$-$C_8$ or $C_5$-$C_7$) cycloalkyl, $R^{5A}$-substituted (e.g., 3 to 8 membered or 3 to 6 membered) heterocycloalkyl, $R^{5A}$-substituted (e.g., $C_5$-$C_{10}$ or $C_5$-$C_6$) aryl, or $R^{5A}$-substituted (e.g., 5 to 10 membered or 5 to 6 membered) heteroaryl. $R^{5A}$ may be independently hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$R^6$ is $R^{6A}$-substituted cycloalkyl, $R^{6A}$-substituted heterocycloalkyl, $R^{6A}$-substituted aryl or $R^{6A}$-substituted heteroaryl. $R^{6A}$ is halogen, —$CX^f_3$, —CN, —$SR^{19}$, —$SO_2Cl$, —$SO_{n6}R^{19}$, —$SO_{v6}NR^{19}R^{20}$, —$NHNH_2$, —$ONR^{19}R^2$, —NHC=(O)$NHNH_2$, —NHC=(O)$NR^{19}R^{20}$, —N(O)$_{m6}$, —$NR^{19}R^{20}$, —NH—O—$R^{19}$, —NHC(O)$R^{19}$, —C(O)$R^{19}$, —C(O)—$OR^{19}$, —C(O)$NR^{19}R^{20}$, —$OR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{6A}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{6A}$ is $R^{6B}$-substituted (e.g., $C_1$-$C_{20}$ or $C_1$-$C_6$) alkyl, $R^{6B}$-substituted (e.g., 2 to 20 membered or 2 to 6 membered) heteroalkyl, $R^{6B}$-substituted (e.g., $C_3$-$C_8$ or $C_5$-$C_7$) cycloalkyl, $R^{6B}$-substituted (e.g., 3 to 8 membered or 3 to 6 membered) heterocycloalkyl, $R^{6B}$-substituted (e.g., $C_5$-$C_{10}$ or $C_5$-$C_6$) aryl, or $R^{6B}$-substituted (e.g., 5 to 10 membered or 5 to 6 membered) heteroaryl. $R^{6B}$ may be independently hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$R^7$ is hydrogen, halogen, —$CX^g_3$, —CN, —$SR^{21}$, —$SO_2Cl$, —$SO_nR^{21}$, —$SO_{v7}NR^{21}R^{22}$, —$NHNH_2$, —$ONR^{21}R^{22}$, —NHC=(O)$NHNH_2$, —NHC=(O)$NR^{21R2}$, —N(O)$_{m7}$, —$NR^{21}R^{22}$, —NH—O—$R^{21}$, —NHC(O)$R^{21}$, —C(O)$R^{21}$, —C(O)—$OR^{21}$, —C(O)$NR^{21}R^{22}$, —$OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^7$ is hydrogen, halogen, —$CX^g_3$, —CN, —$SR^{21}$, —$SO_2Cl$, —$SO_{n7}R^{21}$, —$SO_{v7}NR^{21}R^{22}$, —$NHNH_2$, —$ONR^{21}R^{22}$, —NHC=(O)$NHNH_2$, —NHC=(O)$NR^{21}R^{22}$, —N(O)$_{m7}$, —$NR^{21}R^{22}$, —NH—O—$R^{21}$, —NHC(O)$R^{21}$, —C(O)$R^{21}$, —C(O)—$OR^{21}$, —C(O)$NR^{21}R^{22}$ or —$OR^{21}$. In embodiments, $R^7$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^7$ is $R^{7A}$-substituted (e.g., $C_1$-$C_{20}$ or $C_1$-$C_6$) alkyl, $R^{7A}$-substituted (e.g., 2 to 20 membered or 2 to 6 membered) heteroalkyl, $R^{7A}$-substituted (e.g., $C_3$-$C_8$ or $C_5$-$C_7$) cycloalkyl, $R^{7A}$-substituted (e.g., 3 to 8 membered or 3 to 6 membered) heterocycloalkyl, $R^{7A}$-substituted (e.g., $C_5$-$C_{10}$ or $C_5$-$C_6$) aryl, or $R^{7A}$-substituted (e.g., 5 to 10 membered or 5 to 6 membered) heteroaryl. $R^{7A}$ may be independently hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$L^1$ is a bond, —S(O)—, —$S(O)_2$NH—, —NHS(O)$_2$—, —C(O)O—, —OC(O)—, —C(O)—, —C(O)NH—, —NH—, —NHC(O)—, —O—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is unsubstituted (e.g., $C_1$-$C_{20}$ or $C_1$-$C_6$) alkylene, unsubstituted (e.g., 2 to 20 membered or 2 to 6 membered) heteroalkylene, unsubstituted (e.g., $C_3$-$C_8$ or $C_5$-$C_7$) cycloalkylene, unsubstituted (e.g., 3 to 8 membered or 3 to 6 membered) heterocycloalkylene, unsubstituted (e.g., $C_5$-$C_{10}$ or $C_5$-$C_6$) arylene, or unsubstituted (e.g., 5 to 10 membered or 5 to 6 membered) heteroarylene. In embodiments, $L^1$ is $R^{L1}$-substituted (e.g., $C_1$-$C_{20}$ or $C_1$-$C_6$) alkylene, $R^{L1}$-substituted (e.g., 2 to 20 membered or 2 to 6 membered) heteroalkylene, $R^{L1}$-substituted (e.g., $C_3$-$C_8$ or $C_5$-$C_7$) cycloalkylene, $R^{L1}$-substituted (e.g., 3 to 8 membered or 3 to 6 membered) heterocycloalkylene, $R^{L1}$-substituted (e.g., $C_5$-$C_{10}$ or $C_5$-$C_6$) arylene, or $R^{L1}$-substituted (e.g., 5 to 10 membered or 5 to 6 membered) heteroarylene. $R^{L1}$ may be independently hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$R^9$, $R^{10}$, $R^{11}$, $R^{12}$, $R^{13}$, $R^{14}$, $R^5$, $R^{16}$, $R^{17}$, $R^{18}$, $R^{19}$, $R^{20}$, $R^{21}$, and $R^{22}$, are independently hydrogen, halogen, =O, =S, —$CF_3$, —CN, —$CCl_3$, —COOH, —$CH_2$COOH, —$COCH_3$, —$CONH_2$, —OH, —OC(O)$CH_3$, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^9$ is hydrogen, halogen, =O, =S, —$CF_3$, —CN, —$CCl_3$, —COOH, —$CH_2$COOH, —$COCH_3$, —$CONH_2$, —OH, —OC(O)$CH_3$, —SH, —$SO_2Cl$, —$SO_3H$, —$SO_4H$, —$SO_2NH_2$, —$NO_2$, —$NH_2$, —NHNH$_2$, —ONH$_2$ or —NHC=(O)NHNH$_2$. In embodiments, R$^9$ is unsubstituted (e.g., C$_1$-C$_{20}$ or C$_1$-C$_6$) alkyl, unsubstituted (e.g., 2 to 20 membered or 2 to 6 membered) heteroalkyl, unsubstituted (e.g., C$_3$-C$_8$ or C$_5$-C$_7$) cycloalkyl, unsubstituted (e.g., 3 to 8 membered or 3 to 6 membered) heterocycloalkyl, unsubstituted (e.g., C$_5$-C$_{10}$ or C$_5$-C$_6$) aryl, or unsubstituted (e.g., 5 to 10 membered or 5 to 6 membered) heteroaryl. In embodiments, R$^9$ is R$^{9A}$-substituted (e.g., C$_1$-C$_{20}$ or C$_1$-C$_6$) alkyl, R$^{9A}$-substituted (e.g., 2 to 20 membered or 2 to 6 membered) heteroalkyl, R$^{9A}$-substituted (e.g., C$_3$-C$_8$ or C$_5$-C$_7$) cycloalkyl, R$^{9A}$-substituted (e.g., 3 to 8 membered or 3 to 6 membered) heterocycloalkyl, R$^{9A}$-substituted (e.g., C$_5$-C$_{10}$ or C$_5$-C$_6$) aryl, or R$^{9A}$-substituted (e.g., 5 to 10 membered or 5 to 6 membered) heteroaryl. R$^{9A}$ may be independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, unsubstituted (e.g., C$_1$-C$_{20}$ or C$_1$-C$_6$) alkyl, unsubstituted (e.g., 2 to 20 membered or 2 to 6 membered) heteroalkyl, unsubstituted (e.g., C$_3$-C$_8$ or C$_5$-C$_7$) cycloalkyl, unsubstituted (e.g., 3 to 8 membered or 3 to 6 membered) heterocycloalkyl, unsubstituted (e.g., C$_5$-C$_{10}$ or C$_5$-C$_6$) aryl, or unsubstituted (e.g., 5 to 10 membered or 5 to 6 membered) heteroaryl.

In embodiments, R$^{10}$ is hydrogen, halogen, =O, =S, —CF$_3$, —CN, —CCl$_3$, —COOH, —CH$_2$COOH, —COCH$_3$, —CONH$_2$, —OH, —OC(O)CH$_3$, —SH, —SO$_2$Cl, —SO$_3$H, —SO$_4$H, —SO$_2$NH$_2$, —NO$_2$, —NH$_2$, —NHNH$_2$, —ONH$_2$ or —NHC=(O)NHNH$_2$. In embodiments, R$^{10}$ is unsubstituted (e.g., C$_1$-C$_{20}$ or C$_1$-C$_6$) alkyl, unsubstituted (e.g., 2 to 20 membered or 2 to 6 membered) heteroalkyl, unsubstituted (e.g., C$_3$-C$_8$ or C$_5$-C$_7$) cycloalkyl, unsubstituted (e.g., 3 to 8 membered or 3 to 6 membered) heterocycloalkyl, unsubstituted (e.g., C$_5$-C$_{10}$ or C$_5$-C$_6$) aryl, or unsubstituted (e.g., 5 to 10 membered or 5 to 6 membered) heteroaryl. In embodiments, R$^{10}$ is R$^{10A}$-substituted (e.g., C$_1$-C$_{20}$ or C$_1$-C$_6$) alkyl, R$^{10A}$-substituted (e.g., 2 to 20 membered or 2 to 6 membered) heteroalkyl, R$^{10A}$-substituted (e.g., C$_3$-C$_8$ or C$_5$-C$_7$) cycloalkyl, R$^{10A}$-substituted (e.g., 3 to 8 membered or 3 to 6 membered) heterocycloalkyl, R$^{10A}$-substituted (e.g., C$_5$-C$_{10}$ or C$_5$-C$_6$) aryl, or R$^{10A}$-substituted (e.g., 5 to 10 membered or 5 to 6 membered) heteroaryl. R$^{10A}$ may be independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, unsubstituted (e.g., C$_1$-C$_{20}$ or C$_1$-C$_6$) alkyl, unsubstituted (e.g., 2 to 20 membered or 2 to 6 membered) heteroalkyl, unsubstituted (e.g., C$_3$-C$_8$ or C$_5$-C$_7$) cycloalkyl, unsubstituted (e.g., 3 to 8 membered or 3 to 6 membered) heterocycloalkyl, unsubstituted (e.g., C$_5$-C$_{10}$ or C$_5$-C$_6$) aryl, or unsubstituted (e.g., 5 to 10 membered or 5 to 6 membered) heteroaryl.

In embodiments, R$^{11}$ is hydrogen, halogen, =O, =S, —CF$_3$, —CN, —CCl$_3$, —COOH, —CH$_2$COOH, —COCH$_3$, —CONH$_2$, —OH, —OC(O)CH$_3$, —SH, —SO$_2$Cl, —SO$_3$H, —SO$_4$H, —SO$_2$NH$_2$, —NO$_2$, —NH$_2$, —NHNH$_2$, —ONH$_2$ or —NHC=(O)NHNH$_2$. In embodiments, R$^{11}$ is unsubstituted (e.g., C$_1$-C$_{20}$ or C$_1$-C$_6$) alkyl, unsubstituted (e.g., 2 to 20 membered or 2 to 6 membered) heteroalkyl, unsubstituted (e.g., C$_3$-C$_8$ or C$_5$-C$_7$) cycloalkyl, unsubstituted (e.g., 3 to 8 membered or 3 to 6 membered) heterocycloalkyl, unsubstituted (e.g., C$_5$-C$_{10}$ or C$_5$-C$_6$) aryl, or unsubstituted (e.g., 5 to 10 membered or 5 to 6 membered) heteroaryl. In embodiments, R$^{11}$ is R$^{11A}$-substituted (e.g., C$_1$-C$_{20}$ or C$_1$-C$_6$) alkyl, R$^{11A}$-substituted (e.g., 2 to 20 membered or 2 to 6 membered) heteroalkyl, R$^{11A}$-substituted (e.g., C$_3$-C$_8$ or C$_5$-C$_7$) cycloalkyl, R$^{11A}$-substituted (e.g., 3 to 8 membered or 3 to 6 membered) heterocycloalkyl, R$^{11A}$-substituted (e.g., C$_5$-C$_{10}$ or C$_5$-C$_6$) aryl, or R$^{11A}$-substituted (e.g., 5 to 10 membered or 5 to 6 membered) heteroaryl. R$^{11A}$ may be independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, unsubstituted (e.g., C$_1$-C$_{20}$ or C$_1$-C$_6$) alkyl, unsubstituted (e.g., 2 to 20 membered or 2 to 6 membered) heteroalkyl, unsubstituted (e.g., C$_3$-C$_8$ or C$_5$-C$_7$) cycloalkyl, unsubstituted (e.g., 3 to 8 membered or 3 to 6 membered) heterocycloalkyl, unsubstituted (e.g., C$_5$-C$_{10}$ or C$_5$-C$_6$) aryl, or unsubstituted (e.g., 5 to 10 membered or 5 to 6 membered) heteroaryl.

In embodiments, R$^{12}$ is hydrogen, halogen, =O, =S, —CF$_3$, —CN, —CCl$_3$, —COOH, —CH$_2$COOH, —COCH$_3$, —CONH$_2$, —OH, —OC(O)CH$_3$, —SH, —SO$_2$Cl, —SO$_3$H, —SO$_4$H, —SO$_2$NH$_2$, —NO$_2$, —NH$_2$, —NHNH$_2$, —ONH$_2$ or —NHC=(O)NHNH$_2$. In embodiments, R$^{12}$ is unsubstituted (e.g., C$_1$-C$_{20}$ or C$_1$-C$_6$) alkyl, unsubstituted (e.g., 2 to 20 membered or 2 to 6 membered) heteroalkyl, unsubstituted (e.g., C$_3$-C$_8$ or C$_5$-C$_7$) cycloalkyl, unsubstituted (e.g., 3 to 8 membered or 3 to 6 membered) heterocycloalkyl, unsubstituted (e.g., C$_5$-C$_{10}$ or C$_5$-C$_6$) aryl, or unsubstituted (e.g., 5 to 10 membered or 5 to 6 membered) heteroaryl. In embodiments, R$^{12}$ is R$^{12A}$-substituted (e.g., C$_1$-C$_{20}$ or C$_1$-C$_6$) alkyl, R$^{12A}$-substituted (e.g., 2 to 20 membered or 2 to 6 membered) heteroalkyl, R$^{12A}$-substituted (e.g., C$_3$-C$_8$ or C$_5$-C$_7$) cycloalkyl, R$^{12A}$-substituted (e.g., 3 to 8 membered or 3 to 6 membered) heterocycloalkyl, R$^{12A}$-substituted (e.g., C$_5$-C$_{10}$ or C$_5$-C$_6$) aryl, or R$^{12A}$-substituted (e.g., 5 to 10 membered or 5 to 6 membered) heteroaryl. R$^{12A}$ may be independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, unsubstituted (e.g., C$_1$-C$_{20}$ or C$_1$-C$_6$) alkyl, unsubstituted (e.g., 2 to 20 membered or 2 to 6 membered) heteroalkyl, unsubstituted (e.g., C$_3$-C$_8$ or C$_5$-C$_7$) cycloalkyl, unsubstituted (e.g., 3 to 8 membered or 3 to 6 membered) heterocycloalkyl, unsubstituted (e.g., C$_5$-C$_{10}$ or C$_5$-C$_6$) aryl, or unsubstituted (e.g., 5 to 10 membered or 5 to 6 membered) heteroaryl.

In embodiments, R$^{13}$ is hydrogen, halogen, =O, =S, —CF$_3$, —CN, —CCl$_3$, —COOH, —CH$_2$COOH, —COCH$_3$, —CONH$_2$, —OH, —OC(O)CH$_3$, —SH, —SO$_2$Cl, —SO$_3$H, —SO$_4$H, —SO$_2$NH$_2$, —NO$_2$, —NH$_2$, —NHNH$_2$, —ONH$_2$ or —NHC=(O)NHNH$_2$. In embodiments, R$^{13}$ is unsubstituted (e.g., C$_1$-C$_{20}$ or C$_1$-C$_6$) alkyl, unsubstituted (e.g., 2 to 20 membered or 2 to 6 membered) heteroalkyl, unsubstituted (e.g., C$_3$-C$_8$ or C$_5$-C$_7$) cycloalkyl, unsubstituted (e.g., 3 to 8 membered or 3 to 6 membered) heterocycloalkyl, unsubstituted (e.g., C$_5$-C$_{10}$ or C$_5$-C$_6$) aryl, or unsubstituted (e.g., 5 to 10 membered or 5 to 6 membered) heteroaryl. In embodiments, R$^{13}$ is R$^{13A}$-substituted (e.g., C$_1$-C$_{20}$ or C$_1$-C$_6$) alkyl, R$^{13A}$-substituted (e.g., 2 to 20 membered or 2 to 6 membered) heteroalkyl, R$^{13A}$-substituted (e.g., C$_3$-C$_8$ or C$_5$-C$_7$) cycloalkyl, R$^{13A}$-substituted (e.g., 3 to 8 membered or 3 to 6 membered) heterocycloalkyl, R$^{13A}$-substituted (e.g., C$_5$-C$_{10}$ or C$_5$-C$_6$) aryl, or R$^{13A}$-substituted (e.g., 5 to 10 membered or 5 to 6 membered) heteroaryl. R$^{13A}$ may be independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —$ONH_2$, —$NHC=(O)NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^{14}$ is hydrogen, halogen, =O, =S, —$CF_3$, —CN, —$CCl_3$, —COOH, —$CH_2COOH$, —$COCH_3$, —$CONH_2$, —OH, —$OC(O)CH_3$, —SH, —$SO_2Cl$, —$SO_3H$, —$SO_4H$, —$SO_2NH_2$, —$NO_2$, —$NH_2$, —$NHNH_2$, —$ONH_2$ or —$NHC=(O)NHNH_2$. In embodiments, $R^{14}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{14}$ is $R^{14A}$-substituted (e.g., $C_1$-$C_{20}$ or $C_1$-$C_6$) alkyl, $R^{14A}$-substituted (e.g., 2 to 20 membered or 2 to 6 membered) heteroalkyl, $R^{14A}$-substituted (e.g., $C_3$-$C_8$ or $C_5$-$C_7$) cycloalkyl, $R^{14A}$-substituted (e.g., 3 to 8 membered or 3 to 6 membered) heterocycloalkyl, $R^{14A}$-substituted (e.g., $C_5$-$C_{10}$ or $C_5$-$C_6$) aryl, or $R^{14A}$-substituted (e.g., 5 to 10 membered or 5 to 6 membered) heteroaryl. $R^{14A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —$NHC=(O)NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^{15}$ is hydrogen, halogen, =O, =S, —$CF_3$, —CN, —$CCl_3$, —COOH, —$CH_2COOH$, —$COCH_3$, —$CONH_2$, —OH, —$OC(O)CH_3$, —SH, —$SO_2Cl$, —$SO_3H$, —$SO_4H$, —$SO_2NH_2$, —$NO_2$, —$NH_2$, —$NHNH_2$, —$ONH_2$ or —$NHC=(O)NHNH_2$. In embodiments, $R^{15}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{15}$ is $R^{15A}$-substituted (e.g., $C_1$-$C_{20}$ or $C_1$-$C_6$) alkyl, $R^{15A}$-substituted (e.g., 2 to 20 membered or 2 to 6 membered) heteroalkyl, $R^{15A}$-substituted (e.g., $C_3$-$C_8$ or $C_5$-$C_7$) cycloalkyl, $R^{15A}$-substituted (e.g., 3 to 8 membered or 3 to 6 membered) heterocycloalkyl, $R^{15A}$-substituted (e.g., $C_5$-$C_{10}$ or $C_5$-$C_6$) aryl, or $R^{15A}$-substituted (e.g., 5 to 10 membered or 5 to 6 membered) heteroaryl. $R^{15A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —$NHC=(O)NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^{16}$ is hydrogen, halogen, =O, =S, —$CF_3$, —CN, —$CCl_3$, —COOH, —$CH_2COOH$, —$COCH_3$, —$CONH_2$, —OH, —$OC(O)CH_3$, —SH, —$SO_2Cl$, —$SO_3H$, —$SO_4H$, —$SO_2NH_2$, —$NO_2$, —$NH_2$, —$NHNH_2$, —$ONH_2$ or —$NHC=(O)NHNH_2$. In embodiments, $R^{16}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{16}$ is $R^{16A}$-substituted (e.g., $C_1$-$C_{20}$ or $C_1$-$C_6$) alkyl, $R^{16A}$-substituted (e.g., 2 to 20 membered or 2 to 6 membered) heteroalkyl, $R^{16A}$-substituted (e.g., $C_3$-$C_8$ or $C_5$-$C_7$) cycloalkyl, $R^{16A}$-substituted (e.g., 3 to 8 membered or 3 to 6 membered) heterocycloalkyl, $R^{16A}$-substituted (e.g., $C_5$-$C_{10}$ or $C_5$-$C_6$) aryl, or $R^{16A}$-substituted (e.g., 5 to 10 membered or 5 to 6 membered) heteroaryl. $R^{16A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —$NHC=(O)NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^{17}$ is hydrogen, halogen, =O, =S, —$CF_3$, —CN, —$CCl_3$, —COOH, —$CH_2COOH$, —$COCH_3$, —$CONH_2$, —OH, —$OC(O)CH_3$, —SH, —$SO_2Cl$, —$SO_3H$, —$SO_4H$, —$SO_2NH_2$, —$NO_2$, —$NH_2$, —$NHNH_2$, —$ONH_2$ or —$NHC=(O)NHNH_2$. In embodiments, $R^{17}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{17}$ is $R^{17A}$-substituted (e.g., $C_1$-$C_{20}$ or $C_1$-$C_6$) alkyl, $R^{17A}$-substituted (e.g., 2 to 20 membered or 2 to 6 membered) heteroalkyl, $R^{17A}$-substituted (e.g., $C_3$-$C_8$ or $C_5$-$C_7$) cycloalkyl, $R^{17A}$-substituted (e.g., 3 to 8 membered or 3 to 6 membered) heterocycloalkyl, $R^{17A}$-substituted (e.g., $C_5$-$C_{10}$ or $C_5$-$C_6$) aryl, or $R^{17A}$-substituted (e.g., 5 to 10 membered or 5 to 6 membered) heteroaryl. $R^{17A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —$NHC=(O)NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^{18}$ is hydrogen, halogen, =O, =S, —$CF_3$, —CN, —$CCl_3$, —COOH, —$CH_2COOH$, —$COCH_3$, —$CONH_2$, —OH, —$OC(O)CH_3$, —SH, —$SO_2Cl$, —$SO_3H$, —$SO_4H$, —$SO_2NH_2$, —$NO_2$, —$NH_2$, —$NHNH_2$, —$ONH_2$ or —$NHC=(O)NHNH_2$. In embodiments, $R^{18}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{18}$ is $R^{18A}$-substituted (e.g., $C_1$-$C_{20}$ or $C_1$-$C_6$) alkyl, $R^{18A}$-substituted (e.g., 2 to 20 membered or 2 to 6 membered) heteroalkyl, $R^{18A}$-substituted (e.g., $C_3$-$C_8$ or $C_5$-$C_7$) cycloalkyl, $R^{18A}$-substituted (e.g., 3 to 8 membered or 3 to 6 membered) heterocycloalkyl, $R^{18A}$-substituted (e.g., $C_5$-$C_{10}$ or $C_5$-$C_6$) aryl, or $R^{18A}$-substituted (e.g., 5 to 10 membered or 5 to 6 membered) heteroaryl. $R^{18A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^{19}$ is hydrogen, halogen, =O, =S, —$CF_3$, —CN, —$CCl_3$, —COOH, —$CH_2COOH$, —$COCH_3$, —$CONH_2$, —OH, —$OC(O)CH_3$, —SH, —$SO_2Cl$, —$SO_3H$, —$SO_4H$, —$SO_2NH_2$, —$NO_2$, —$NH_2$, —$NHNH_2$, —$ONH_2$ or —NHC=(O)$NHNH_2$. In embodiments, $R^{19}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{19}$ is $R^{19A}$-substituted (e.g., $C_1$-$C_{20}$ or $C_1$-$C_6$) alkyl, $R^{19A}$-substituted (e.g., 2 to 20 membered or 2 to 6 membered) heteroalkyl, $R^{19A}$-substituted (e.g., $C_3$-$C_8$ or $C_5$-$C_7$) cycloalkyl, $R^{19A}$-substituted (e.g., 3 to 8 membered or 3 to 6 membered) heterocycloalkyl, $R^{19A}$-substituted (e.g., $C_5$-$C_{10}$ or $C_5$-$C_6$) aryl, or $R^{19A}$-substituted (e.g., 5 to 10 membered or 5 to 6 membered) heteroaryl. $R^{19A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^{20}$ is hydrogen, halogen, =O, =S, —$CF_3$, —CN, —$CCl_3$, —COOH, —$CH_2COOH$, —$COCH_3$, —$CONH_2$, —OH, —$OC(O)CH_3$, —SH, —$SO_2Cl$, —$SO_3H$, —$SO_4H$, —$SO_2NH_2$, —$NO_2$, —$NH_2$, —$NHNH_2$, —$ONH_2$ or —NHC=(O)$NHNH_2$. In embodiments, $R^{20}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{20}$ is $R^{20A}$-substituted (e.g., $C_1$-$C_{20}$ or $C_1$-$C_6$) alkyl, $R^{20A}$-substituted (e.g., 2 to 20 membered or 2 to 6 membered) heteroalkyl, $R^{20A}$-substituted (e.g., $C_3$-$C_8$ or $C_5$-$C_7$) cycloalkyl, $R^{20A}$-substituted (e.g., 3 to 8 membered or 3 to 6 membered) heterocycloalkyl, $R^{20A}$-substituted (e.g., $C_5$-$C_{10}$ or $C_5$-$C_6$) aryl, or $R^{20A}$-substituted (e.g., 5 to 10 membered or 5 to 6 membered) heteroaryl. $R^{20A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^{21}$ is hydrogen, halogen, =O, =S, —$CF_3$, —CN, —$CCl_3$, —COOH, —$CH_2COOH$, —$COCH_3$, —$CONH_2$, —OH, —$OC(O)CH_3$, —SH, —$SO_2Cl$, —$SO_3H$, —$SO_4H$, —$SO_2NH_2$, —$NO_2$, —$NH_2$, —$NHNH_2$, —$ONH_2$ or —NHC=(O)$NHNH_2$. In embodiments, $R^{21}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{21}$ is $R^{21A}$-substituted (e.g., $C_1$-$C_{20}$ or $C_1$-$C_6$) alkyl, $R^{21A}$-substituted (e.g., 2 to 20 membered or 2 to 6 membered) heteroalkyl, $R^{21A}$-substituted (e.g., $C_3$-$C_8$ or $C_5$-$C_7$) cycloalkyl, $R^{21A}$-substituted (e.g., 3 to 8 membered or 3 to 6 membered) heterocycloalkyl, $R^{21A}$-substituted (e.g., $C_5$-$C_{10}$ or $C_5$-$C_6$) aryl, or $R^{21A}$-substituted (e.g., 5 to 10 membered or 5 to 6 membered) heteroaryl. $R^{21A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^{22}$ is hydrogen, halogen, =O, =S, —$CF_3$, —CN, —$CCl_3$, —COOH, —$CH_2COOH$, —$COCH_3$, —$CONH_2$, —OH, —$OC(O)CH_3$, —SH, —$SO_2Cl$, —$SO_3H$, —$SO_4H$, —$SO_2NH_2$, —$NO_2$, —$NH_2$, —$NHNH_2$, —$ONH_2$ or —NHC=(O)$NHNH_2$. In embodiments, $R^{22}$ is unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl. In embodiments, $R^{22}$ is $R^{22A}$-substituted (e.g., $C_1$-$C_{20}$ or $C_1$-$C_6$) alkyl, $R^{22A}$-substituted (e.g., 2 to 20 membered or 2 to 6 membered) heteroalkyl, $R^{22A}$-substituted (e.g., $C_3$-$C_8$ or $C_5$-$C_7$) cycloalkyl, $R^{22A}$-substituted (e.g., 3 to 8 membered or 3 to 6 membered) heterocycloalkyl, $R^{22A}$-substituted (e.g., $C_5$-$C_{10}$ or $C_5$-$C_6$) aryl, or $R^{22A}$-substituted (e.g., 5 to 10 membered or 5 to 6 membered) heteroaryl. $R^{22A}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$X^a$, $X^b$, $X^c$, $X^d$, $X^e$, $X^f$ and $X^g$ are independently —F, —Cl, —Br, or —I.

$n_1$, $n_2$, $n_3$, $n_4$, $n_5$, $n_6$ and $n_7$ are independently an integer from 0 to 4.

$m_1$, $m_2$, $m_3$, $m_4$, $m_5$, $m_6$ and $m_7$ are independently an integer from 1 to 2.

$v_1$, $v_2$, $v_3$, $v_4$, $v_5$, $v_6$ and $v_7$ are independently an integer from 1 to 2.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$pyridyl, -benzyl, —CH$_2$-difluorophenyl, —CH$_2$-cyclopropyl, —CH$_2$-4-(CH$_2$NHC(O)-tbutyl)phenyl, —CH$_2$-5-nitrofuranyl, —CH$_2$CH$_2$-5-nitrofuranyl, —CH$_2$-2-(5-CF$_3$)furanyl, —CH$_2$-fluorophenyl, —CH$_2$-chlorophenyl, —CH$_2$-nitrophenyl, —CH$_2$-cyanophenyl, —CH(CH$_3$)C(O)Ph, —CH$_2$-(methyl)phenyl, —CH$_2$-trifluoromethylphenyl, —CH$_2$-trifluoromethoxyphenyl, —CH$_2$-difluoromethoxyphenyl, —CH$_2$-3-(2-CO$_2$CH$_3$)thienyl, —CH$_2$-3-(2-bromo)thienyl, —CH$_2$-3-isoxazolyl, —CH$_2$-5-isoxazolyl, —CH$_2$-5-(3-phenyl)isoxazolyl, —CH$_2$-3-(2-bromo)pyridyl, —CH$_2$-3-thienyl, —CH$_2$-2-(5-CO$_2$CH$_2$CH$_3$)furanyl, —CH$_2$-4-(2-methyl)thiazolyl, —CH$_2$-2-(5-CO$_2$CH$_3$)furanyl, —CH$_2$-5-(3-methyl)isoxazolyl, or —CH$_2$—CH(CH$_3$)phenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$pyridyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not -benzyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-difluorophenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-cyclopropyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-4-(CH$_2$NHC(O)-tbutyl)phenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-5-nitrofuranyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$CH$_2$-5-nitrofuranyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-2-(5-CF$_3$)furanyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-fluorophenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-chlorophenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-nitrophenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-cyanophenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH(CH$_3$)C(O)Ph.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-(methyl)phenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-trifluoromethylphenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-trifluoromethoxyphenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-difluoromethoxyphenyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-3-(2-CO$_2$CH$_3$)thienyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-3-(2-bromo)thienyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-3-isoxazolyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-5-isoxazolyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-5-(3-phenyl)isoxazolyl.

Further regarding the compound with structure of formula (I), if $R^1$, $R^2$, and $R^3$ are independently hydrogen, —Cl, —F, —OCH$_3$, or —CF$_3$, then -L$^1$-R$^{66}$ is not —CH$_2$-3-(2-bromo)pyridyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-3-thienyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-2-(5-CO$_2$CH$_2$CH$_3$)furanyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-4-(2-methyl)thiazolyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-2-(5-CO$_2$CH$_3$)furanyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$-5-(3-methyl)isoxazolyl.

Further regarding the compound with structure of formula (I), if $R^1$, $R^2$, and $R^3$ are independently hydrogen, —Cl, —F, —OCH$_3$, or —CF$_3$, then -L$^1$-R$^6$ is not —CH$_2$—CH(CH$_3$)phenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$pyridyl, -benzyl, —CH$_2$-difluorophenyl, —CH$_2$-cyclopropyl, —CH$_2$-4-(CH$_2$NHC(O)-tbutyl)phenyl, —CH$_2$-5-nitrofuranyl, —CH$_2$CH$_2$-5-nitrofuranyl, —CH$_2$-2-(5-CF$_3$)furanyl, —CH$_2$-fluorophenyl, —CH$_2$-chlorophenyl, —CH$_2$-nitrophenyl, —CH$_2$-cyanophenyl, —CH(CH$_3$)C(O)Ph, —CH$_2$-(methyl)phenyl, —CH$_2$-trifluoromethylphenyl, —CH$_2$-trifluoromethoxyphenyl, —CH$_2$-difluoromethoxyphenyl, —CH$_2$-3-(2-CO$_2$CH$_3$)thienyl, —CH$_2$-3-(2-bromo)thienyl, —CH$_2$-3-isoxazolyl, —CH$_2$-5-isoxazolyl, —CH$_2$-5-(3-phenyl)isoxazolyl, —CH$_2$-3-(2-bromo)pyridyl, —CH$_2$-3-thienyl, —CH$_2$-2-(5-CO$_2$CH$_2$CH$_3$)furanyl, —CH$_2$-4-(2-methyl)thiazolyl, —CH$_2$-2-(5-CO$_2$CH$_3$)furanyl, —CH$_2$-5-(3-methyl)isoxazolyl, or —CH$_2$—CH(CH$_3$)phenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$pyridyl.

Further regarding the compound with structure of formula (I), if $R^1$, $R^2$, and $R^3$ are independently hydrogen, —Cl, —F, —OCH$_3$, or —CF$_3$, then $R^6$ is not -benzyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-difluorophenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-cyclopropyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-4-(CH$_2$NHC(O)-tbutyl)phenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-5-nitrofuranyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$CH$_2$-5-nitrofuranyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-2-(5-CF$_3$)furanyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-fluorophenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-chlorophenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-nitrophenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-cyanophenyl.

Further regarding the compound with structure of formula (I), if $R^1$, $R^2$, and $R^3$ are independently hydrogen, —Cl, —F, —OCH$_3$, or —CF$_3$, then $R^6$ is not —CH(CH$_3$)C(O)Ph.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-(methyl)phenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-trifluoromethylphenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-trifluoromethoxyphenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-difluoromethoxyphenyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-3-(2-CO$_2$CH$_3$)thienyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-3-(2-bromo)thienyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-3-isoxazolyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-5-isoxazolyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-5-(3-phenyl)isoxazolyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-3-(2-bromo)pyridyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-3-thienyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-2-(5-CO$_2$CH$_2$CH$_3$)furanyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-4-(2-methyl)thiazolyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-2-(5-CO$_2$CH$_3$)furanyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$-5-(3-methyl)isoxazolyl.

Further regarding the compound with structure of formula (I), if $R^1$, $R^2$, and $R^3$ are independently hydrogen, —Cl, —F, —OCH$_3$, or —CF$_3$, then $R^6$ is not —CH$_2$—CH(CH$_3$)phenyl.

In embodiments, if $L^1$ is —CH$_2$— and $R^6$ is phenyl, then $R^{6A}$ is not —F, —CF$_3$, —OCHF$_2$, —NO$_2$, —OCF$_3$, —CH$_3$, —CN, or —Cl. In embodiments, if $L^1$ is —CH$_2$— and $R^6$ is phenyl, then $R^{6A}$ is not halogen, —CX$^f_3$, —OR$^{19}$, or substituted or unsubstituted C$_1$-C$_5$ alkyl, wherein X$^f$ is halogen and R$^{19}$ is substituted or unsubstituted C$_1$-C$_5$ alkyl.

In embodiments, if $L^1$ is —CH$_2$— and $R^6$ is $R^{6A}$-substituted 6-membered aryl, then $R^{6A}$ is not halogen, —CX$^f_3$, —OR$^{19}$, or substituted or unsubstituted C$_1$-C$_5$ alkyl, wherein X$^f$ is halogen and R$^{19}$ is substituted or unsubstituted C$_1$-C$_5$ alkyl.

In embodiments, if $L^1$ is unsubstituted C$_1$-C$_5$ alkylene and $R^6$ is phenyl, then $R^{6A}$ is not halogen, —CX$^f_3$, —OR$^{19}$, or substituted or unsubstituted C$_1$-C$_5$ alkyl, wherein X$^f$ is halogen and R$^{19}$ is substituted or unsubstituted C$_1$-C$_5$ alkyl.

In embodiments, if $L^1$ is unsubstituted C$_1$-C$_5$ alkylene and $R^6$ is $R^{6A}$-substituted 6-membered aryl, then $R^{6A}$ is not halogen, —CX$^f_3$, —OR$^{19}$, or substituted or unsubstituted C$_1$-C$_5$ alkyl, wherein X$^f$ is halogen and R$^{19}$ is substituted or unsubstituted C$_1$-C$_5$ alkyl.

In embodiments, if L$^1$ is —CH$_2$— and R$^6$ is furanyl, then R$^{6A}$ is not —CF$_3$, —NO$_2$, —C(O)OCH$_3$ or —C(O)OCH$_2$CH$_3$ In embodiments, if L$^1$ is —CH$_2$— and R$^6$ is furanyl, then R$^{6A}$ is not —CX$^f_3$, or —C(O)OR$^{19}$ wherein X$^f$ is halogen and R$^{19}$ is substituted or unsubstituted C$_1$-C$_5$ alkyl.

In embodiments, if L$^1$ is —CH$_2$— and R$^6$ is R$^{6A}$-substituted 5-membered heteroaryl, then R$^{6A}$ is not —CX$^f_3$, or —C(O)OR$^{19}$, wherein X$^f$ is halogen and R$^{19}$ is substituted or unsubstituted C$_1$-C$_5$ alkyl.

In embodiments, if L$^1$ is unsubstituted C$_1$-C$_5$ alkylene and R$^6$ is furanyl, then R$^{6A}$ is not —CX$^f_3$, or —C(O)OR$^{19}$, wherein X$^f$ is halogen and R$^{19}$ is substituted or unsubstituted C$_1$-C$_5$ alkyl.

In embodiments, if L$^1$ is unsubstituted C$_1$-C$_5$ alkylene and R$^6$ is R$^{6A}$-substituted 5-membered heteroaryl, then R$^{6A}$ is not —CX$^f_3$, or —C(O)OR$^{19}$, wherein X$^f$ is halogen and R$^{19}$ is substituted or unsubstituted C$_1$-C$_5$ alkyl.

In embodiments, if L$^1$ is —CH$_2$— and R$^6$ is thiophene, then R$^{6A}$ is not —Br, —C(O)OCH$_3$, or —C(O)OCH$_2$CH$_3$.

In embodiments, if L$^1$ is —CH$_2$— and R$^6$ is thiophene, then R$^{6A}$ is not halogen or —C(O)OR$^{19}$, wherein R$^{19}$ is substituted or unsubstituted C$_1$-C$_5$ alkyl.

In embodiments, if L$^1$ is —CH$_2$— and R$^6$ is R$^{6A}$-substituted 5-membered heteroaryl, then R$^{6A}$ is not halogen or —C(O)OR$^{19}$, wherein R$^{19}$ is substituted or unsubstituted C$_1$-C$_5$ alkyl.

In embodiments, if L$^1$ is unsubstituted C$_1$-C$_5$ alkylene and R$^6$ is thiophene, then R$^{6A}$ is not halogen or —C(O)OR$^{19}$, wherein R$^{19}$ is substituted or unsubstituted C$_1$-C$_5$ alkyl.

In embodiments, if L$^1$ is unsubstituted C$_1$-C$_5$ alkylene and R$^6$ is R$^{6A}$-substituted 5-membered heteroaryl, then R$^{6A}$ is not halogen or —C(O)OR$^{19}$, wherein R$^{19}$ is substituted or unsubstituted C$_1$-C$_5$ alkyl.

In embodiments, if L$^1$ is —CH$_2$— and R$^6$ is oxazolyl, then R$^{6A}$ is not methyl or phenyl.

In embodiments, if L$^1$ is —CH$_2$— and R$^6$ is oxazolyl, then R$^{6A}$ is not substituted or unsubstituted C$_1$-C$_5$ alkyl or substituted or substituted 6-membered aryl.

In embodiments, if L$^1$ is —CH$_2$— and R$^6$ is R$^{6A}$-substituted 5-membered heteroaryl, then R$^{6A}$ is not substituted or unsubstituted C$_1$-C$_5$ alkyl or substituted or unsubstituted 6-membered aryl.

In embodiments, if L$^1$ is unsubstituted C$_1$-C$_5$ alkylene and R$^6$ is oxazolyl, then R$^{6A}$ is not substituted or unsubstituted C$_1$-C$_5$ alkyl or substituted or unsubstituted 6-membered aryl.

In embodiments, if L$^1$ is unsubstituted C$_1$-C$_5$ alkylene and R$^6$ is R$^{6A}$-substituted 5-membered heteroaryl, then R$^{6A}$ is not substituted or unsubstituted C$_1$-C$_5$ alkyl or substituted or unsubstituted 6-membered aryl.

In embodiments, if L$^1$ is —CH$_2$— and R$^6$ is pyridyl, then R$^{6A}$ is not —Br.

In embodiments, if L$^1$ is —CH$_2$— and R$^6$ is pyridyl, then R$^{6A}$ is not halogen.

In embodiments, if L$^1$ is —CH$_2$— and R$^6$ is R$^{6A}$-substituted 6-membered heteroaryl, then R$^{6A}$ is not halogen.

In embodiments, if L$^1$ is unsubstituted C$_1$-C$_5$ alkylene and R$^6$ is pyridyl, then R$^{6A}$ is not halogen.

In embodiments, if L$^1$ is unsubstituted C$_1$-C$_5$ alkylene and R$^6$ is R$^{6A}$-substituted 6-membered heteroaryl, then R$^{6A}$ is not halogen.

In embodiments, if L$^1$ is —CH$_2$— and R$^6$ is thiazolyl, then R$^{6A}$ is not —CH$_3$ or —C(O)OCH$_3$.

In embodiments, if L$^1$ is —CH$_2$— and R$^6$ is thiazolyl, then R$^{6A}$ is not substituted or unsubstituted C$_1$-C$_5$ alkyl or —C(O)OR$^{19}$, wherein R$^{19}$ is substituted or unsubstituted C$_1$-C$_5$ alkyl.

In embodiments, if L$^1$ is —CH$_2$— and R$^6$ is R$^{6A}$-substituted 5-membered heteroaryl, then R$^{6A}$ is not substituted or unsubstituted C$_1$-C$_5$ alkyl or —C(O)OR$^{19}$, wherein R$^{19}$ is substituted or unsubstituted C$_1$-C$_5$ alkyl.

In embodiments, if L$^1$ is unsubstituted C$_1$-C$_5$ alkylene and R$^6$ is thiazolyl, then R$^{6A}$ is not substituted or unsubstituted C$_1$-C$_5$ alkyl or —C(O)OR$^{19}$, wherein R$^{19}$ is substituted or unsubstituted C$_1$-C$_5$ alkyl.

In embodiments, if L$^1$ is unsubstituted C$_1$-C$_5$ alkylene and R$^6$ is R$^{6A}$-substituted 5-membered heteroaryl, then R$^{6A}$ is not substituted or unsubstituted C$_1$-C$_5$ alkyl or —C(O)OR$^{19}$, wherein R$^{19}$ is substituted or unsubstituted C$_1$-C$_5$ alkyl.

Further to the compound of formula (I), in embodiments R$^1$ is —Br, —SR$^9$, —OR$^9$, —NO$_2$, —CN, or substituted or unsubstituted C$_1$-C$_{10}$ alkyl.

In embodiments, R$^1$ is —SR$^9$ and R$^9$ is substituted or unsubstituted C$_1$-C$_{10}$ alkyl.

In embodiments, R$^1$ is —SR$^9$ and R$^9$ is substituted or unsubstituted C$_1$-C$_5$ alkyl.

In embodiments, R$^1$ is —SR$^9$ and R$^9$ is unsubstituted C$_1$-C$_5$ alkyl.

In embodiments, R$^1$ is —SR$^9$ and R$^9$ is methyl.

In embodiments, R$^1$ is —OR$^9$ and R$^9$ is substituted or unsubstituted C$_2$-C$_{10}$ alkyl. In embodiments, R$^1$ is —OR$^9$ and R$^9$ is substituted or unsubstituted C$_2$-C$_5$ alkyl. In embodiments, R$^1$ is —OR$^9$ and R$^9$ is unsubstituted C$_2$-C$_5$ alkyl. In embodiments, R$^1$ is substituted or unsubstituted C$_1$-C$_5$ alkyl. In embodiments, R$^1$ is unsubstituted C$_1$-C$_5$ alkyl. In embodiments, R$^1$ is unsubstituted methyl, ethyl, propyl, isopropyl, butyl or pentyl. In embodiments, R$^1$ is unsubstituted methyl. In embodiments, R$^1$ is unsubstituted ethyl. In embodiments, R$^1$ is unsubstituted propyl. In embodiments, R$^1$ is unsubstituted isopropyl. In embodiments, R$^1$ is unsubstituted butyl. In embodiments, R$^1$ is unsubstituted pentyl. In embodiments, R$^1$ is unsubstituted branched C$_1$-C$_5$ alkyl.

Further to the compound of formula (I), in embodiments R$^2$ is —Br, —SR$^{11}$, —OR$^{11}$, —NO$_2$, —CN, or substituted or unsubstituted C$_1$-C$_{10}$ alkyl. In embodiments, R$^2$ is —SR$^{11}$ and R$^{11}$ is substituted or unsubstituted C$_1$-C$_{10}$ alkyl. In embodiments, R$^2$ is —SR$^{11}$ and R$^{11}$ is substituted or unsubstituted C$_1$-C$_5$ alkyl. In embodiments, R$^2$ is —SR$^{11}$ and R$^{11}$ is unsubstituted C$_1$-C$_5$ alkyl. In embodiments, R$^2$ is —SR$^{11}$ and R$^{11}$ is methyl. In embodiments, R$^2$ is —OR$^{11}$ and R$^{11}$ is substituted or unsubstituted C$_2$-C$_{10}$ alkyl. In embodiments, R$^2$ is —OR$^{11}$ and R$^{11}$ is substituted or unsubstituted C$_2$-C$_5$ alkyl. In embodiments, R$^2$ is —OR$^{11}$ and R$^{11}$ is unsubstituted C$_2$-C$_5$ alkyl. In embodiments, R$^2$ is substituted or unsubstituted C$_1$-C$_5$ alkyl. In embodiments, R$^2$ is unsubstituted C$_1$-C$_5$ alkyl. In embodiments, R$^2$ is unsubstituted branched C$_1$-C$_5$ alkyl. In embodiments, R$^2$ is unsubstituted methyl. In embodiments, R$^2$ is unsubstituted ethyl. In embodiments, R$^2$ is unsubstituted propyl. In embodiments, R$^2$ is unsubstituted isopropyl. In embodiments, R$^2$ is unsubstituted butyl. In embodiments, R$^2$ is unsubstituted pentyl.

Further to the compound of formula (I), in embodiments R$^3$ is —Br, —SR$^{13}$, —OR$^{13}$, —NO$_2$, —CN, or substituted or unsubstituted C$_1$-C$_{10}$ alkyl. In embodiments, R$^3$ is —SR$^{13}$ and R$^{13}$ is substituted or unsubstituted C$_1$-C$_{10}$ alkyl. In embodiments, R$^3$ is —SR$^{13}$ and R$^{13}$ is substituted or unsubstituted C$_1$-C$_5$ alkyl. In embodiments, R$^3$ is —SR$^{13}$ and R$^{13}$ is unsubstituted C$_1$-C$_5$ alkyl. In embodiments, R$^3$ is —SR$^{13}$ and R$^{13}$ is methyl. In embodiments, R$^3$ is —SR$^{13}$ and R$^{13}$ is ethyl. In embodiments, $R^3$ is —$SR^{13}$ and $R^{13}$ is propyl. In embodiments, $R^3$ is —$SR^{13}$ and $R^{13}$ is isopropyl. In embodiments, $R^3$ is —$SR^{13}$ and $R^{13}$ is butyl. In embodiments, $R^3$ is —$SR^{13}$ and $R^{13}$ is pentyl. In embodiments, $R^3$ is —$OR^{13}$ and $R^{13}$ is substituted or unsubstituted $C_2$-$C_{10}$ alkyl. In embodiments, $R^3$ is —$OR^{13}$ and $R^{13}$ is substituted or unsubstituted $C_2$-$C_5$ alkyl. In embodiments, $R^3$ is —$OR^{13}$ and $R^{13}$ is unsubstituted $C_2$-$C_5$ alkyl. In embodiments, $R^3$ is substituted or unsubstituted $C_1$-$C_5$ alkyl. In embodiments, $R^3$ is unsubstituted $C_1$-$C_5$ alkyl. In embodiments, $R^3$ is unsubstituted branched $C_1$-$C_5$ alkyl. In embodiments, $R^3$ is unsubstituted methyl. In embodiments, $R^3$ is unsubstituted ethyl. In embodiments, $R^3$ is unsubstituted propyl. In embodiments, $R^3$ is unsubstituted isopropyl. In embodiments, $R^3$ is unsubstituted butyl. In embodiments, $R^3$ is unsubstituted pentyl.

Further to the compound of formula (I), in embodiments $R^8$ is —Br, —CN, —$SR^{15}$, —$OR^{15}$, —$NR^{15}R^{16}$, or substituted or unsubstituted $C_1$-$C_{10}$ alkyl. In embodiments, $R^8$ is —$SR^{15}$ and $R^{15}$ is hydrogen or substituted or unsubstituted $C_1$-$C_{10}$ alkyl. In embodiments, $R^8$ is —$SR^{15}$ and $R^{15}$ is substituted or unsubstituted $C_1$-$C_5$ alkyl. In embodiments, $R^8$ is —$SR^{15}$ and $R^{15}$ is unsubstituted $C_1$-$C_5$ alkyl. In embodiments, $R^8$ is —$SR^{15}$ and $R^{15}$ is methyl. In embodiments, $R^8$ is —$SR^{15}$ and $R^{15}$ is ethyl. In embodiments, $R^8$ is —$SR^{15}$ and $R^{15}$ is propyl. In embodiments, $R^8$ is —$SR^{15}$ and $R^{15}$ is isopropyl. In embodiments, $R^8$ is —$SR^{15}$ and $R^{15}$ is butyl. In embodiments, $R^8$ is —$SR^{15}$ and $R^{15}$ is pentyl. In embodiments, $R^8$ is —$OR^{15}$ and $R^{15}$ is hydrogen or substituted or unsubstituted $C_2$-$C_{10}$ alkyl. In embodiments, $R^8$ is —$OR^{15}$ and $R^{15}$ is substituted or unsubstituted $C_2$-$C_5$ alkyl. In embodiments, $R^8$ is —$OR^{15}$ and $R^{15}$ is unsubstituted $C_2$-$C_5$ alkyl. In embodiments, $R^8$ is —$OR^{15}$ and $R^{15}$ is hydrogen, methyl, ethyl or isopropyl. In embodiments, $R^8$ is —$OR^{15}$ and $R^{15}$ is hydrogen. In embodiments, $R^8$ is —$OR^{15}$ and $R^{15}$ is methyl. In embodiments, $R^8$ is —$OR^{15}$ and $R^{15}$ is ethyl. In embodiments, $R^8$ is —$OR^{15}$ and $R^{15}$ is isopropyl. In embodiments, $R^8$ is —$NR^{15}R^{16}$ and $R^{15}$ and $R^{16}$ are independently hydrogen, O or substituted or unsubstituted $C_2$-$C_{10}$ alkyl. In embodiments, $R^8$ is —$NR^{15}R^{16}$ and $R^{15}$ and $R^{16}$ are independently hydrogen, O, methyl or ethyl. In embodiments, $R^8$ is substituted or unsubstituted $C_1$-$C_5$ alkyl. In embodiments, $R^8$ is unsubstituted $C_1$-$C_5$ alkyl. In embodiments, $R^8$ is unsubstituted branched $C_1$-$C_5$ alkyl. In embodiments, $R^8$ is unsubstituted methyl. In embodiments, $R^8$ is unsubstituted ethyl. In embodiments, $R^8$ is unsubstituted propyl. In embodiments, $R^8$ is unsubstituted isopropyl. In embodiments, $R^8$ is unsubstituted butyl. In embodiments, $R^8$ is unsubstituted pentyl.

Further to the compound of formula (I), in embodiments $R^4$ is substituted or unsubstituted $C_1$-$C_{10}$ alkyl. In embodiments, $R^4$ is substituted or unsubstituted $C_1$-$C_5$ alkyl. In embodiments, $R^4$ is unsubstituted $C_1$-$C_5$ alkyl. In embodiments, $R^4$ is methyl. In embodiments, $R^4$ is ethyl. In embodiments, $R^4$ is propyl. In embodiments, $R^4$ is isopropyl. In embodiments, $R^4$ is butyl. In embodiments, $R^4$ is pentyl.

Further to the compound of formula (I), in embodiments $R^5$ is halogen or substituted or unsubstituted $C_1$-$C_{10}$ alkyl. In embodiments, $R^5$ is halogen or substituted or unsubstituted $C_1$-$C_5$ alkyl. In embodiments, $R^5$ is halogen. In embodiments, $R^5$ is unsubstituted $C_1$-$C_5$ alkyl. In embodiments, $R^5$ is unsubstituted methyl. In embodiments, $R^5$ is unsubstituted ethyl. In embodiments, $R^5$ is unsubstituted propyl. In embodiments, $R^5$ is unsubstituted isopropyl. In embodiments, $R^5$ is unsubstituted butyl. In embodiments, $R^5$ is unsubstituted pentyl.

Further to the compound of formula (I), in embodiments $R^6$ is $R^{6A}$-substituted heterocycloalkyl, $R^{6A}$-substituted aryl or $R^{6A}$-substituted heteroaryl. In embodiments, $R^6$ is $R^{6A}$-substituted 5-6 membered heterocycloalkyl, $R^{6A}$-substituted $C_5$-$C_6$ aryl or $R^{6A}$-substituted 5 to 6 membered heteroaryl. In embodiments, $R^{6A}$ is substituted or unsubstituted $C_1$-$C_{10}$ alkyl. In embodiments, $R^{6A}$ is substituted or unsubstituted $C_1$-$C_5$ alkyl. In embodiments, $R^{6A}$ is substituted or unsubstituted $C_1$-$C_3$ alkyl. In embodiments, $R^{6A}$ is substituted $C_1$-$C_3$ alkyl. In embodiments, $R^{6A}$ is hydroxymethyl.

In embodiments, $R^6$ is $R^{6A}$-substituted furanyl. In embodiments, $R^6$ is $R^{6A}$-substituted thiophene. In embodiments, $R^6$ is $R^{6A}$-substituted oxazolyl. In embodiments, $R^6$ is $R^{6A}$-substituted pyridyl. In embodiments, $R^6$ is $R^{6A}$-substituted thiazole. In embodiments, $R^6$ is $R^{6A}$-substituted phenyl.

In embodiments, $R^{6A}$ is —Br, —$SR^{19}$, —$SO_{n6}R^{19}$, —C(O)—$OR^{19}$, —$OR^{19}$, substituted or unsubstituted alkyl or substituted or unsubstituted aryl. In embodiments, $R^{6A}$ is —$SR^{19}$ and $R^{19}$ is substituted or unsubstituted $C_1$-$C_5$ alkyl. In embodiments, $R^{6A}$ is —$SR^{19}$ and $R^{19}$ is methyl or ethyl. In embodiments $R^{19}$ is substituted $C_1$-$C_5$ alkyl. In embodiments, $R^{19}$ is substituted $C_1$ alkyl. In embodiments, $R^{19}$ is trifluoromethyl. In embodiments, $R^{6A}$ is —$SO_{n6}R^{19}$, $n_6$ is 1 or 2 and $R^{19}$ is substituted or unsubstituted $C_1$-$C_5$ alkyl. In embodiments, $R^{19}$ is unsubstituted $C_1$-$C_5$ alkyl. In embodiments, $R^{19}$ is unsubstituted $C_1$-$C_3$ alkyl. In embodiments, $R^{19}$ is methyl or ethyl.

In embodiments, $R^{6A}$ is —C(O)—$OR^{19}$ and $R^{19}$ is hydrogen or substituted or unsubstituted $C_1$-$C_5$ alkyl. In embodiments, $R^{19}$ is hydrogen. In embodiments, $R^{19}$ is unsubstituted $C_1$-$C_5$ alkyl. In embodiments, $R^{19}$ is unsubstituted $C_1$-$C_3$ alkyl. In embodiments, $R^{19}$ is methyl. In embodiments, $R^{19}$ is ethyl. In embodiments, $R^{19}$ is isopropyl.

In embodiments, $R^{6A}$ is —$OR^{19}$ and $R^{19}$ is trifluoromethyl or substituted or unsubstituted $C_1$-$C_5$ alkyl. In embodiments, $R^{19}$ is trifluoromethyl. In embodiments, $R^{19}$ is unsubstituted $C_1$-$C_5$ alkyl. In embodiments, $R^{19}$ is unsubstituted $C_1$-$C_3$ alkyl. In embodiments, $R^{19}$ is methyl. In embodiments, $R^{19}$ is ethyl. In embodiments, $R^{19}$ is isopropyl. In embodiments, $R^{19}$ is substituted $C_1$-$C_5$ alkyl. In embodiments, $R^{19}$ is substituted ethyl.

Further to the compound of formula (I), in embodiments $R^{6A}$ is —Br, —$SR^{19}$, —$SO_{n6}R^{19}$, —C(O)—$OR^{19}$, —$OR^{19}$, substituted or unsubstituted alkyl or substituted or unsubstituted aryl. In embodiments, $R^{6A}$ is substituted or unsubstituted $C_1$-$C_{10}$ alkyl. In embodiments, $R^{6A}$ is substituted or unsubstituted $C_1$-$C_5$ alkyl. In embodiments, $R^{6A}$ is substituted or unsubstituted $C_1$-$C_3$ alkyl. In embodiments, $R^{6A}$ is substituted $C_1$-$C_3$ alkyl. In embodiments, $R^{6A}$ is hydroxymethyl. In embodiments, $R^{6A}$ is unsubstituted $C_1$-$C_5$ alkyl. In embodiments, $R^{6A}$ is methyl. In embodiments, $R^{6A}$ is ethyl. In embodiments, $R^{6A}$ is propyl. In embodiments, $R^{6A}$ is isopropyl. In embodiments, $R^{6A}$ is butyl. In embodiments, $R^{6A}$ is pentyl.

In embodiments, $R^{6A}$ is trifluoromethyl, —Br, —$SR^{19}$, —$SO_{n6}R^{19}$, —C(O)—$OR^{19}$, —$OR^{19}$, substituted or unsubstituted alkyl or substituted or unsubstituted aryl. In embodiments, $R^{6A}$ is —Cl, —F, —$CX^f_3$, —$SR^{19}$, —$SO_{n6}R^{19}$, —C(O)—$OR^{19}$, —$OR^{19}$, substituted or unsubstituted alkyl or substituted or unsubstituted aryl. In embodiments, $R^{6A}$ is —Cl or —$NR^{19}R^{20}$. In embodiments, $R^{6A}$ is —$NR^{19}R^{20}$, $R^{19}$ is hydrogen and $R^{20}$ is —OC(O)$CH_3$.

Further to the compound of formula (I), in embodiments $R^7$ is substituted or unsubstituted $C_1$-$C_{10}$ alkyl. In embodiments, $R^7$ is substituted or unsubstituted $C_1$-$C_5$ alkyl. In embodiments, $R^7$ is unsubstituted $C_1$-$C_5$ alkyl. In embodiments, $R^7$ is unsubstituted ethyl. In embodiments, $R^7$ is methyl. In embodiments, $R^7$ is saturated or unsaturated unsubstituted $C_1$-$C_5$ alkyl. In embodiments, $R^7$ is unsaturated unsubstituted $C_1$-$C_5$ alkyl. In embodiments, $R^7$ is unsaturated unsubstituted $C_1$-$C_3$ alkyl. In embodiments, $R^7$ is propenyl.

Further to the compound of formula (I), in embodiments $L^1$ is substituted or unsubstituted $C_1$-$C_{10}$ alkylene. In embodiments, $L^1$ is unsubstituted $C_1$-$C_{10}$ alkylene. In embodiments, $L^1$ is $R^{L1}$-substituted $C_1$-$C_{10}$ alkylene. $R^{L1}$ may be independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $L^1$ is substituted or unsubstituted $C_1$-$C_5$ alkylene. In embodiments, $L^1$ is unsubstituted $C_1$-$C_5$ alkylene. In embodiments, $L^1$ is unsubstituted $C_1$-$C_3$ alkylene. In embodiments, $L^1$ is methylene or ethylene.

In embodiments, the compound has the formula:

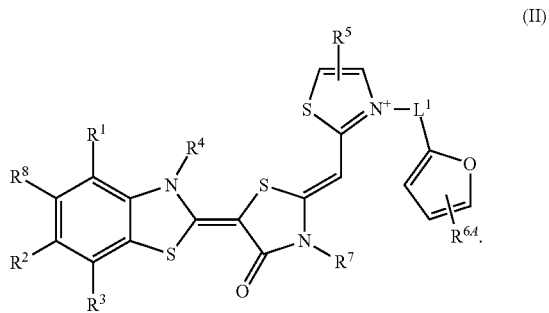

(II)

Regarding the compound of formula (II), substituents $R^1$, $R^2$, $R^3$, $R^4$, $R^5$, $R^{6A}$, $R^7$, $R^8$ and $L^1$ are as disclosed herein. For example, $R^1$, $R^2$, $R^3$, and $R^8$, are independently hydrogen, halogen or unsubstituted (e.g., $C_1$-$C_{20}$ or $C_1$-$C_6$) alkyl; $R^4$ is unsubstituted (e.g., $C_1$-$C_{20}$ or $C_1$-$C_6$) alkyl; $R^5$ is hydrogen, halogen or unsubstituted $C_1$-$C_5$ alkyl; $R^{6A}$ is substituted or unsubstituted $C_1$-$C_5$ alkyl, —$CX^f_3$, or —C(O)—$OR^{19}$ and $R^{19}$ is hydrogen or substituted or unsubstituted $C_1$-$C_5$ alkyl; $R^7$ is substituted or unsubstituted $C_1$-$C_5$ alkyl and $L^1$ is unsubstituted $C_1$-$C_{10}$ alkylene.

In embodiments, $R^1$, $R^2$, $R^3$, and $R^8$, are independently hydrogen, halogen or unsubstituted $C_1$-$C_6$ alkyl. In embodiments, $R^1$, $R^2$, $R^3$, and $R^8$, are independently hydrogen, halogen or unsubstituted $C_1$-$C_5$ alkyl. In embodiments, $R^1$, $R^2$, $R^3$, and $R^8$, are independently hydrogen, halogen or unsubstituted $C_1$-$C_4$ alkyl. In embodiments, $R^1$, $R^2$, $R^3$, and $R^8$, are independently hydrogen, halogen or unsubstituted $C_1$-$C_3$ alkyl. In embodiments, $R^1$, $R^2$, $R^3$, and $R^8$, are independently hydrogen or halogen. In embodiments, $R^1$, $R^3$, and $R^8$, are independently hydrogen and $R^2$ is halogen. In embodiments, $R^1$, $R^3$, and $R^8$, are independently hydrogen and $R^2$ is bromo.

In embodiments, $R^4$ is unsubstituted $C_1$-$C_6$ alkyl. In embodiments, $R^4$ is unsubstituted $C_1$-$C_5$ alkyl. In embodiments, $R^4$ is unsubstituted $C_1$-$C_4$ alkyl. In embodiments, $R^4$ is unsubstituted $C_1$-$C_3$ alkyl. In another further embodiment, $R^4$ is methyl.

In embodiments, $R^5$ is hydrogen or unsubstituted $C_1$-$C_5$ alkyl. In embodiments, $R^5$ is hydrogen or unsubstituted $C_1$-$C_4$ alkyl. In embodiments, $R^5$ is hydrogen or unsubstituted $C_1$-$C_3$ alkyl. In embodiments, $R^5$ is hydrogen.

In embodiments, $R^{6A}$ is —$CX^f_3$ or substituted or unsubstituted $C_1$-$C_5$ alkyl. In embodiments, $R^{6A}$ is $R^{6A}$-substituted or unsubstituted $C_1$-$C_5$ alkyl. In embodiments, $R^{6A}$ is $R^{6A}$-substituted or unsubstituted $C_1$-$C_4$ alkyl. In embodiments, $R^{6A}$ is $R^{6A}$-substituted or unsubstituted $C_1$-$C_3$ alkyl. In embodiments, $R^{6A}$ is trifluoromethyl.

In embodiments, $R^7$ is $R^{7A}$-substituted or unsubstituted $C_1$-$C_5$ alkyl and $R^{7A}$ is as described herein. In embodiments, $R^7$ is $R^{7A}$-substituted or unsubstituted $C_1$-$C_4$ alkyl and $R^{7A}$ is as described herein. In embodiments, $R^7$ is $R^{7A}$-substituted or unsubstituted $C_1$-$C_3$ alkyl and $R^{7A}$ is as described herein. In embodiments, $R^7$ is unsubstituted $C_1$-$C_5$ alkyl. In embodiments, $R^7$ is unsubstituted $C_1$-$C_4$ alkyl. In embodiments, $R^7$ is unsubstituted $C_1$-$C_3$ alkyl. In embodiments, $R^7$ is unsubstituted $C_1$-$C_3$ alkyl. In embodiments, $R^7$ is unsubstituted ethyl.

In embodiments, $L^1$ is unsubstituted $C_1$-$C_{10}$ alkylene. In embodiments, $L^1$ is unsubstituted $C_1$-$C_3$ alkylene. In embodiments, $L^1$ is unsubstituted $C_1$-$C_6$ alkylene. In embodiments, $L^1$ is unsubstituted $C_1$-$C_4$ alkylene. In embodiments, $L^1$ is unsubstituted ethylene.

In embodiments, $R^1$, $R^3$, and $R^8$, are hydrogen, $R^2$ is bromo, $R^4$ is methyl, $R^5$ is hydrogen, $R^{6A}$ is trifluoromethyl, $R^7$ is unsubstituted ethyl and $L^1$ is unsubstituted ethylene.

In embodiments, the compound has the formula:

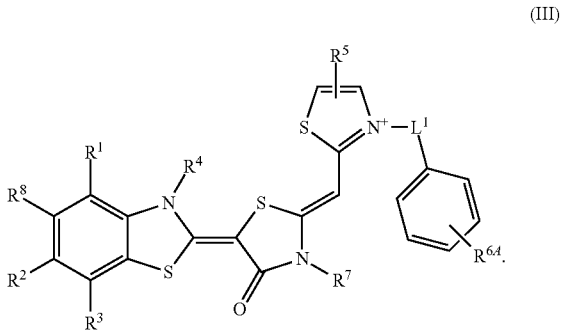

(III)

Regarding compound of formula (III), substituents $R^1$, $R^2$, $R^3$, $R^4$, $R^5$, $R^{6A}$, $R^7$, $R^8$ and $L^1$ are as disclosed herein. For example, $R^1$, $R^2$, $R^3$, and $R^8$, are independently hydrogen, halogen or unsubstituted (e.g., $C_1$-$C_{20}$ or $C_1$-$C_6$) alkyl; $R^4$ is unsubstituted (e.g., $C_1$-$C_{20}$ or $C_1$-$C_6$) alkyl; $R^5$ is hydrogen, halogen or unsubstituted $C_1$-$C_5$ alkyl; $R^{6A}$ is substituted or unsubstituted $C_1$-$C_5$ alkyl, or —C(O)—$OR^{19}$ and $R^{19}$ is hydrogen or substituted or unsubstituted $C_1$-$C_5$ alkyl; $R^7$ is substituted or unsubstituted $C_1$-$C_5$ alkyl and $L^1$ is unsubstituted $C_1$-$C_{10}$ alkylene.

In embodiments, $R^1$, $R^2$, $R^3$, and $R^8$, are independently hydrogen, halogen or unsubstituted $C_1$-$C_6$ alkyl. In embodiments, $R^1$, $R^2$, $R^3$, and $R^8$, are independently hydrogen, halogen or unsubstituted $C_1$-$C_5$ alkyl. In embodiments, $R^1$, $R^2$, $R^3$, and $R^8$, are independently hydrogen, halogen or unsubstituted $C_1$-$C_4$ alkyl. In embodiments, $R^1$, $R^2$, $R^3$, and $R^8$, are independently hydrogen, halogen or unsubstituted $C_1$-$C_3$ alkyl. In embodiments, $R^1$, $R^2$, $R^3$, and $R^8$, are independently hydrogen or unsubstituted $C_1$-$C_3$ alkyl. In embodiments, $R^1$, $R^3$, and $R^8$, are independently hydrogen and $R^2$ is unsubstituted $C_1$-$C_3$ alkyl. In embodiments, $R^1$, $R^3$, and $R^8$, are independently hydrogen and $R^2$ is ethyl.

In embodiments, $R^4$ is unsubstituted $C_1$-$C_6$ alkyl. In embodiments, $R^4$ is unsubstituted $C_1$-$C_5$ alkyl. In embodiments, $R^4$ is unsubstituted $C_1$-$C_4$ alkyl. In embodiments, $R^4$ is unsubstituted $C_1$-$C_3$ alkyl. In another further embodiment, $R^4$ is methyl.

In embodiments, $R^5$ is hydrogen or unsubstituted $C_1$-$C_5$ alkyl. In embodiments, $R^5$ is hydrogen or unsubstituted $C_1$-$C_4$ alkyl. In embodiments, $R^5$ is hydrogen or unsubstituted $C_1$-$C_3$ alkyl. In embodiments, $R^5$ is hydrogen.

In embodiments, $R^{6A}$ is —C(O)—OR$^{19}$ and $R^{19}$ is hydrogen or substituted or unsubstituted $C_1$-$C_5$ alkyl. In embodiments, $R^{19}$ is hydrogen. In embodiments, $R^{19}$ is unsubstituted $C_1$-$C_5$ alkyl. In embodiments, $R^{19}$ is unsubstituted $C_1$-$C_3$ alkyl. In embodiments, $R^{19}$ is methyl.

In embodiments, $R^7$ is $R^{7A}$-substituted or unsubstituted $C_1$-$C_5$ alkyl and $R^{7A}$ is as described herein. In embodiments, $R^7$ is $R^{7A}$-substituted or unsubstituted $C_1$-$C_4$ alkyl and $R^{7A}$ is as described herein. In embodiments, $R^7$ is $R^{7A}$-substituted or unsubstituted $C_1$-$C_3$ alkyl and $R^{7A}$ is as described herein. In embodiments, $R^7$ is unsubstituted $C_1$-$C_5$ alkyl. In embodiments, $R^7$ is unsubstituted $C_1$-$C_4$ alkyl. In embodiments, $R^7$ is unsubstituted $C_1$-$C_3$ alkyl. In embodiments, $R^7$ is unsubstituted $C_1$-$C_3$ alkyl. In embodiments, $R^7$ is unsubstituted ethyl.

In embodiments, $L^1$ is unsubstituted $C_1$-$C_{10}$ alkylene. In embodiments, $L^1$ is unsubstituted $C_1$-$C_5$ alkylene. In embodiments, $L^1$ is unsubstituted $C_1$-$C_6$ alkylene. In embodiments, $L^1$ is unsubstituted $C_1$-$C_4$ alkylene. In embodiments, $L^1$ is unsubstituted ethylene.

In embodiments, $R^1$, $R^3$, and $R^8$, are hydrogen, $R^2$ is ethyl, $R^4$ is methyl, $R^5$ is hydrogen, $R^{6A}$ is —C(O)—OR$^{19}$ and $R^{19}$ is methyl, $R^7$ is unsubstituted ethyl and $L^1$ is unsubstituted ethylene.

Pharmaceutical Compositions

In another aspect, there is provided a pharmaceutical composition including a pharmaceutically acceptable excipient and a compound of formula (I) as disclosed herein including embodiments thereof.

A. Formulations

The compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention, i.e., "pharmaceutical formulation."

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in PHARMACEUTICAL SCIENCES (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.01 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions provided by the present invention include compositions wherein the active ingredient is contained in a therapeutically effective amount. The actual amount effective for a particular application will depend, inter alia, on the condition being treated. For example, when administered in methods to treat infection, such compositions will contain an amount of active ingredient effective to achieve the desired result (e.g., to treat an infection).

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of eliciting innate immune response as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring effectiveness and adjusting the dosage upwards or downwards, as described above.

Dosages may be varied depending upon the requirements of the patient and the compound being employed. The dose administered to a patient, in the context of the present invention, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

Methods of Use

In another aspect, there is provided a method of treating a Hsp70-mediated disease in a patient in need of such treatment. The method includes administering a therapeutically effective amount of a compound of formula (I) as disclosed herein including embodiments thereof.

In embodiments, the disease is cancer, an infectious disease or a neurodegenerative disease. In embodiments, the disease is cancer. In embodiments, the disease is an infectious disease. In embodiments, the disease is a neurodegenerative disease.

In embodiments, the disease is cancer and the cancer is acute T cell leukemia, breast cancer, multiple myeloma, malignant melanoma, ovarian cancer, colorectal adenocarcinoma, endometrial cancer, cervical cancer or bladder cancer. In embodiments, the cancer is acute T cell leukemia. In embodiments, the cancer is breast cancer. In embodiments, the cancer is multiple myeloma. In embodiments, the cancer is malignant melanoma. In embodiments, the cancer is ovarian cancer. In embodiments, the cancer is colorectal adenocarcinoma. In embodiments, the cancer is endometrial cancer. In embodiments, the cancer is cervical cancer. In embodiments, the cancer is bladder cancer.

In embodiments, the disease is a neurodegenerative disease and the neurodegenerative disease is a polyglutamine expansion disorder. In embodiments, the polyglutamine expansion disorder is Kennedy's disease.

In embodiments, the disease is a neurodegenerative disease and the neurodegenerative disease is a tauopathy. The term "tauopathy" and the like refer, as usual and customary in the art, to a class of neurodegenerative diseases associate with the pathological aggregation of tau protein in the brain. Exemplary tauopathic diseases and disorders include Alzheimer's disease. In embodiments, the tauopathy is Alzheimer's disease.

In embodiments, the disease is an infectious disease, and the infectious disease is Dengue fever. In embodiments, the infectious disease is a Hepatitis C virus (HCV) disease. In embodiments, the infectious disease is influenza.

In another aspect, there is provided a method for inhibiting the activity of Hsp70 in a cell. The method includes contacting the cell with a compound of formula (I) as disclosed herein including embodiments thereof.

EXAMPLES

Compounds disclosed herein include the compound set forth in Table 1 following. The table provides the chemical structure, molecular weight and biological activities ($IC_{50}$) on binding to MCF-7, MDA-MB-231 and MFF (C57BL/6).

Cell viability was determined using a methyl thiazoyl tetrazolium (MTT) colorimetric assay (ATCC, catalog number 30-1010K) with the following modifications. Briefly, cells (5×103) were plated into 96-well assay plates in 0.1 ml media and allowed to attach overnight. Cells were then treated with compound at various concentrations in 0.2 mL media. After the 72-hour incubation period, cells were washed in PBS (3×100 μL), and 10 μL MTT reagent was added with 100 μL fresh media. Cells were then incubated for 4 hr in a humidified chamber at 37° C. with 5% CO2. Insoluble formazan crystals were solubilized by addition of 0.1 mL detergent solution (4 hr at room temp., dark). Resulting colored solutions were then quantified at an absorbance of 570 nm.

Synthesis Scheme.

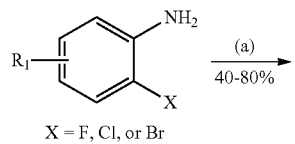

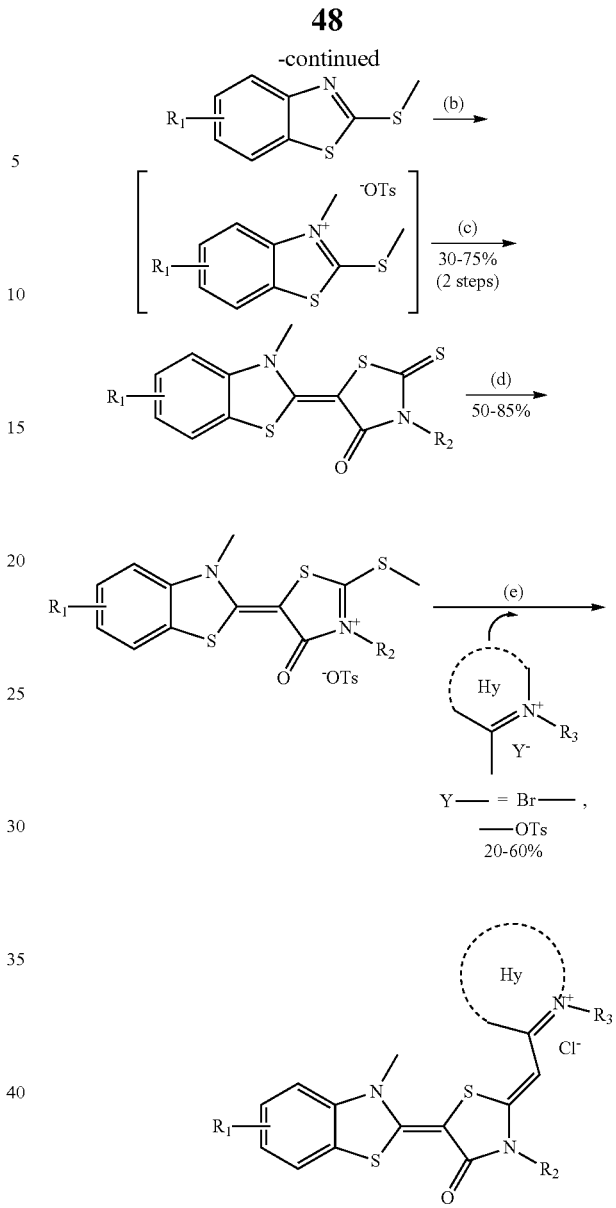

(a) 1. potassium ethyl xanthate, DMF, 4 h, 125° C.; 2. methyl iodide, triethylamine, ethanol, 1 h, 80° C. (b) methyl p-toluenesulfonate, anisole, 125° C.; (c) N-substituted rhodanine, triethylamine, acetonitrile, 4 h, 25° C.; (d) methyl p-toluenesulfonate, DMF, 3 h, 135° C.; (e) 1. triethlamine, acetonitrile, 3 h, 80° C., 2. Cl- ion exchange column.

TABLE 1

Chemical structure, molecule weights and biological activities of selected compounds.

| Compound | Structure | M.W. | $IC_{50}$/μM MCF-7 | $IC_{50}$/μM MDA-MB-231 | $IC_{50}$/μM MEF (C57BL/6) |
|---|---|---|---|---|---|
| JG-247 | 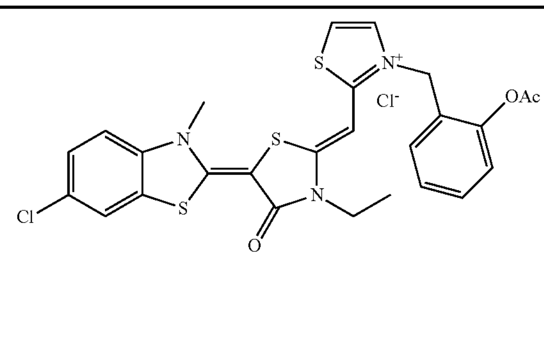 | 592.57 | 1.58 ± 0.18 | 1.8 ± 0.3 | 6.1 ± 0.3 |

TABLE 1-continued

Chemical structure, molecule weights and biological activities of selected compounds.

| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-248 | 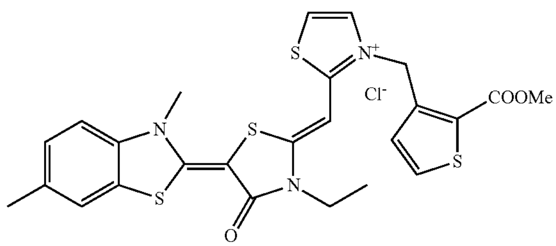 [SMILES: CCn1c(=O)/c(=C2\Sc3cc(C)ccc3N2C)s/c1=C\c1scc[n+]1Cc1ccsc1C(=O)OC ; [Cl-]] | 578.18 | 0.14 ± 0.01 | 0.11 ± 0.01 | 1.2 ± 0.2 |
| JG-249 | 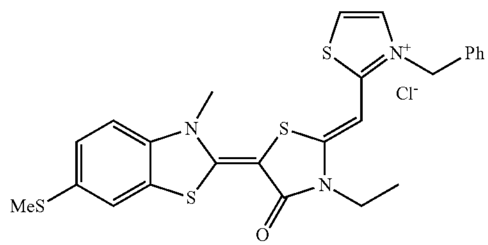 | 546.18 | 0.13 ± 0.01 | 0.12 ± 0.01 | 1.7 ± 0.1 |
| JG-250 | 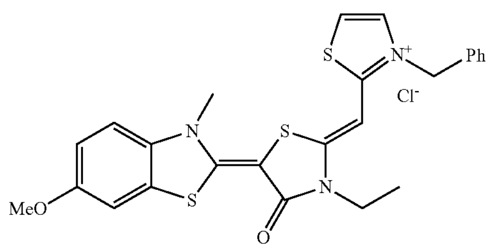 [SMILES: CCn1c(=O)/c(=C2\Sc3cc(SC)ccc3N2C)s/c1=C\c1scc[n+]1Cc1ccccc1 ; [Cl-]] | 530.12 | 0.13 ± 0.01 | 0.16 ± 0.01 | 2.0 ± 0.1 |
| JG-251 | 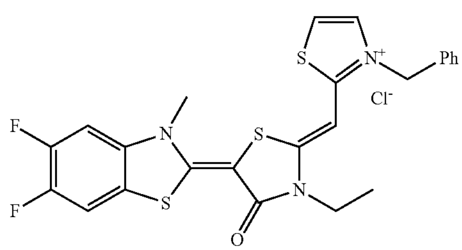 [SMILES: CCn1c(=O)/c(=C2\Sc3cc(F)c(F)cc3N2C)s/c1=C\c1scc[n+]1Cc1ccccc1 ; [Cl-]] | 535.04 | 2.5 ± 0.5 | 1.1 ± 0.1 | 0.91 ± 0.06 |
| JG-252 | 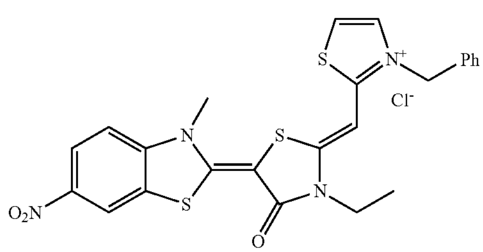 [SMILES: CCn1c(=O)/c(=C2\Sc3cc([N+](=O)[O-])ccc3N2C)s/c1=C\c1scc[n+]1Cc1ccccc1 ; [Cl-]] | 545.09 | >5 | 4.8 ± 0.4 | 2.8 ± 0.1 |
| JG-253 | 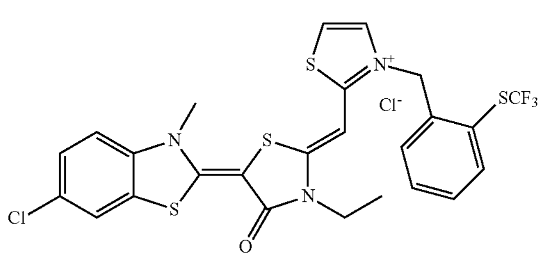 | 634.59 | 0.13 ± 0.01 | 0.16 ± 0.01 | 3.7 ± 0.2 |

TABLE 1-continued
Chemical structure, molecule weights and biological activities of selected compounds.
| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-254 | 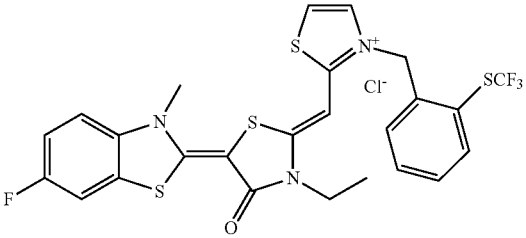 | 618.14 | 0.65 ± 0.13 | 0.10 ± 0.01 | 1.5 ± 0.1 |
| JG-255 | 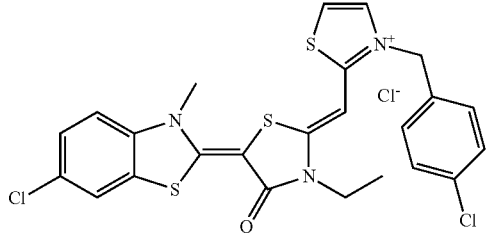 [SMILES: CCn1c(=O)/c(=C2\Sc3cc(Cl)ccc3N2C)s/c1=C\c1scc[n+]1Cc1ccc(Cl)cc1 ; [Cl-]] | 568.97 | 1.45 ± 0.13 | 0.41 ± 0.06 | 3.1 ± 0.3 |
| JG-256 | 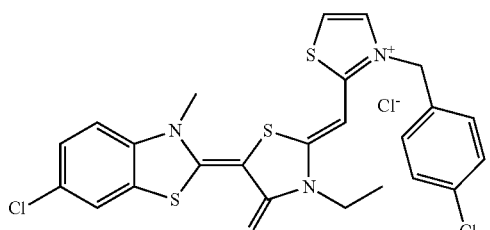 | 552.52 | 0.72 ± 0.06 | 1.1 ± 0.1 | 2.2 ± 0.1 |
| JG-257 | 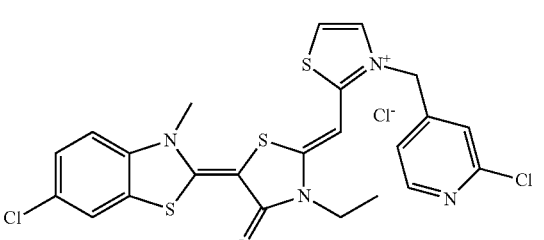 | 569.96 | >5 | 7.2 ± 0.8 | 1.1 ± 0.1 |
| JG-258 | 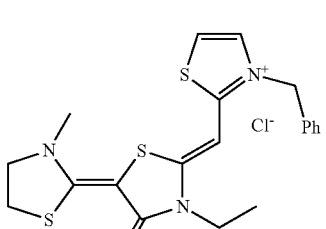 | 452.05 | >5 | >20 | >10 |
| JG-259 | 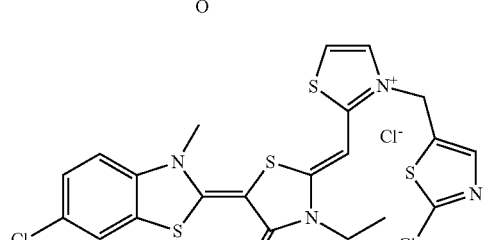 | 575.98 | >5 | 2.3 ± 0.3 | 8.9 ± 0.8 |

TABLE 1-continued

Chemical structure, molecule weights and biological activities of selected compounds.

| Compound | Structure | M.W. | IC$_{50}$/μM MCF-7 | IC$_{50}$/μM MDA-MB-231 | IC$_{50}$/μM MEF (C57BL/6) |
| --- | --- | --- | --- | --- | --- |
| JG-260 | 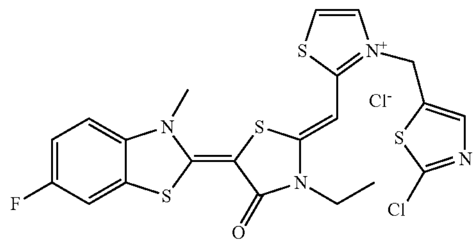 [SMILES: CCn1c(=O)/c(=C2\Sc3cc(F)ccc3N2C)s/c1=C\c1scc[n+]1Cc1cnc(Cl)s1 ; [Cl-]] | 559.53 | >5 | 6.7 ± 0.5 | 8.2 ± 0.4 |
| JG-261 | 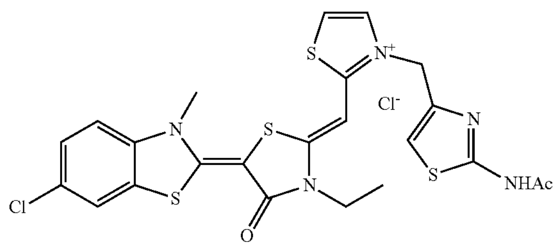 [SMILES: CCn1c(=O)/c(=C2\Sc3cc(Cl)ccc3N2C)s/c1=C\c1scc[n+]1Cc1csc(NC(C)=O)n1 ; [Cl-]] | 598.59 | >5 | >20 | 4.2 ± 0.6 |
| JG-262 | 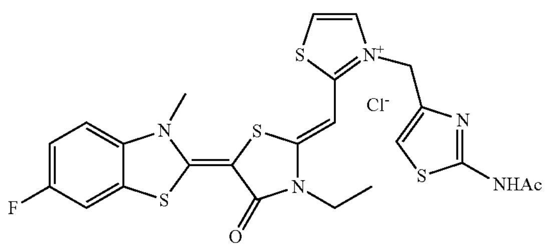 [SMILES: CCn1c(=O)/c(=C2\Sc3cc(F)ccc3N2C)s/c1=C\c1scc[n+]1Cc1csc(NC(C)=O)n1 ; [Cl-]] | 582.14 | >5 | >20 | >10 |
| JG-263 | 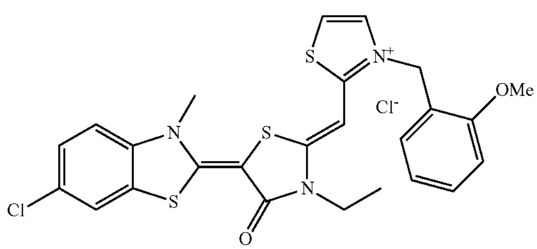 [SMILES: CCn1c(=O)/c(=C2\Sc3cc(Cl)ccc3N2C)s/c1=C\c1scc[n+]1Cc1ccccc1OC ; [Cl-]] | 564.56 | 0.40 ± 0.03 | 0.12 ± 0.01 | 1.5 ± 0.1 |
| JG-264 | 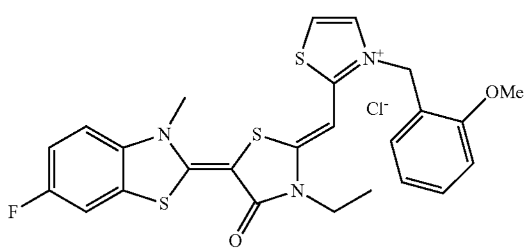 [SMILES: CCn1c(=O)/c(=C2\Sc3cc(F)ccc3N2C)s/c1=C\c1scc[n+]1Cc1ccccc1OC ; [Cl-]] | 548.11 | 0.49 ± 0.04 | 0.24 ± 0.03 | 1.4 ± 0.1 |
| JG-265 | 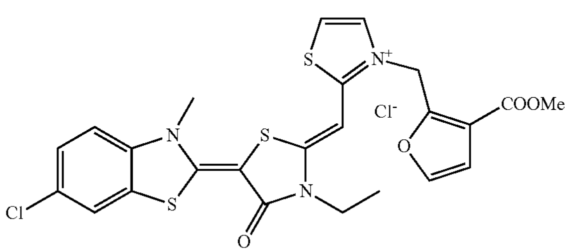 [SMILES: CCn1c(=O)/c(=C2\Sc3cc(Cl)ccc3N2C)s/c1=C\c1scc[n+]1Cc1occc1C(=O)OC ; [Cl-]] | 582.53 | 0.81 ± 0.09 | 0.13 ± 0.01 | 2.7 ± 0.1 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
|---|---|---|---|---|---|
| JG-266 | 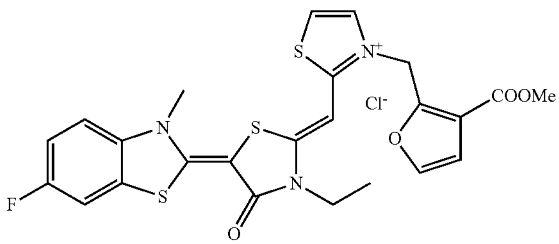 [SMILES: CCn1c(=O)/c(=C2\Sc3cc(F)ccc3N2C)s/c1=C\c1scc[n+]1Cc1occc1C(=O)OC ; [Cl-]] | 566.08 | 0.87 ± 0.11 | 0.30 ± 0.02 | 2.7 ± 0.2 |
| JG-267 | 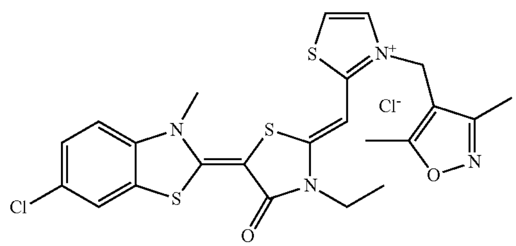 [SMILES: CCn1c(=O)/c(=C2\Sc3cc(Cl)ccc3N2C)s/c1=C\c1scc[n+]1Cc1c(C)noc1C ; [Cl-]] | 553.53 | >5 | 10 ± 2 | 7.6 ± 0.3 |
| JG-268 | 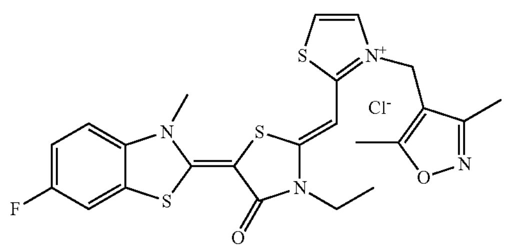 [SMILES: CCn1c(=O)/c(=C2\Sc3cc(F)ccc3N2C)s/c1=C\c1scc[n+]1Cc1c(C)noc1C ; [Cl-]] | 537.08 | >5 | >20 | >10 |
| JG-269 | 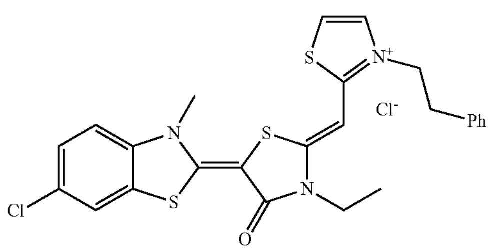 [SMILES: CCn1c(=O)/c(=C2\Sc3cc(Cl)ccc3N2C)s/c1=C\c1scc[n+]1CCc1ccccc1 ; [Cl-]] | 548.56 | 0.18 ± 0.01 | 0.26 ± 0.04 | 2.2 ± 0.1 |
| JG-270 | 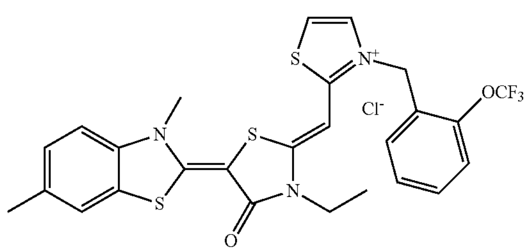 [SMILES: CCn1c(=O)/c(=C2\Sc3cc(C)ccc3N2C)s/c1=C\c1scc[n+]1Cc1ccccc1OC(F)(F)F ; [Cl-]] | 598.11 | 0.064 ± 0.005 | 0.077 ± 0.009 | 0.75 ± 0.05 |
| JG-271 | 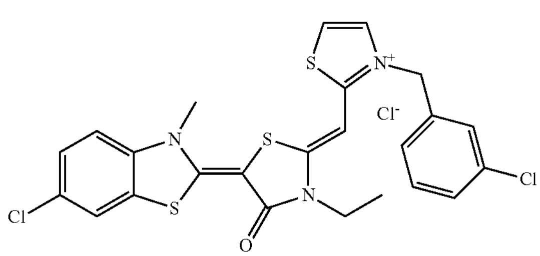 [SMILES: CCn1c(=O)/c(=C2\Sc3cc(Cl)ccc3N2C)s/c1=C\c1scc[n+]1Cc1cccc(Cl)c1 ; [Cl-]] | 568.97 | 0.26 ± 0.02 | 0.51 ± 0.06 | 0.69 ± 0.03 |

TABLE 1-continued

Chemical structure, molecule weights and biological activities of selected compounds.

| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-272 | 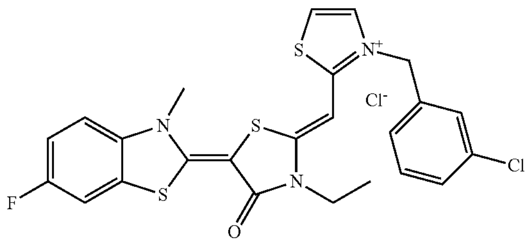 [SMILES: CCn1c(=O)/c(=C2\Sc3cc(F)ccc3N2C)s/c1=C\c1scc[n+]1Cc1cccc(Cl)c1 ; [Cl-]] | 552.52 | 0.36 ± 0.02 | 0.77 ± 0.10 | 0.62 ± 0.03 |
| JG-273 | 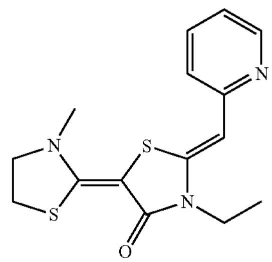 [SMILES: CCn1c(=O)/c(=C2\SCCN2C)s/c1=C\c1ccccn1] | 319.44 | >5 | >20 | >10 |
| JG-274 | 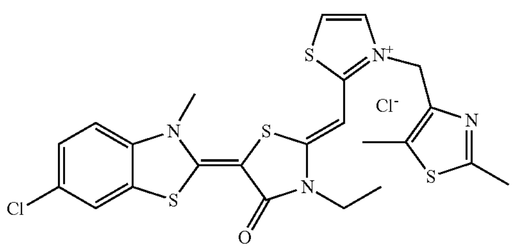 [SMILES: CCn1c(=O)/c(=C2\Sc3cc(Cl)ccc3N2C)s/c1=C\c1scc[n+]1Cc1nc(C)sc1C ; [Cl-]] | 568.61 | 0.098 ± 0.008 | 0.080 ± 0.008 | 4.2 ± 0.4 |
| JG-275 | 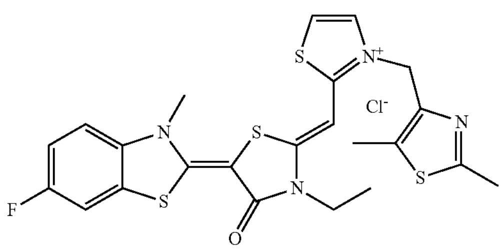 [SMILES: CCn1c(=O)/c(=C2\Sc3cc(F)ccc3N2C)s/c1=C\c1scc[n+]1Cc1nc(C)sc1C ; [Cl-]] | 552.16 | 0.27 ± 0.03 | 0.30 ± 0.03 | 1.6 ± 0.1 |
| JG-276 | 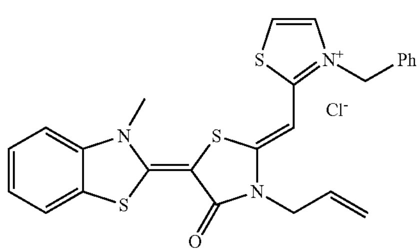 [SMILES: C=CCn1c(=O)/c(=C2\Sc3ccccc3N2C)s/c1=C\c1scc[n+]1Cc1ccccc1 ; [Cl-]] | 512.10 | 0.24 ± 0.02 | 0.27 ± 0.03 | 2.5 ± 0.1 |
| JG-277 | 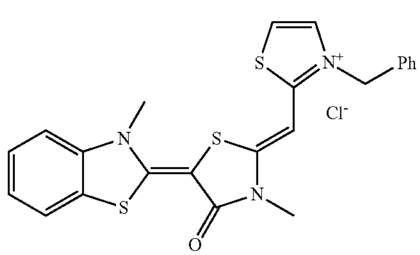 [SMILES: CN1/C(=c2\s/c(=C\c3scc[n+]3Cc3ccccc3)n(C)c2=O)Sc2ccccc21 ; [Cl-]] | 486.06 | 0.39 ± 0.03 | 0.49 ± 0.05 | 4.1 ± 0.2 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
| --- | --- | --- | --- | --- | --- |
| JG-278 | 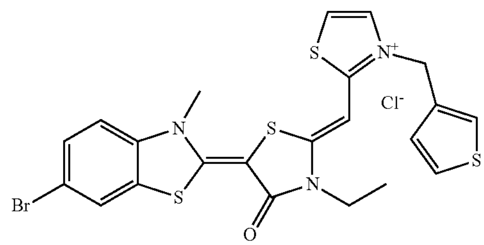 [SMILES: CCn1c(=O)/c(=C2\Sc3cc(Br)ccc3N2C)s/c1=C\c1scc[n+]1Cc1ccsc1 ; [Cl-]] | 585.01 | 0.39 ± 0.06 | 0.23 ± 0.04 | 3.4 ± 0.2 |
| JG-279 | 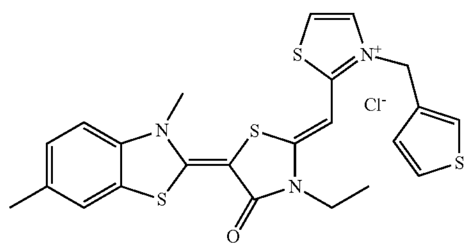 [SMILES: CCn1c(=O)/c(=C2\Sc3cc(C)ccc3N2C)s/c1=C\c1scc[n+]1Cc1ccsc1 ; [Cl-]] | 520.14 | 0.14 ± 0.03 | 0.15 ± 0.01 | 2.2 ± 0.1 |
| JG-280 | 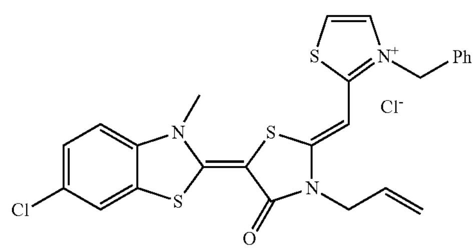 [SMILES: C=CCn1c(=O)/c(=C2\Sc3cc(Cl)ccc3N2C)s/c1=C\c1scc[n+]1Cc1ccccc1 ; [Cl-]] | 546.54 | 0.17 ± 0.02 | 0.10 ± 0.01 | 2.4 ± 0.1 |
| JG-281 | 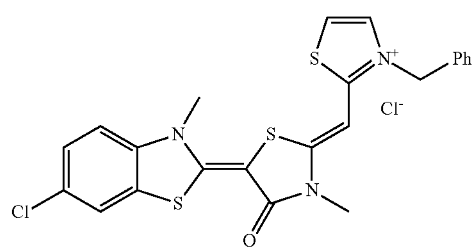 [SMILES: CN1/C(=c2\s/c(=C\c3scc[n+]3Cc3ccccc3)n(C)c2=O)Sc2cc(Cl)ccc21 ; [Cl-]] | 520.50 | 0.60 ± 0.06 | 0.16 ± 0.02 | 5.7 ± 0.3 |
| JG-282 | 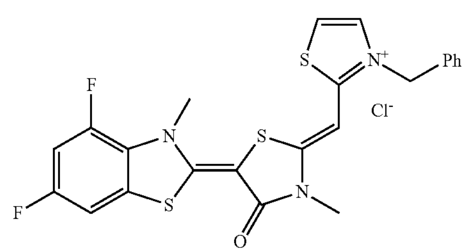 [SMILES: CN1/C(=c2\s/c(=C\c3scc[n+]3Cc3ccccc3)n(C)c2=O)Sc2cc(F)cc(F)c21 ; [Cl-]] | 536.07 | 0.29 ± 0.04 | 0.26 ± 0.03 | 2.5 ± 0.1 |
| JG-283 | 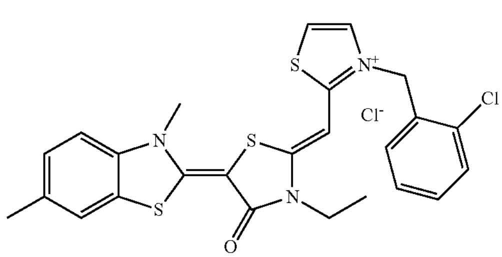 [SMILES: CCn1c(=O)/c(=C2\Sc3cc(C)ccc3N2C)s/c1=C\c1scc[n+]1Cc1ccccc1Cl ; [Cl-]] | 548.56 | 0.063 ± 0.007 | 0.088 ± 0.005 | 0.45 ± 0.02 |

TABLE 1-continued

Chemical structure, molecule weights and biological activities of selected compounds.

| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-284 | 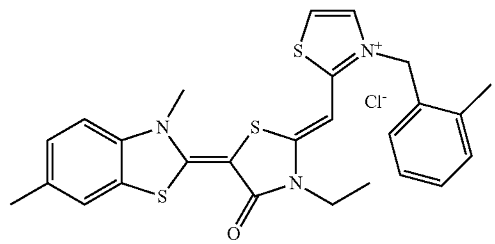 | 528.14 | 0.090 ± 0.006 | 0.090 ± 0.005 | 0.64 ± 0.03 |
| JG-285 | 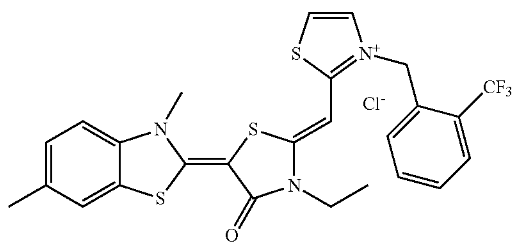 [SMILES: CCn1c(=O)/c(=C2\Sc3cc(C)ccc3N2C)s/c1=C\c1scc[n+]1Cc1ccccc1C(F)(F)F ; [Cl-]] | 582.11 | 0.078 ± 0.003 | 0.062 ± 0.010 | 0.66 ± 0.06 |
| JG-286 | 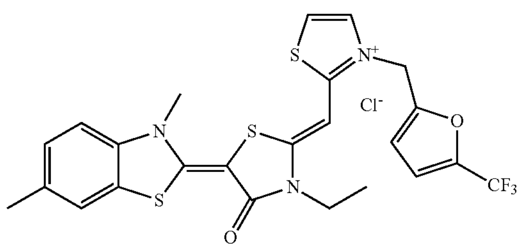 [SMILES: CCn1c(=O)/c(=C2\Sc3cc(C)ccc3N2C)s/c1=C\c1scc[n+]1Cc1ccc(C(F)(F)F)o1 ; [Cl-]] | 572.08 | 0.27 ± 0.02 | 0.14 ± 0.01 | 5.0 ± 0.6 |
| JG-287 | 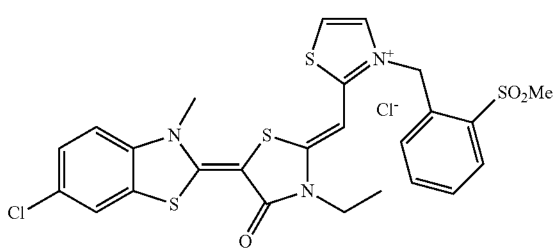 [SMILES: CCn1c(=O)/c(=C2\Sc3cc(Cl)ccc3N2C)s/c1=C\c1scc[n+]1Cc1ccccc1S(C)(=O)=O ; [Cl-]] | 612.62 | 1.73 ± 0.20 | 1.3 ± 0.3 | >10 |
| JG-288 | 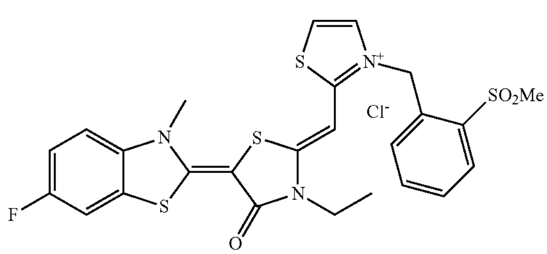 [SMILES: CCn1c(=O)/c(=C2\Sc3cc(F)ccc3N2C)s/c1=C\c1scc[n+]1Cc1ccccc1S(C)(=O)=O ; [Cl-]] | 596.16 | 1.97 ± 0.11 | 0.64 ± 0.08 | >10 |
| JG-289 | 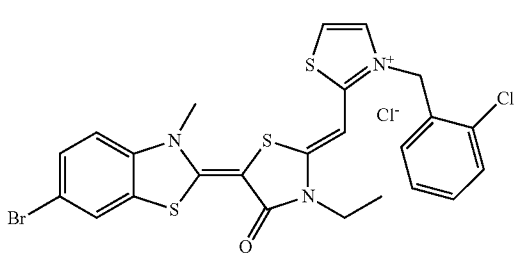 | 613.43 | 0.27 ± 0.02 | 0.12 ± 0.02 | 0.96 ± 0.05 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
| --- | --- | --- | --- | --- | --- |
| JG-290 | 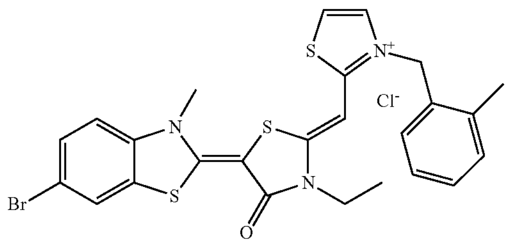 [SMILES: CCn1c(=O)/c(=C2\Sc3cc(Br)ccc3N2C)s/c1=C\c1scc[n+]1Cc1ccccc1C ; [Cl-]] | 593.01 | 0.16 ± 0.01 | 0.21 ± 0.02 | 1.7 ± 0.1 |
| JG-291 | 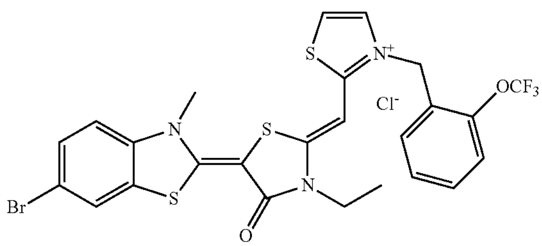 | 662.98 | 0.14 ± 0.01 | 0.14 ± 0.01 | 2.3 ± 0.1 |
| JG-292 | 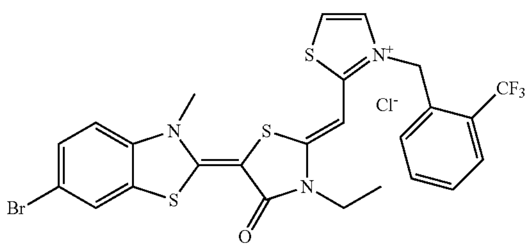 | 646.98 | 0.12 ± 0.01 | 0.18 ± 0.02 | 2.7 ± 0.1 |
| JG-293 | 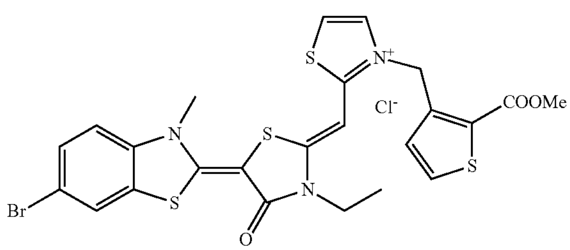 | 643.04 | 0.30 ± 0.03 | 0.14 ± 0.03 | 3.1 ± 0.3 |
| JG-294 | 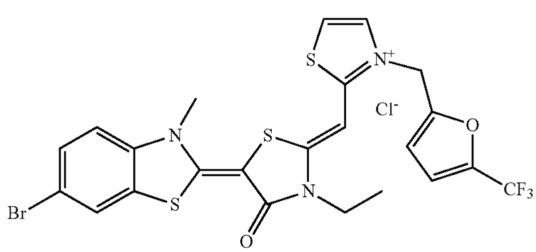 | 636.94 | 0.10 ± 0.01 | 0.18 ± 0.01 | 3.5 ± 0.4 |
| JG-295 | 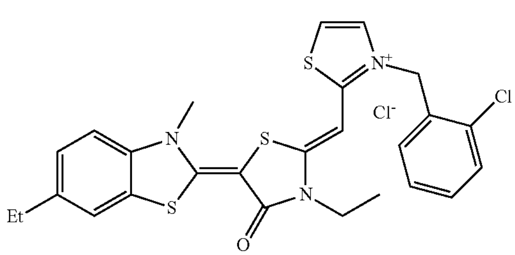 [SMILES: CCc1ccc2c(c1)S/C(=c1/s/c(=C\c3scc[n+]3Cc3ccccc3Cl)n(CC)c1=O)N2C ; [Cl-]] | 562.59 | 0.084 ± 0.006 | 0.093 ± 0.005 | 0.48 ± 0.01 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
|---|---|---|---|---|---|
| JG-296 | 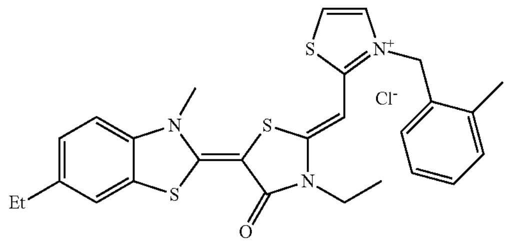 [SMILES: CCc1ccc2c(c1)S/C(=c1/s/c(=C\c3scc[n+]3Cc3ccccc3C)n(CC)c1=O)N2C ; [Cl-]] | 542.17 | 0.10 ± 0.01 | 0.14 ± 0.01 | 0.61 ± 0.02 |
| JG-297 | 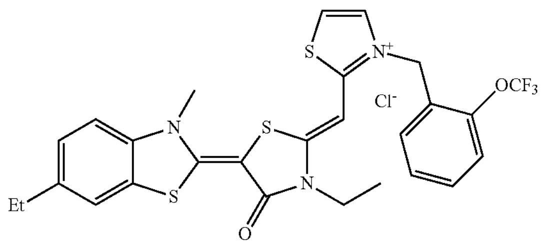 [SMILES: CCc1ccc2c(c1)S/C(=c1/s/c(=C\c3scc[n+]3Cc3ccccc3OC(F)(F)F)n(CC)c1=O)N2C ; [Cl-]] | 612.14 | 0.080 ± 0.005 | 0.097 ± 0.006 | 0.41 ± 0.01 |
| JG-298 | 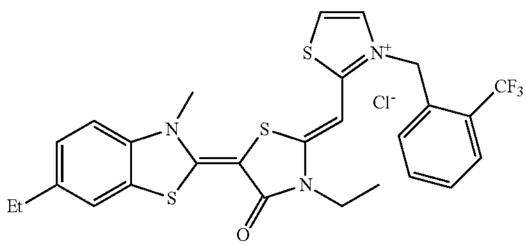 [SMILES: CCc1ccc2c(c1)S/C(=c1/s/c(=C\c3scc[n+]3Cc3ccccc3C(F)(F)F)n(CC)c1=O)N2C ; [Cl-]] | 596.14 | 0.052 ± 0.004 | 0.11 ± 0.01 | 0.43 ± 0.02 |
| JG-299 | 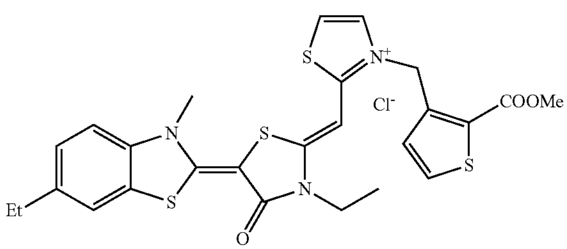 [SMILES: CCc1ccc2c(c1)S/C(=c1/s/c(=C\c3scc[n+]3Cc3ccsc3C(=O)OC)n(CC)c1=O)N2C ; [Cl-]] | 592.20 | 0.083 ± 0.007 | 0.071 ± 0.009 | 0.92 ± 0.04 |
| JG-300 | 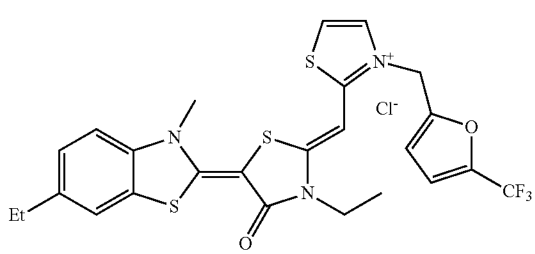 [SMILES: CCc1ccc2c(c1)S/C(=c1/s/c(=C\c3scc[n+]3Cc3ccc(C(F)(F)F)o3)n(CC)c1=O)N2C ; [Cl-]] | 586.10 | 0.11 ± 0.01 | 0.10 ± 0.01 | 1.4 ± 0.06 |
| JG-301 | 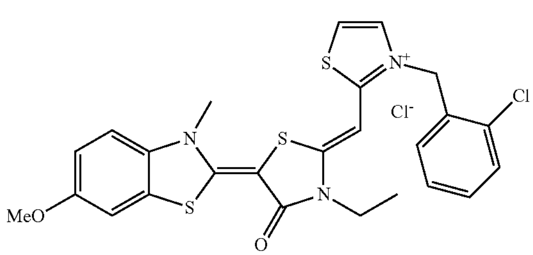 [SMILES: CCn1c(=O)/c(=C2\Sc3cc(OC)ccc3N2C)s/c1=C\c1scc[n+]1Cc1ccccc1Cl ; [Cl-]] | 564.56 | 0.048 ± 0.003 | 0.033 ± 0.005 | 0.66 ± 0.01 |

TABLE 1-continued

Chemical structure, molecule weights and biological activities of selected compounds.

| Compound | Structure | M.W. | IC$_{50}$/μM MCF-7 | IC$_{50}$/μM MDA-MB-231 | IC$_{50}$/μM MEF (C57BL/6) |
| --- | --- | --- | --- | --- | --- |
| JG-302 | 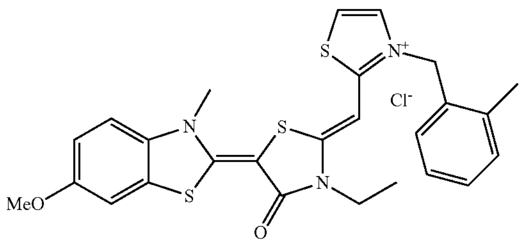 | 544.13 | 0.12 ± 0.01 | 0.11 ± 0.01 | 1.8 ± 0.05 |
| JG-303 | 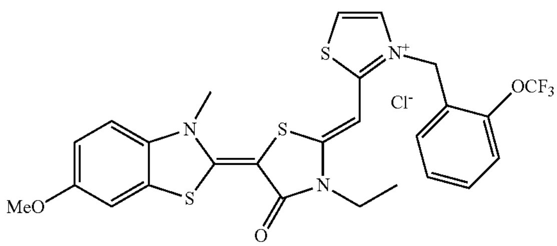 | 614.11 | 0.070 ± 0.003 | 0.053 ± 0.005 | 0.70 ± 0.01 |
| JG-304 | 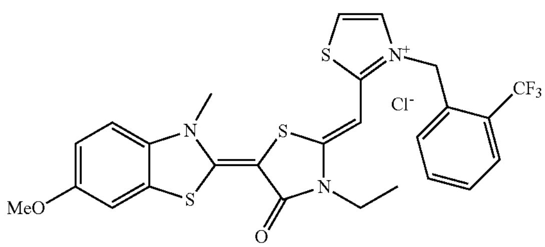 [SMILES: CCn1c(=O)/c(=C2\Sc3cc(OC)ccc3N2C)s/c1=C\c1scc[n+]1Cc1ccccc1C(F)(F)F ; [Cl-]] | 598.11 | 0.12 ± 0.01 | 0.10 ± 0.02 | 1.4 ± 0.06 |
| JG-305 | 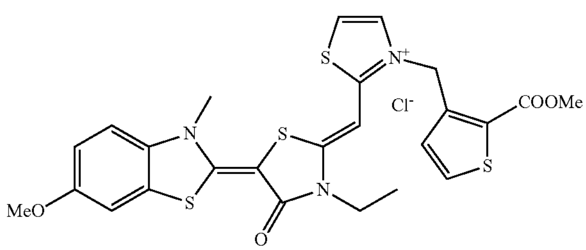 | 594.17 | 0.12 ± 0.01 | 0.16 ± 0.01 | 1.0 ± 0.1 |
| JG-306 | 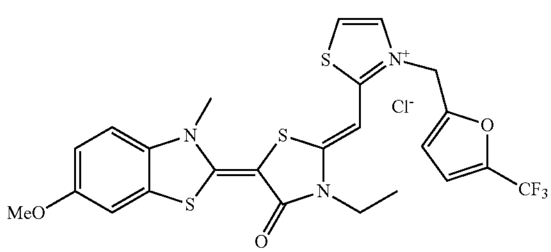 | 588.08 | 0.16 ± 0.02 | 0.10 ± 0.01 | >10 |
| JG-307 | 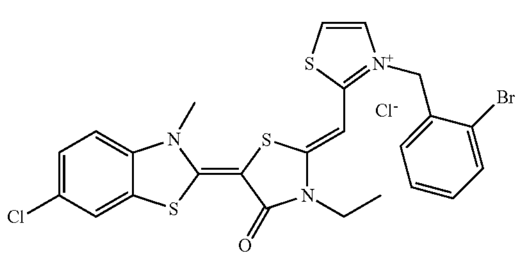 [SMILES: CCn1c(=O)/c(=C2\Sc3cc(Cl)ccc3N2C)s/c1=C\c1scc[n+]1Cc1ccccc1Br ; [Cl-]] | 613.43 | 0.12 ± 0.01 | 0.13 ± 0.02 | 1.1 ± 0.1 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
| --- | --- | --- | --- | --- | --- |
| JG-308 | 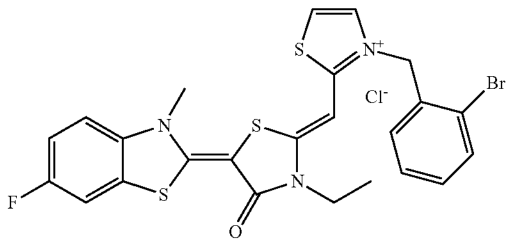 [SMILES: CCn1c(=O)/c(=C2\Sc3cc(F)ccc3N2C)s/c1=C\c1scc[n+]1Cc1ccccc1Br ; [Cl-]] | 596.98 | 0.16 ± 0.02 | 0.19 ± 0.02 | 0.60 ± 0.06 |
| JG-309 | 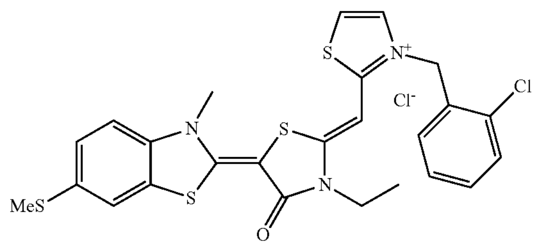 [SMILES: CCn1c(=O)/c(=C2\Sc3cc(SC)ccc3N2C)s/c1=C\c1scc[n+]1Cc1ccccc1Cl ; [Cl-]] | 580.62 | 0.15 ± 0.01 | 0.13 ± 0.01 | 0.75 ± 0.05 |
| JG-310 | 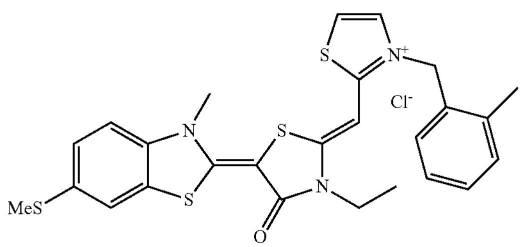 [SMILES: CCn1c(=O)/c(=C2\Sc3cc(SC)ccc3N2C)s/c1=C\c1scc[n+]1Cc1ccccc1C ; [Cl-]] | 560.20 | 0.23 ± 0.04 | 0.11 ± 0.01 | 2.2 ± 0.2 |
| JG-311 | 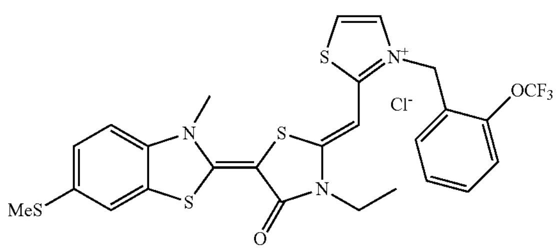 [SMILES: CCn1c(=O)/c(=C2\Sc3cc(SC)ccc3N2C)s/c1=C\c1scc[n+]1Cc1ccccc1OC(F)(F)F ; [Cl-]] | 630.17 | 0.098 ± 0.009 | 0.14 ± 0.01 | 2.0 ± 0.1 |
| JG-312 | 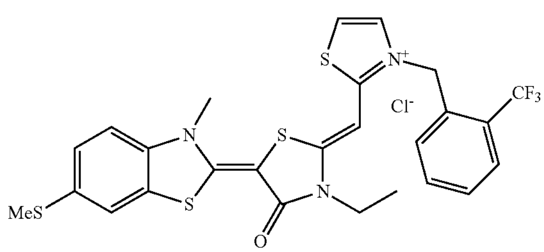 [SMILES: CCn1c(=O)/c(=C2\Sc3cc(SC)ccc3N2C)s/c1=C\c1scc[n+]1Cc1ccccc1C(F)(F)F ; [Cl-]] | 614.18 | 0.10 ± 0.01 | 0.14 ± 0.01 | 3.2 ± 0.2 |
| JG-313 | 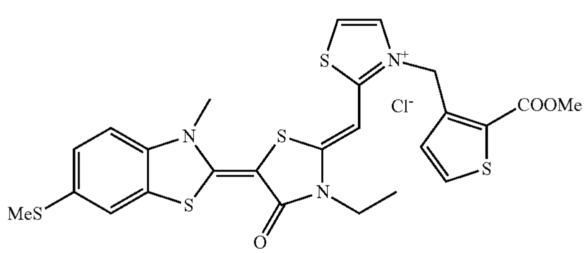 [SMILES: CCn1c(=O)/c(=C2\Sc3cc(SC)ccc3N2C)s/c1=C\c1scc[n+]1Cc1ccsc1C(=O)OC ; [Cl-]] | 610.24 | 0.20 ± 0.01 | 0.16 ± 0.02 | 1.4 ± 0.1 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
|---|---|---|---|---|---|
| JG-314 | 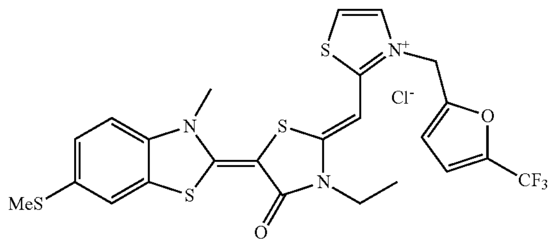 [SMILES: CCn1c(=O)/c(=C2\Sc3cc(SC)ccc3N2C)s/c1=C\c1scc[n+]1Cc1ccc(C(F)(F)F)o1 ; [Cl-]] | 604.14 | 0.57 ± 0.08 | 0.25 ± 0.04 | 4.8 ± 0.9 |
| JG-315 | 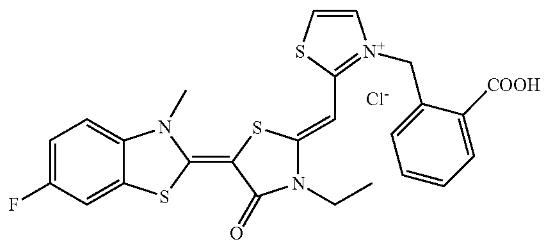 [SMILES: CCn1c(=O)/c(=C2\Sc3cc(F)ccc3N2C)s/c1=C\c1scc[n+]1Cc1ccccc1C(=O)O ; [Cl-]] | 562.09 | >20 | >20 | >10 |
| JG-316 | 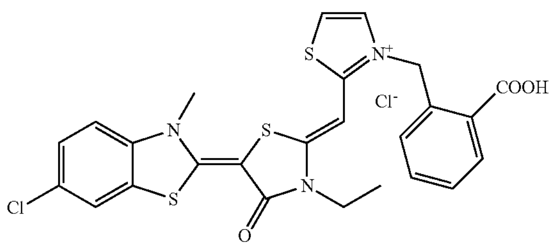 [SMILES: CCn1c(=O)/c(=C2\Sc3cc(Cl)ccc3N2C)s/c1=C\c1scc[n+]1Cc1ccccc1C(=O)O ; [Cl-]] | 578.54 | >20 | >20 | >10 |
| JG-317 | 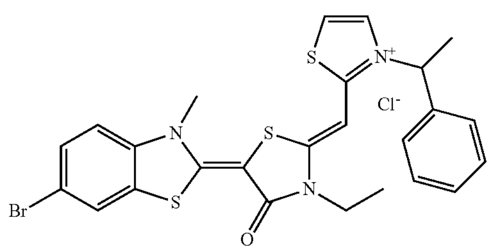 | 593.01 | 0.35 ± 0.08 | 0.14 ± 0.02 | 2.7 ± 0.1 |
| JG-318 | 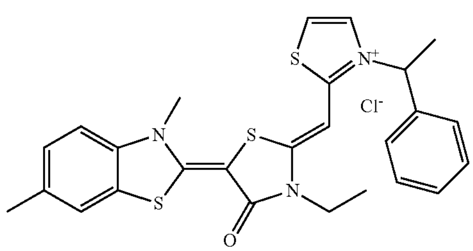 [SMILES: CCn1c(=O)/c(=C2\Sc3cc(C)ccc3N2C)s/c1=C\c1scc[n+]1C(C)c1ccccc1 ; [Cl-]] | 528.14 | 0.16 ± 0.03 | 0.11 ± 0.01 | 1.1 ± 0.1 |
| JG-319 | 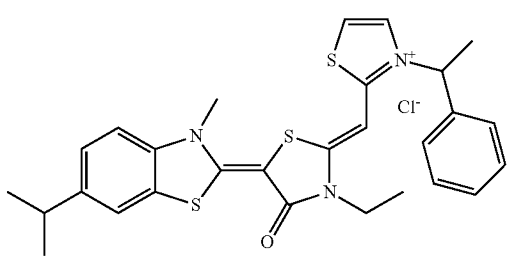 [SMILES: CCn1c(=O)/c(=C2\Sc3cc(C(C)C)ccc3N2C)s/c1=C\c1scc[n+]1C(C)c1ccccc1 ; [Cl-]] | 556.20 | 0.13 ± 0.01 | 0.26 ± 0.03 | 1.7 ± 0.04 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
|---|---|---|---|---|---|
| JG-320 | 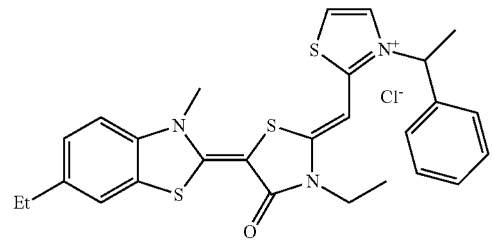 [SMILES: CCc1ccc2c(c1)S/C(=c1/s/c(=C\c3scc[n+]3C(C)c3ccccc3)n(CC)c1=O)N2C ; [Cl-]] | 542.17 | 0.10 ± 0.01 | 0.30 ± 0.05 | 1.3 ± 0.04 |
| JG-321 | 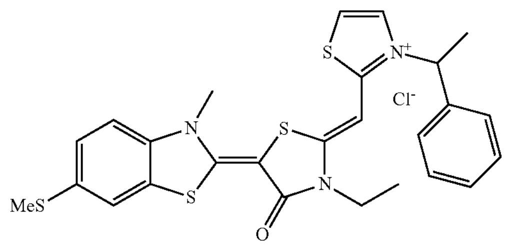 [SMILES: CCn1c(=O)/c(=C2\Sc3cc(SC)ccc3N2C)s/c1=C\c1scc[n+]1C(C)c1ccccc1 ; [Cl-]] | 560.20 | 0.23 ± 0.03 | 0.14 ± 0.01 | 1.8 ± 0.1 |
| JG-322 | 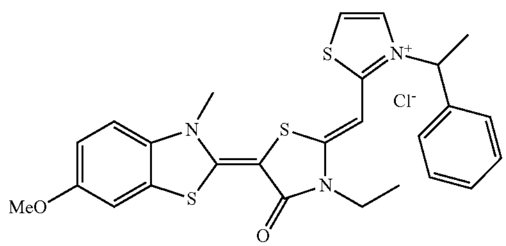 [SMILES: CCn1c(=O)/c(=C2\Sc3cc(OC)ccc3N2C)s/c1=C\c1scc[n+]1C(C)c1ccccc1 ; [Cl-]] | 544.14 | 0.14 ± 0.01 | 0.15 ± 0.01 | 1.7 ± 0.1 |
| JG-323 | 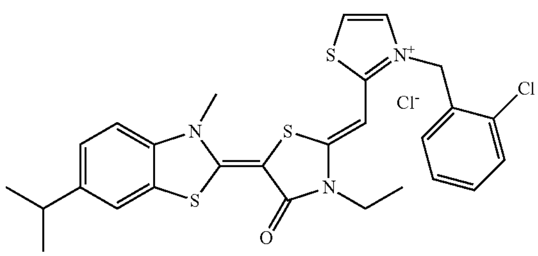 [SMILES: CCn1c(=O)/c(=C2\Sc3cc(C(C)C)ccc3N2C)s/c1=C\c1scc[n+]1Cc1ccccc1Cl ; [Cl-]] | 576.61 | 0.12 ± 0.01 | 0.19 ± 0.01 | 0.53 ± 0.02 |
| JG-324 | 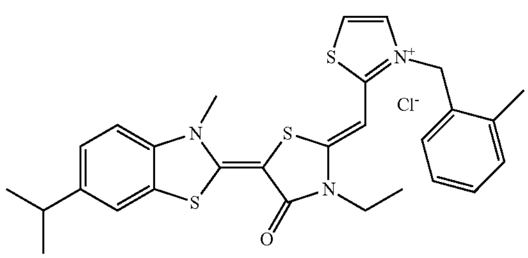 [SMILES: CCn1c(=O)/c(=C2\Sc3cc(C(C)C)ccc3N2C)s/c1=C\c1scc[n+]1Cc1ccccc1C ; [Cl-]] | 556.20 | 0.17 ± 0.02 | 0.15 ± 0.02 | 1.9 ± 0.1 |
| JG-325 | 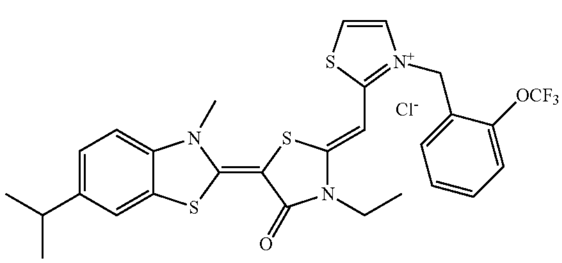 [SMILES: CCn1c(=O)/c(=C2\Sc3cc(C(C)C)ccc3N2C)s/c1=C\c1scc[n+]1Cc1ccccc1OC(F)(F)F ; [Cl-]] | 626.17 | 0.090 ± 0.005 | 0.21 ± 0.01 | 0.48 ± 0.02 |

TABLE 1-continued
Chemical structure, molecule weights and biological activities of selected compounds.
| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-326 | 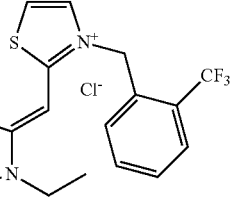 | 610.17 | 0.069 ± 0.005 | 0.060 ± 0.007 | 0.45 ± 0.04 |
| JG-327 | 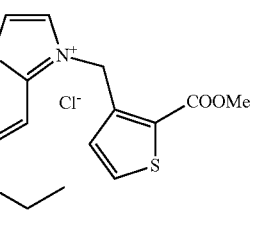 | 606.23 | 0.15 ± 0.02 | 0.17 ± 0.02 | 0.70 ± 0.03 |
| JG-328 | 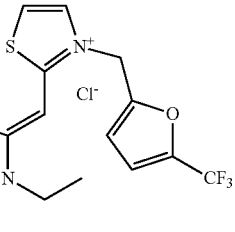 | 600.13 | 0.14 ± 0.02 | 0.23 ± 0.02 | 0.70 ± 0.03 |
| JG-329 | 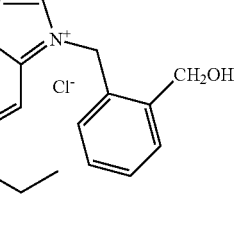 | 564.56 | 0.58 ± 0.10 | 0.39 ± 0.06 | 7.3 ± 2.1 |
| JG-330 | 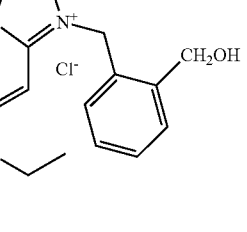 | 548.11 | 1.08 ± 0.14 | 1.93 ± 0.27 | >10 |
| JG-331 | 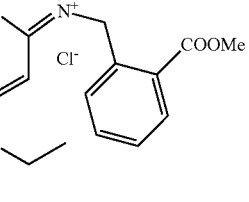 | 592.57 | 0.17 ± 0.02 | 0.17 ± 0.02 | 2.9 ± 0.1 |

TABLE 1-continued
Chemical structure, molecule weights and biological activities of selected compounds.
| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-332 | 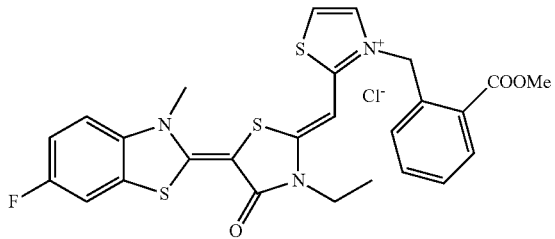 [SMILES: CCn1c(=O)/c(=C2\Sc3cc(F)ccc3N2C)s/c1=C\c1scc[n+]1Cc1ccccc1C(=O)OC ; [Cl-]] | 576.12 | 0.22 ± 0.03 | 0.26 ± 0.03 | 2.0 ± 0.1 |
| JG-333 | 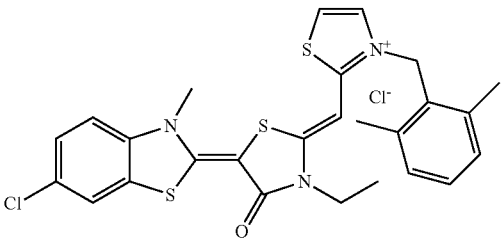 [SMILES: CCn1c(=O)/c(=C2\Sc3cc(Cl)ccc3N2C)s/c1=C\c1scc[n+]1Cc1c(C)cccc1C ; [Cl-]] | 562.59 | 0.35 ± 0.04 | 0.19 ± 0.02 | 1.1 ± 0.1 |
| JG-334 | 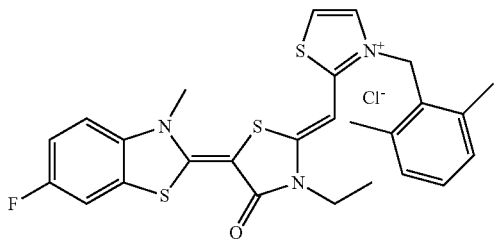 [SMILES: CCn1c(=O)/c(=C2\Sc3cc(F)ccc3N2C)s/c1=C\c1scc[n+]1Cc1c(C)cccc1C ; [Cl-]] | 546.13 | 0.32 ± 0.03 | 0.38 ± 0.04 | 1.4 ± 0.1 |
| JG-335 | 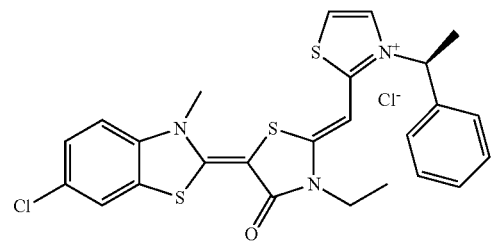 [SMILES: CCn1c(=O)/c(=C2\Sc3cc(Cl)ccc3N2C)s/c1=C\c1scc[n+]1[C@@H](C)c1ccccc1 ; [Cl-]] | 548.56 | 0.14 ± 0.02 | 0.11 ± 0.01 | 1.4 ± 0.1 |
| JG-336 | 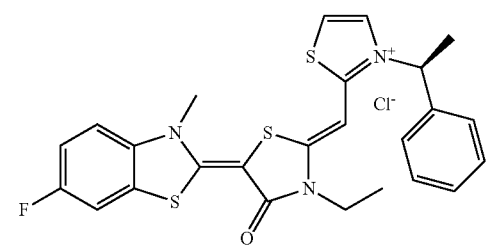 [SMILES: CCn1c(=O)/c(=C2\Sc3cc(F)ccc3N2C)s/c1=C\c1scc[n+]1[C@@H](C)c1ccccc1 ; [Cl-]] | 532.11 | 0.18 ± 0.02 | 0.21 ± 0.02 | 2.2 ± 0.1 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
|---|---|---|---|---|---|
| JG-337 | 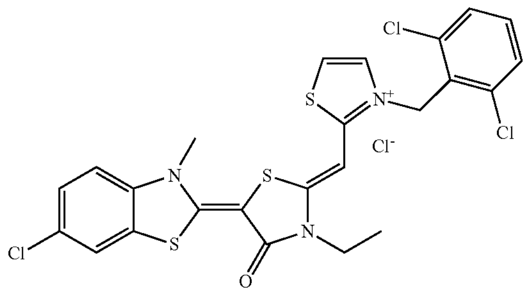 | 603.42 | 0.16 ± 0.01 | 0.16 ± 0.01 | 1.4 ± 0.1 |
| JG-338 | 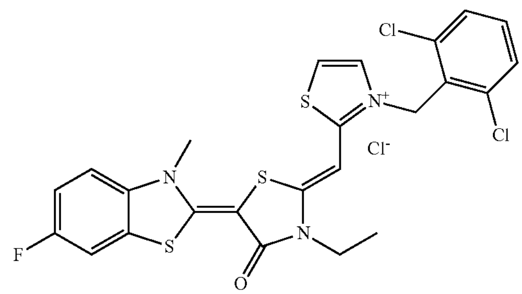 [SMILES: CCn1c(=O)/c(=C2\Sc3cc(F)ccc3N2C)s/c1=C\c1scc[n+]1Cc1c(Cl)cccc1Cl ; [Cl-]] | 586.96 | 0.17 ± 0.02 | 0.14 ± 0.01 | 1.0 ± 0.03 |
| JG-339 | 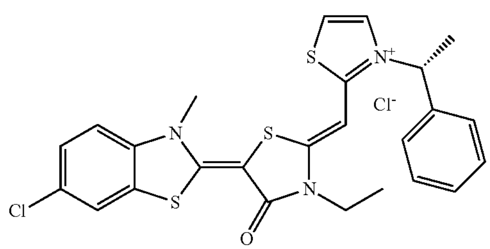 [SMILES: CCn1c(=O)/c(=C2\Sc3cc(Cl)ccc3N2C)s/c1=C\c1scc[n+]1[C@H](C)c1ccccc1 ; [Cl-]] | 548.56 | 0.37 ± 0.04 | 0.19 ± 0.02 | 1.5 ± 0.08 |
| JG-340 | 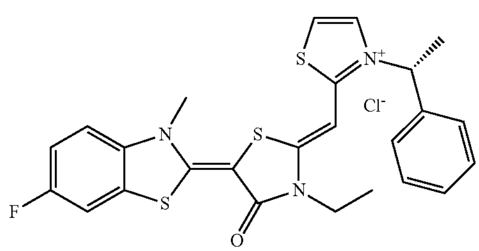 [SMILES: CCn1c(=O)/c(=C2\Sc3cc(F)ccc3N2C)s/c1=C\c1scc[n+]1[C@H](C)c1ccccc1 ; [Cl-]] | 532.11 | 0.24 ± 0.03 | 0.38 ± 0.03 | 1.5 ± 0.05 |
| JG-341 | 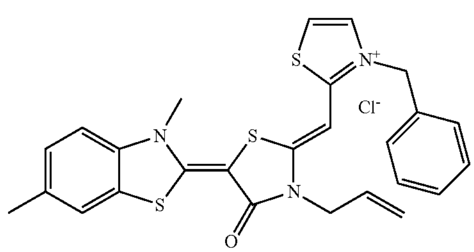 [SMILES: C=CCn1c(=O)/c(=C2\Sc3cc(C)ccc3N2C)s/c1=C\c1scc[n+]1Cc1ccccc1 ; [Cl-]] | 526.13 | 0.15 ± 0.01 | 0.11 ± 0.01 | 1.6 ± 0.1 |

TABLE 1-continued
Chemical structure, molecule weights and biological activities of selected compounds.
| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-342 | 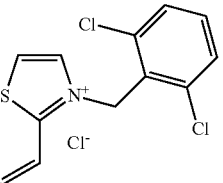 | 597.03 | 0.093 ± 0.007 | 0.10 ± 0.01 | 0.30 ± 0.10 |
| JG-343 | 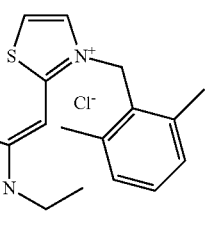 | 556.20 | 0.22 ± 0.02 | 0.25 ± 0.01 | 0.64 ± 0.01 |
| JG-344 | 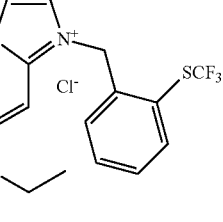 | 628.20 | 0.087 ± 0.007 | 0.17 ± 0.01 | 0.46 ± 0.03 |
| JG-345 | 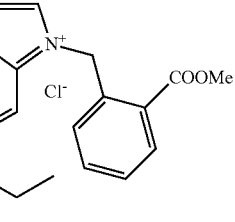 | 586.18 | 0.049 ± 0.003 | 0.046 ± 0.006 | 1.0 ± 0.1 |
| JG-346 | 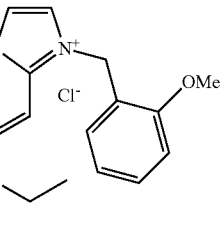 | 558.17 | 0.11 ± 0.01 | 0.073 ± 0.007 | 0.71 ± 0.03 |
| JG-347 | 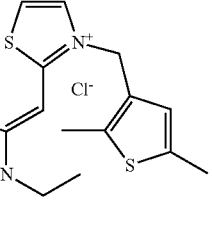 | 562.22 | 0.095 ± 0.008 | 0.21 ± 0.01 | 0.60 ± 0.01 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
| --- | --- | --- | --- | --- | --- |
| JG-348 | 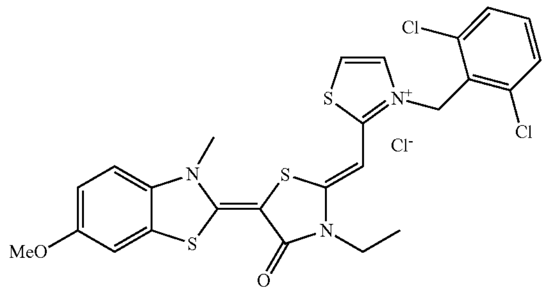 [SMILES: CCn1c(=O)/c(=C2\Sc3cc(SC)ccc3N2C)s/c1=C\c1scc[n+]1Cc1c(Cl)cccc1Cl ; [Cl-]] | 599.00 | 0.10 ± 0.01 | 0.10 ± 0.01 | 1.1 ± 0.1 |
| JG-349 | 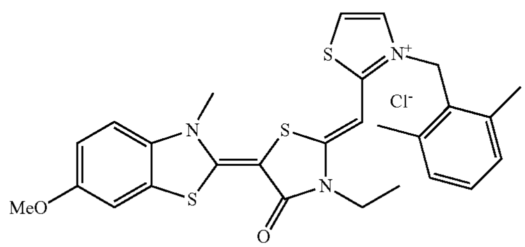 [SMILES: CCn1c(=O)/c(=C2\Sc3cc(SC)ccc3N2C)s/c1=C\c1scc[n+]1Cc1c(C)cccc1C ; [Cl-]] | 558.17 | 0.12 ± 0.01 | 0.23 ± 0.01 | 1.1 ± 0.1 |
| JG-350 | 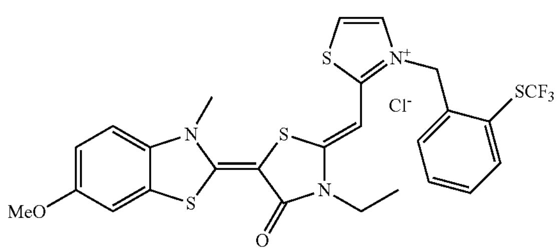 | 630.17 | 0.059 ± 0.007 | 0.10 ± 0.01 | 1.2 ± 0.1 |
| JG-351 | 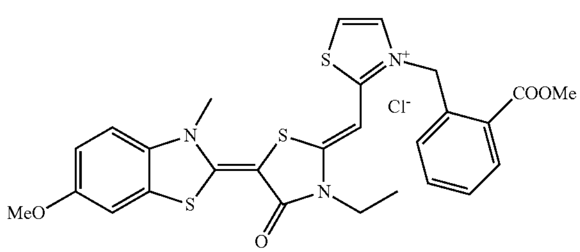 | 588.15 | 0.14 ± 0.01 | 0.11 ± 0.01 | 1.6 ± 0.1 |
| JG-352 | 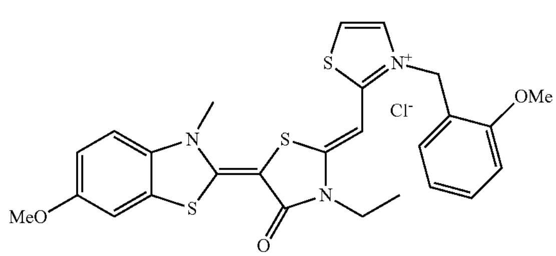 [SMILES: CCn1c(=O)/c(=C2\Sc3cc(SC)ccc3N2C)s/c1=C\c1scc[n+]1Cc1ccccc1OC ; [Cl-]] | 560.14 | 0.076 ± 0.005 | 0.062 ± 0.006 | 0.77 ± 0.03 |

TABLE 1-continued

Chemical structure, molecule weights and biological activities of selected compounds.

| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-353 | 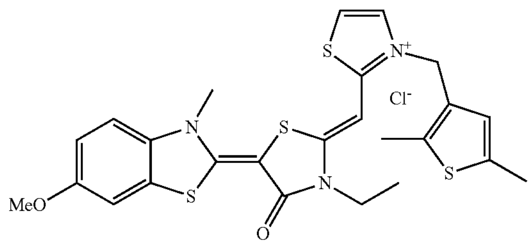 [SMILES: CCn1c(=O)/c(=C2\Sc3cc(SC)ccc3N2C)s/c1=C\c1scc[n+]1Cc1cc(C)sc1C ; [Cl-]] | 564.19 | 0.15 ± 0.01 | 0.15 ± 0.01 | 1.1 ± 0.1 |
| JG-354 | 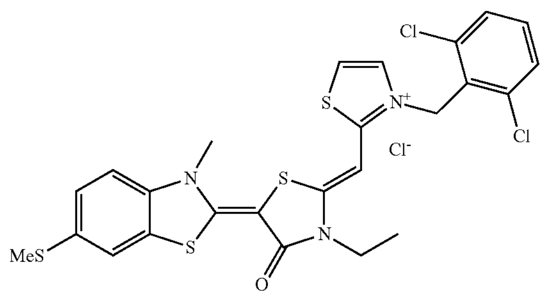 | 615.06 | 0.13 ± 0.01 | 0.096 ± 0.010 | 1.1 ± 0.1 |
| JG-355 | 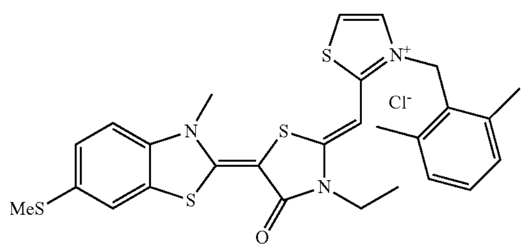 | 574.23 | 0.28 ± 0.02 | 0.21 ± 0.01 | 1.5 ± 0.1 |
| JG-356 | 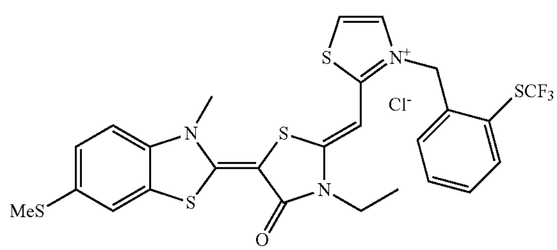 | 646.24 | 0.089 ± 0.006 | 0.090 ± 0.005 | 1.9 ± 0.1 |
| JG-357 | 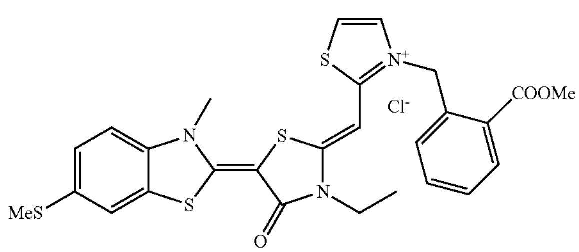 | 604.21 | 0.25 ± 0.01 | 0.14 ± 0.01 | 3.5 ± 0.2 |
| JG-358 | 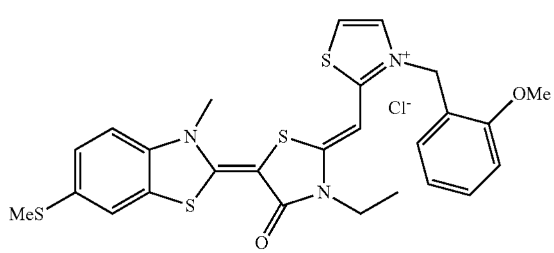 | 576.20 | 0.22 ± 0.01 | 0.11 ± 0.01 | 1.6 ± 0.1 |

TABLE 1-continued

Chemical structure, molecule weights and biological activities of selected compounds.

| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-359 | 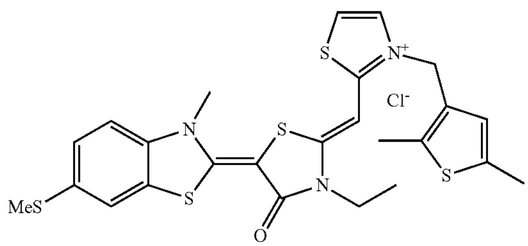 | 580.25 | 0.21 ± 0.01 | 0.25 ± 0.01 | 1.6 ± 0.1 |
| JG-360 | 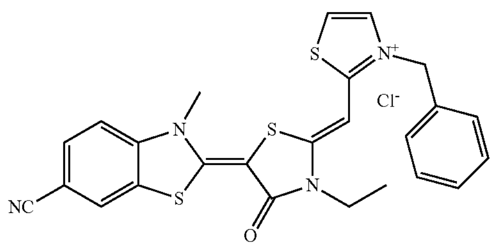 [SMILES: CCn1c(=O)/c(=C2\Sc3cc(C#N)ccc3N2C)s/c1=C\c1scc[n+]1Cc1ccccc1 ; [Cl-]] | 525.10 | 1.3 ± 0.1 | 2.3 ± 0.1 | 2.3 ± 0.1 |
| JG-361 | 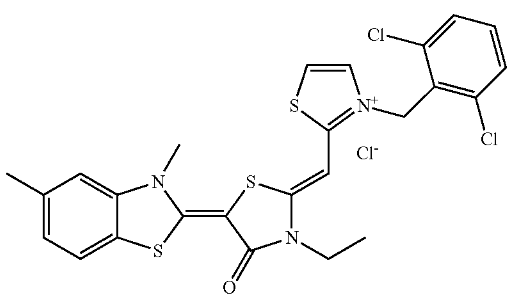 [SMILES: CCn1c(=O)/c(=C2\Sc3ccc(C)cc3N2C)s/c1=C\c1scc[n+]1Cc1c(Cl)cccc1Cl ; [Cl-]] | 583.00 | 0.088 ± 0.008 | 0.054 ± 0.006 | 0.55 ± 0.03 |
| JG-362 | 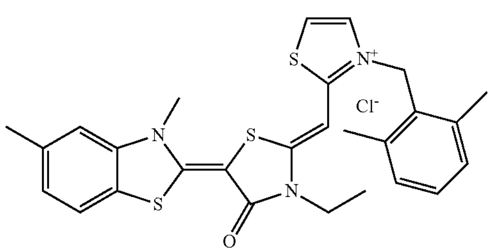 | 542.17 | 0.19 ± 0.02 | 0.23 ± 0.01 | 2.3 ± 0.1 |
| JG-363 | 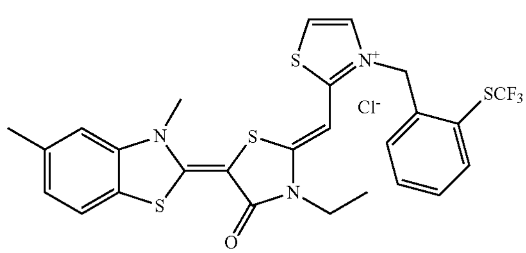 | 614.18 | 0.067 ± 0.005 | 0.084 ± 0.012 | 2.1 ± 0.1 |

TABLE 1-continued
Chemical structure, molecule weights and biological activities of selected compounds.
| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-364 | 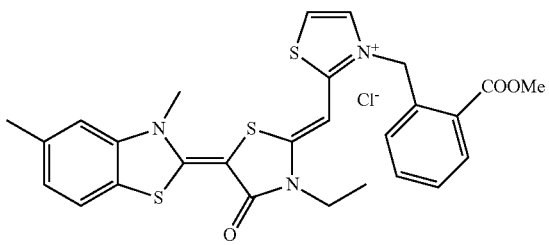 [SMILES: CCn1c(=O)/c(=C2\Sc3ccc(C)cc3N2C)s/c1=C\c1scc[n+]1Cc1ccccc1C(=O)OC ; [Cl-]] | 572.15 | 0.15 ± 0.01 | 0.11 ± 0.01 | 2.3 ± 0.2 |
| JG-365 | 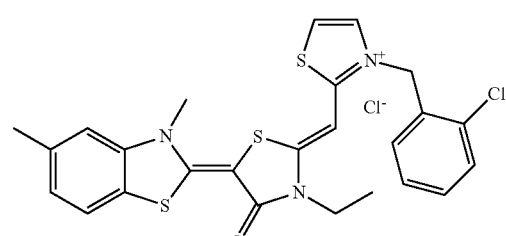 | 548.56 | 0.11 ± 0.01 | 0.16 ± 0.02 | 0.42 ± 0.02 |
| JG-366 | 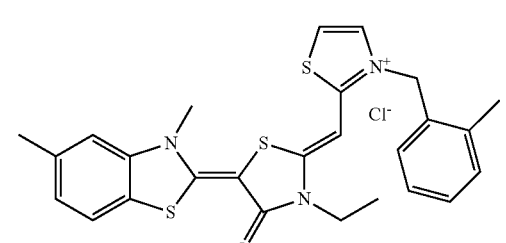 | 528.14 | 0.19 ± 0.01 | 0.22 ± 0.02 | 0.99 ± 0.04 |
| JG-367 | 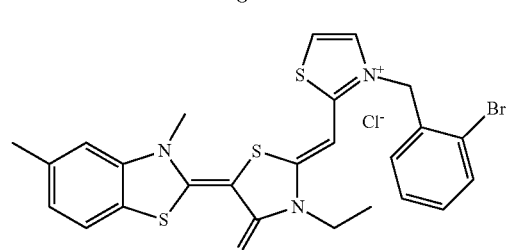 | 593.01 | 0.12 ± 0.01 | 0.22 ± 0.02 | 0.54 ± 0.02 |
| JG-368 | 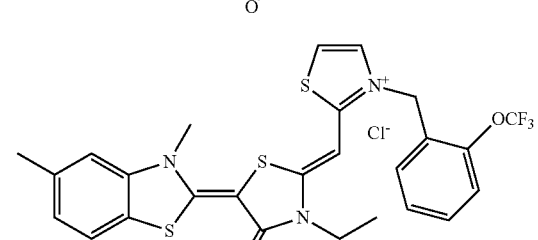 | 598.11 | 0.089 ± 0.006 | 0.18 ± 0.01 | 1.4 ± 0.1 |
| JG-369 | 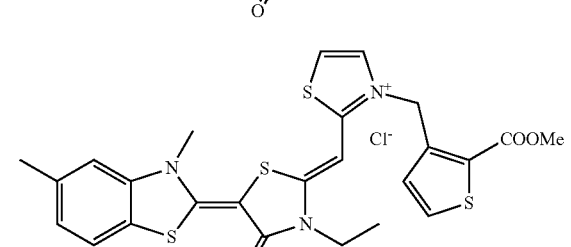 | 578.18 | 0.063 ± 0.004 | 0.12 ± 0.01 | 0.44 ± 0.02 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
|---|---|---|---|---|---|
| JG-370 | 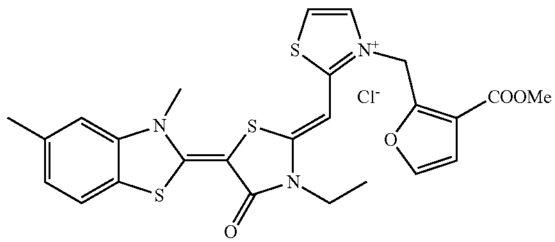 [SMILES: CCn1c(=O)/c(=C2\Sc3ccc(C)cc3N2C)s/c1=C\c1scc[n+]1Cc1occc1C(=O)OC ; [Cl-]] | 562.11 | 0.22 ± 0.01 | 0.18 ± 0.02 | 1.2 ± 0.1 |
| JG-371 | 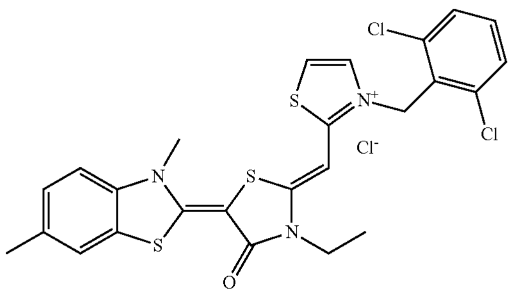 [SMILES: CCn1c(=O)/c(=C2\Sc3cc(C)ccc3N2C)s/c1=C\c1scc[n+]1Cc1c(Cl)cccc1Cl ; [Cl-]] | 583.00 | 0.069 ± 0.004 | 0.070 ± 0.010 | 0.68 ± 0.02 |
| JG-372 | 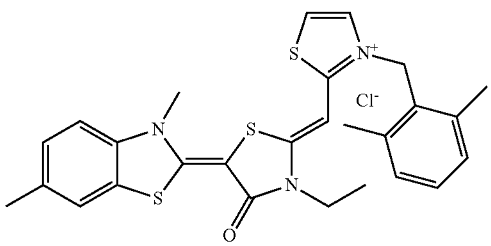 | 542.17 | 0.18 ± 0.01 | 0.68 ± 0.16 | 0.67 ± 0.01 |
| JG-373 | 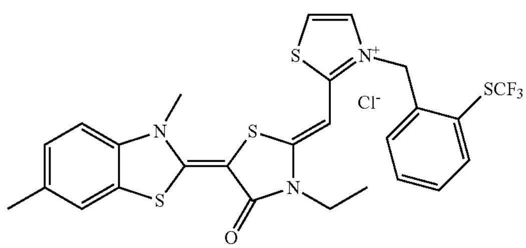 | 614.18 | 0.095 ± 0.005 | 0.22 ± 0.03 | 0.44 ± 0.03 |
| JG-374 | 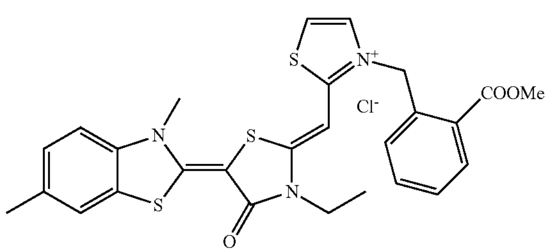 [SMILES: CCn1c(=O)/c(=C2\Sc3cc(C)ccc3N2C)s/c1=C\c1scc[n+]1Cc1ccccc1C(=O)OC ; [Cl-]] | 572.15 | 0.16 ± 0.01 | 0.15 ± 0.01 | 0.69 ± 0.03 |
| JG-375 | 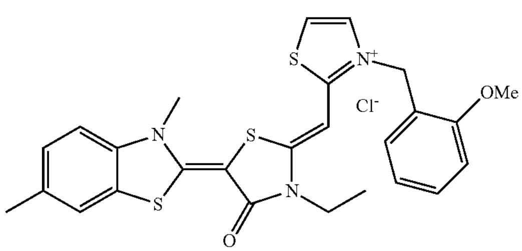 [SMILES: CCn1c(=O)/c(=C2\Sc3cc(C)ccc3N2C)s/c1=C\c1scc[n+]1Cc1ccccc1OC ; [Cl-]] | 544.14 | 0.071 ± 0.006 | 0.082 ± 0.010 | 0.96 ± 0.03 |

TABLE 1-continued

Chemical structure, molecule weights and biological activities of selected compounds.

| Compound | Structure | M.W. | $IC_{50}/\mu M$ MCF-7 | $IC_{50}/\mu M$ MDA-MB-231 | $IC_{50}/\mu M$ MEF (C57BL/6) |
| --- | --- | --- | --- | --- | --- |
| JG-376 | 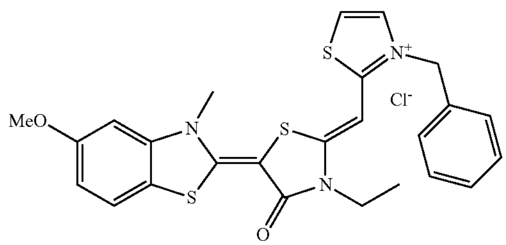 [SMILES: CCn1c(=O)/c(=C2\Sc3ccc(OC)cc3N2C)s/c1=C\c1scc[n+]1Cc1ccccc1 ; [Cl-]] | 530.12 | 0.37 ± 0.02 | 0.36 ± 0.05 | 1.0 ± 0.1 |
| JG-377 | 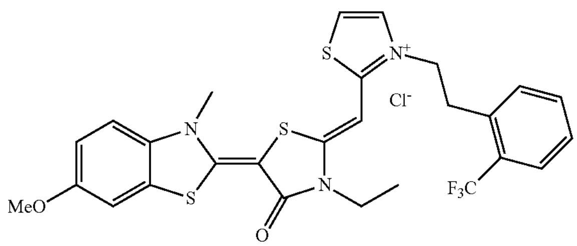 [SMILES: CCn1c(=O)/c(=C2\Sc3cc(OC)ccc3N2C)s/c1=C\c1scc[n+]1CCc1ccccc1C(F)(F)F ; [Cl-]] | 612.14 | 0.12 ± 0.01 | 0.19 ± 0.03 | >10 |
| JG-378 | 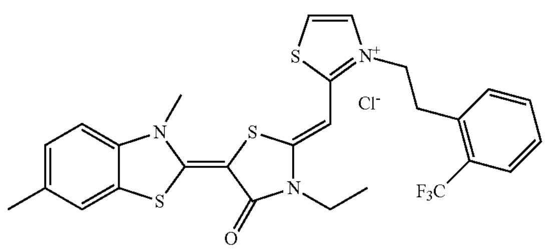 | 596.14 | 0.13 ± 0.01 | 0.14 ± 0.02 | 0.87 ± 0.03 |
| JG-379 | 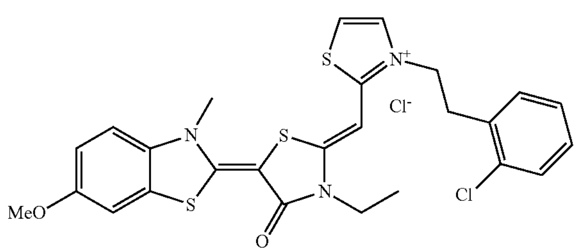 | 578.58 | 0.18 ± 0.01 | 0.20 ± 0.03 | 0.90 ± 0.01 |
| JG-380 | 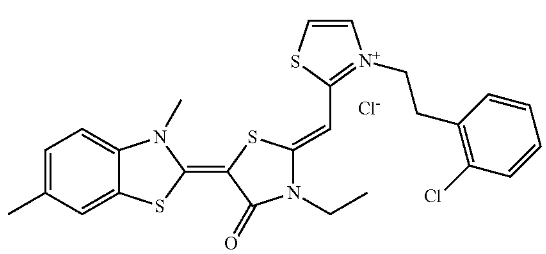 [SMILES: CCn1c(=O)/c(=C2\Sc3cc(C)ccc3N2C)s/c1=C\c1scc[n+]1CCc1ccccc1Cl ; [Cl-]] | 562.59 | 0.20 ± 0.02 | 0.25 ± 0.03 | 0.94 ± 0.03 |
| JG-381 | 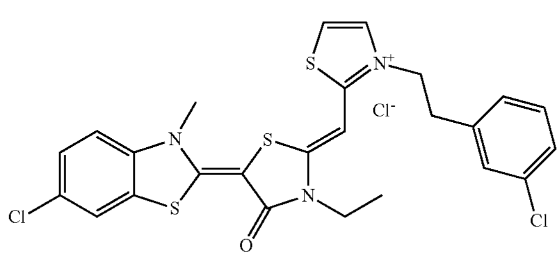 | 583.00 | 0.55 ± 0.03 | 0.62 ± 0.05 | 2.3 ± 0.2 |

TABLE 1-continued
Chemical structure, molecule weights and biological activities of selected compounds.
| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-382 | 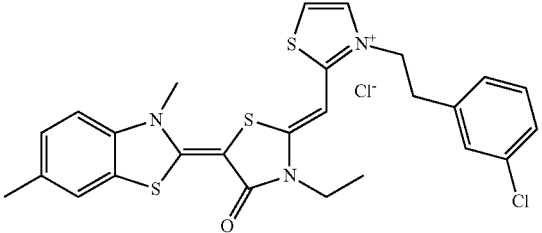 [SMILES: CCn1c(=O)/c(=C2\Sc3cc(C)ccc3N2C)s/c1=C\c1scc[n+]1CCc1cccc(Cl)c1 ; [Cl-]] | 562.59 | 0.59 ± 0.03 | 0.46 ± 0.06 | 1.2 ± 0.1 |
| JG-383 | 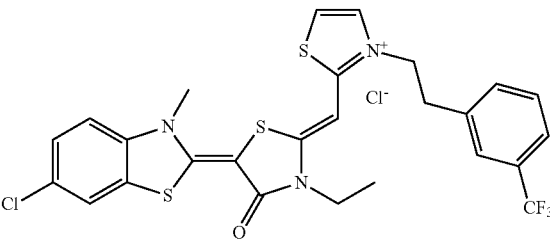 [SMILES: CCn1c(=O)/c(=C2\Sc3cc(Cl)ccc3N2C)s/c1=C\c1scc[n+]1CCc1cccc(C(F)(F)F)c1 ; [Cl-]] | 616.56 | 0.78 ± 0.06 | 0.74 ± 0.08 | 2.3 ± 0.2 |
| JG-384 | 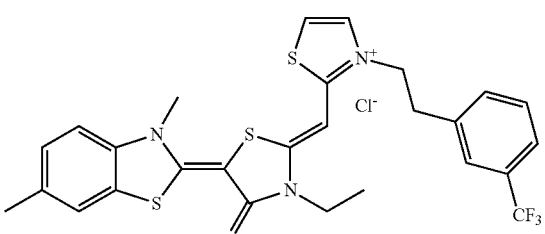 | 596.14 | 0.62 ± 0.08 | 0.68 ± 0.10 | 1.1 ± 0.1 |
| JG-385 | 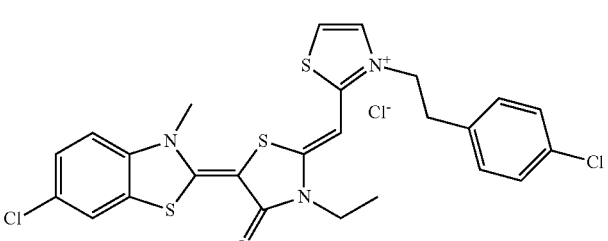 | 583.00 | 0.69 ± 0.05 | 0.61 ± 0.05 | 4.4 ± 0.3 |
| JG-386 | 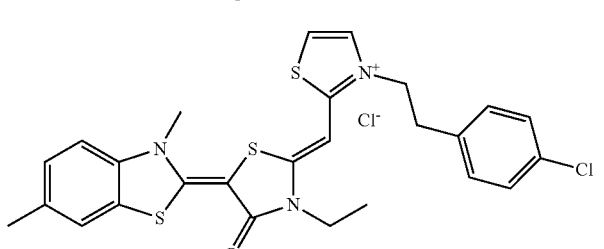 | 562.59 | 0.53 ± 0.05 | 0.28 ± 0.03 | 1.7 ± 0.1 |
| JG-387 | 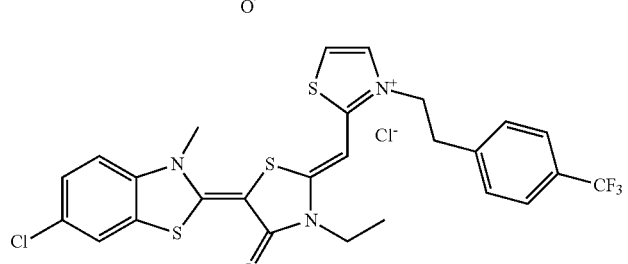 | 616.56 | 0.78 ± 0.09 | 0.74 ± 0.04 | >10 |

TABLE 1-continued
Chemical structure, molecule weights and biological activities of selected compounds.
| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-388 | 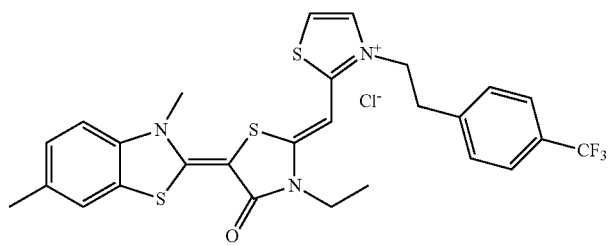 [SMILES: CCn1c(=O)/c(=C2\Sc3cc(C)ccc3N2C)s/c1=C\c1scc[n+]1CCc1ccc(C(F)(F)F)cc1 ; [Cl-]] | 596.14 | 0.50 ± 0.04 | 0.62 ± 0.07 | 1.6 ± 0.1 |
| JG-389 | 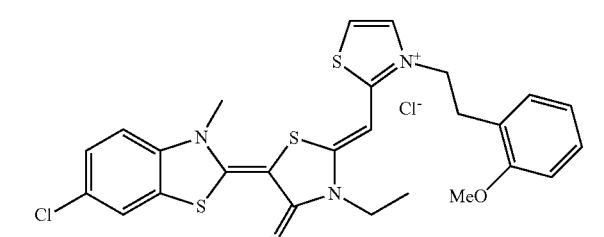 | 578.58 | 0.86 ± 0.08 | 0.27 ± 0.01 | 2.4 ± 0.1 |
| JG-390 | 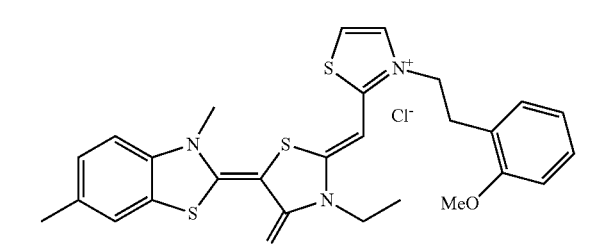 | 588.17 | 0.31 ± 0.04 | 0.12 ± 0.01 | 1.2 ± 0.1 |
| JG-391 | 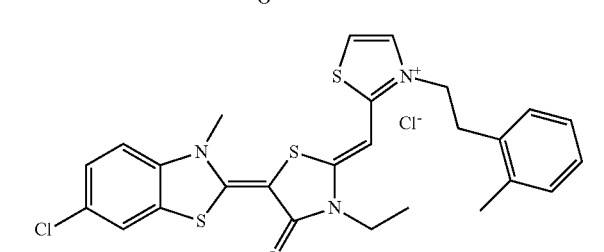 | 562.59 | 0.68 ± 0.04 | 0.26 ± 0.01 | 2.5 ± 0.2 |
| JG-392 | 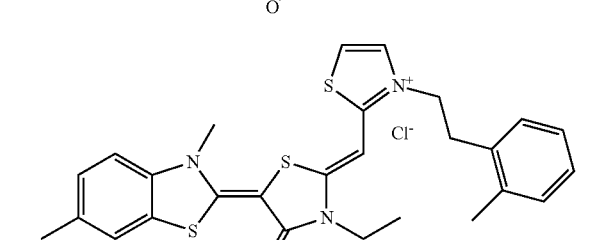 | 542.17 | 0.35 ± 0.03 | 0.19 ± 0.02 | 1.2 ± 0.1 |
| JG-393 | 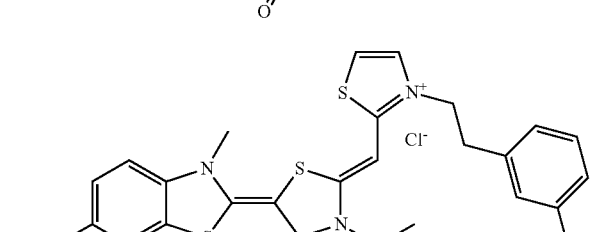 | 612.14 | 0.68 ± 0.13 | 0.21 ± 0.01 | 2.1 ± 0.1 |

TABLE 1-continued

Chemical structure, molecule weights and biological activities of selected compounds.

| Compound | Structure | M.W. | IC$_{50}$/μM MCF-7 | IC$_{50}$/μM MDA-MB-231 | IC$_{50}$/μM MEF (C57BL/6) |
| --- | --- | --- | --- | --- | --- |
| JG-394 | 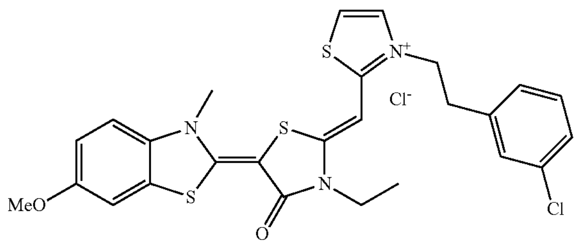 [SMILES: CCn1c(=O)/c(=C2\Sc3cc(OC)ccc3N2C)s/c1=C\c1scc[n+]1CCc1cccc(Cl)c1 ; [Cl-]] | 578.58 | 0.56 ± 0.06 | 0.24 ± 0.01 | 2.3 ± 0.1 |
| JG-395 | 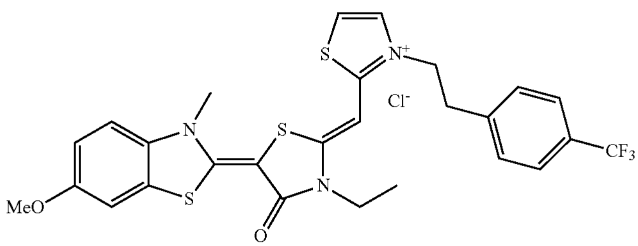 [SMILES: CCn1c(=O)/c(=C2\Sc3cc(OC)ccc3N2C)s/c1=C\c1scc[n+]1CCc1ccc(C(F)(F)F)cc1 ; [Cl-]] | 612.14 | 0.51 ± 0.06 | 0.42 ± 0.03 | 2.9 ± 0.1 |
| JG-396 | 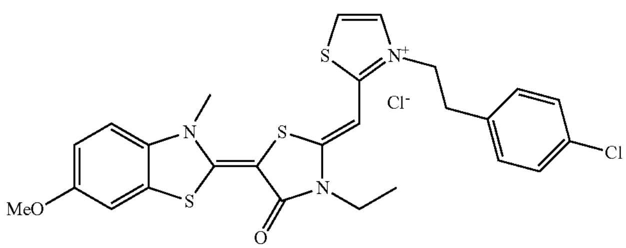 [SMILES: CCn1c(=O)/c(=C2\Sc3cc(OC)ccc3N2C)s/c1=C\c1scc[n+]1CCc1ccc(Cl)cc1 ; [Cl-]] | 578.58 | 1.7 ± 0.3 | 0.20 ± 0.03 | 4.0 ± 0.2 |
| JG-397 | 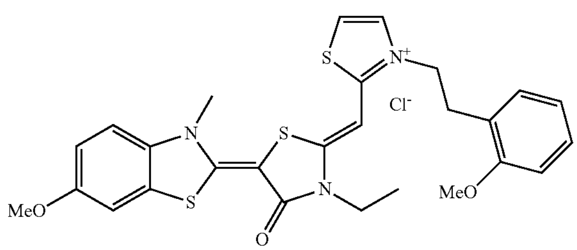 [SMILES: CCn1c(=O)/c(=C2\Sc3cc(OC)ccc3N2C)s/c1=C\c1scc[n+]1CCc1ccccc1OC ; [Cl-]] | 574.17 | 0.080 ± 0.008 | 0.083 ± 0.007 | 1.3 ± 0.1 |
| JG-398 | 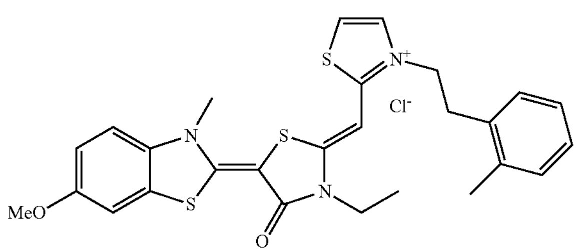 [SMILES: CCn1c(=O)/c(=C2\Sc3cc(OC)ccc3N2C)s/c1=C\c1scc[n+]1CCc1ccccc1C ; [Cl-]] | 588.17 | 0.24 ± 0.02 | 0.14 ± 0.01 | 1.1 ± 0.1 |
| JG-399 | 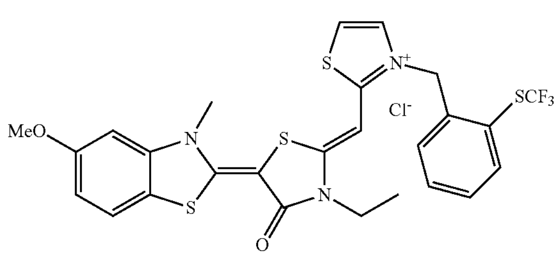 [SMILES: CCn1c(=O)/c(=C2\Sc3ccc(OC)cc3N2C)s/c1=C\c1scc[n+]1Cc1ccccc1OC(F)(F)F ; [Cl-]] | 630.17 | 0.20 ± 0.01 | 0.11 ± 0.01 | 3.1 ± 0.2 |

TABLE 1-continued
Chemical structure, molecule weights and biological activities of selected compounds.
| Compound | Structure | M.W. | IC$_{50}$/μM MCF-7 | IC$_{50}$/μM MDA-MB-231 | IC$_{50}$/μM MEF (C57BL/6) |
|---|---|---|---|---|---|
| JG-400 | 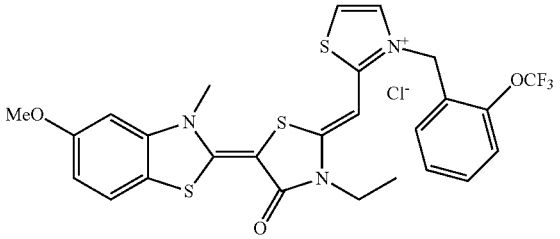 | 614.11 | 0.16 ± 0.02 | 0.16 ± 0.01 | 2.2 ± 0.1 |
| JG-401 | 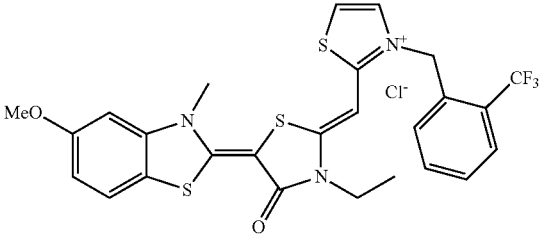 [SMILES: CCn1c(=O)/c(=C2\Sc3ccc(OC)cc3N2C)s/c1=C\c1scc[n+]1Cc1ccccc1C(F)(F)F ; [Cl-]] | 598.11 | 0.45 ± 0.04 | 0.11 ± 0.01 | 0.27 ± 0.03 |
| JG-402 | 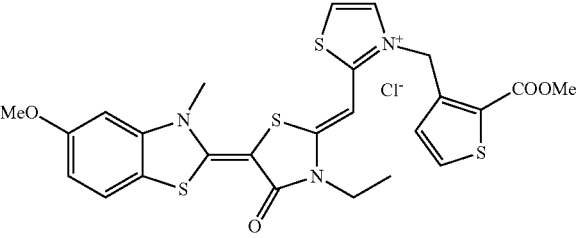 [SMILES: CCn1c(=O)/c(=C2\Sc3ccc(OC)cc3N2C)s/c1=C\c1scc[n+]1Cc1ccsc1C(=O)OC ; [Cl-]] | 594.17 | 0.45 ± 0.04 | 0.23 ± 0.01 | 0.82 ± 0.06 |
| JG-403 | 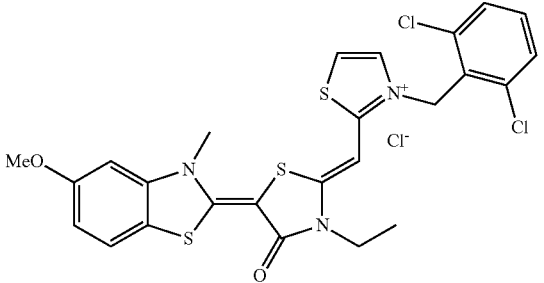 [SMILES: CCn1c(=O)/c(=C2\Sc3ccc(OC)cc3N2C)s/c1=C\c1scc[n+]1Cc1c(Cl)cccc1Cl ; [Cl-]] | 599.00 | 0.70 ± 0.08 | 0.20 ± 0.01 | 1.2 ± 0.1 |
| JG-404 | 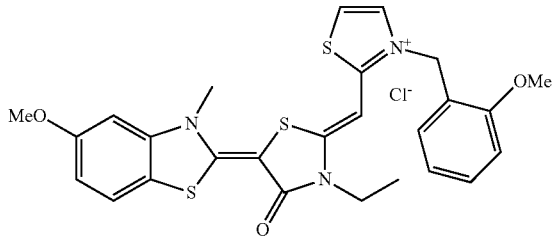 [SMILES: CCn1c(=O)/c(=C2\Sc3ccc(OC)cc3N2C)s/c1=C\c1scc[n+]1Cc1ccccc1OC ; [Cl-]] | 560.14 | 0.79 ± 0.10 | 0.30 ± 0.03 | 1.3 ± 0.1 |

TABLE 2

Functional characterization of selected compounds.

| Compound | M.W. | EC50/µM MCF-7 | EC50/µM MEF | EC50/µM IMR-90 | SI MEF/ MCF-7 | SI IMR-90/MCF-7 | Solubility µM | Microsomal min |
|---|---|---|---|---|---|---|---|---|
| JG-98  | 534.54 | 0.71 ± 0.22   | 4.5 ± 0.5 | 1.4 ± 0.2 | 6  | 2    | 31 | 37  |
| JG-194 | 514.12 | 0.16 ± 0.02   | 1.9 ± 0.1 | 1.8 ± 0.3 | 11 | 11   | 16 | 40  |
| JG-231 | 619.45 | 0.12 ± 0.01   | 2.5 ± 0.1 | 4.6 ± 0.3 | 20 | 38   | 16 | >60 |
| JG-294 | 636.94 | 0.10 ± 0.01   | 3.5 ± 0.4 | 9.8 ± 2.0 | 35 | 98   | 31 | >60 |
| JG-300 | 586.10 | 0.11 ± 0.01   | 1.4 ± 0.1 | 3.3 ± 0.3 | 12 | 30   | 16 | 37  |
| JG-311 | 630.17 | 0.098 ± 0.009 | 2.0 ± 0.1 | 3.5 ± 0.6 | 20 | 35   | 16 | 22  |
| JG-312 | 614.18 | 0.10 ± 0.01   | 3.2 ± 0.2 | >10       | 32 | >100 | 16 | 23  |
| JG-345 | 586.18 | 0.049 ± 0.003 | 1.0 ± 0.1 | 3.2 ± 0.7 | 20 | 65   | 31 | 25  |
| JG-356 | 646.24 | 0.089 ± 0.006 | 1.9 ± 0.1 | 1.5 ± 0.1 | 21 | 16   | 16 | 23  |

TABLE 3A

Pharmacokinetic parameters of JG-294

| Pharmacokinetic parameters | |
|---|---|
| Cmax/nM | 0.058 |
| Tmax/h | 2 |
| $t_{1/2}$/h | 29.8 |
| $AUC_{0-\infty}$/nM × h | 2429 |

TABLE 3B

Pharmacokinetic parameters of JG-345

| Pharmacokinetic parameters | |
|---|---|
| Cmax/nM | 0.087 |
| Tmax/h | 1 |
| $t_{1/2}$/h | 11.4 |
| $AUC_{0-\infty}$/nM × h | 1524 |

Embodiments

Embodiment 1. A Compound of Formula:

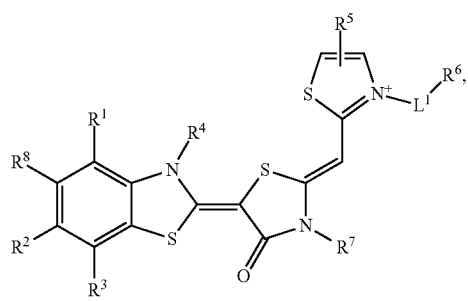

(I)

wherein:

$R^1$ is hydrogen, halogen, —$CX^a_3$, —CN, —$SR^9$, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —$N(O)_{m1}$, —$NR^9R^{10}$, —NH—O—$R^9$, —NHC(O)$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^b_3$, —CN, —$SR^{11}$, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —NH—O—$R^{11}$, —NHC(O)$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^c_3$, —CN, —$SR^{13}$, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —NHC(O)$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —$CX^d_3$, —CN, —$SR^{15}$, —$SO_2Cl$, —$SO_{n4}R^{15}$, —$SO_{v4}NR^{15}R^{16}$, —$NHNH_2$, —$ONR^{15}R^{16}$, —NHC=(O)$NHNH_2$, —NHC=(O)$NR^{15}R^{16}$, —$N(O)_{m4}$, —$NR^{15}R^{16}$, —NH—O—R, —NHC(O)$R^5$, —C(O)$R^{15}$, —C(O)—OR, —C(O)$NR^{15}R^{16}$, —$OR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is unsubstituted alkyl, unsubstituted heteroalkyl, unsubstituted cycloalkyl, unsubstituted heterocycloalkyl, unsubstituted aryl, or unsubstituted heteroaryl;

$R^5$ is hydrogen, halogen, —$CX^e_3$, —CN, —$SR^{17}$, —$SO_2Cl$, —$SO_{n5}R^{17}$, —$SO_{v5}NR^{17}R^{18}$, —$NHNH_2$, —$ONR^{17}R^{18}$, —NHC=(O)$NHNH_2$, —NHC=(O)$NR^{17}R^{18}$, —$N(O)_{m5}$, —$NR^{17}R^{18}$, —NH—O—$R^{17}$, —NHC(O)$R^{17}$, —C(O)$R^{17}$, —C(O)—$OR^{17}$, —C(O)$NR^{17}R^{18}$, —$OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is $R^{6A}$-substituted cycloalkyl, $R^{6A}$-substituted heterocycloalkyl, $R^{6A}$-substituted aryl or $R^{6A}$-substituted heteroaryl;

$R^{6A}$ is independently halogen, —$CX^f_3$, —CN, —$SR^{19}$, —$SO_2Cl$, —$SO_{n6}R^{19}$, —$SO_{v6}NR^{19}R^{20}$, —$NHNH_2$, —$ONR^{19}R^2$, —NHC=(O)$NHNH_2$, —NHC=(O)

$NR^{19}R^{20}$, $-N(O)_{m6}$, $-NR^{19}R^{20}$, $-NH-O-R^{19}$, $-NHC(O)R^{19}$, $-C(O)R^{19}$, $-C(O)-OR^{19}$, $-C(O)NR^{19}R^{20}$, $-OR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, $-CX^g{}_3$, $-CN$, $-SR^{21}$, $-SO_2Cl$, $-SO_{n7}R^{21}$, $-SO_{v7}NR^{21}R^{22}$, $-NHNH_2$, $-ONR^{21}R^{22}$, $-NHC=(O)NHNH_2$, $-NHC=(O)NR^{21}R^{22}$, $-N(O)_{m7}$, $-NR^{21}R^{22}$, $-NH-O-R^{21}$, $-NHC(O)R^{21}$, $-C(O)R^{21}$, $-C(O)-OR^{21}$, $-C(O)NR^{21}R^{22}$, $-OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ is a bond, $-S(O)-$, $-S(O)_2NH-$, $-NHS(O)_2-$, $-C(O)O-$, $-OC(O)-$, $-C(O)-$, $-C(O)NH-$, $-NH-$, $-NHC(O)-$, $-O-$, $-S-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^9$, $R^{10}$, $R^{11}$, $R^{12}$, $R^{13}$, $R^{14}$, $R^5$, $R^{16}$, $R^{17}$, $R^{18}$, $R^{19}$, $R^{20}$, $R^{21}$, and $R^{22}$ are independently hydrogen, halogen, $=O$, $=S$, $-CF_3$, $-CN$, $-CCl_3$, $-COOH$, $-CH_2COOH$, $-COCH_3$, $-CONH_2$, $-OH$, $-OC(O)CH_3$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$X^a$, $X^b$, $X^c$, $X^d$, $X^e$, $X^f$ and $X^g$ are independently $-F$, $-Cl$, $-Br$, or $-I$;

$n_1$, $n_2$, $n_3$, $n_4$, $n_5$, $n_6$ and $n_7$ are independently an integer from 0 to 4;

$m_1$, $m_2$, $m_3$, $m_4$, $m_5$, $m_6$ and $m_7$ are independently an integer from 1 to 2; and $v_1$, $v_2$, $v_3$, $v_4$, $v_5$, $v_6$ and $v_7$ are independently an integer from 1 to 2;

wherein if $R^1$, $R^2$, and $R^3$ are independently hydrogen, $-Cl$, $-F$, $-OCH_3$, or $-CF_3$, then $-L^1-R^6$ is not $-CH_2$pyridyl, -benzyl, $-CH_2$-difluorophenyl, $-CH_2$-cyclopropyl, $-CH_2$-4-$(CH_2NHC(O)$-tbutyl)phenyl, $-CH_2$-5-nitrofuranyl, $-CH_2CH_2$-5-nitrofuranyl, $-CH_2$-2-(5-$CF_3$)furanyl, $-CH_2$-fluorophenyl, $-CH_2$-chlorophenyl, $-CH_2$-nitrophenyl, $-CH_2$-cyanophenyl, $-CH(CH_3)C(O)Ph$, $-CH_2$-(methyl)phenyl, $-CH_2$-trifluoromethylphenyl, $-CH_2$-trifluoromethoxyphenyl, $-CH_2$-difluoromethoxyphenyl, $-CH_2$-3-(2-$CO_2CH_3$)thienyl, $-CH_2$-3-(2-bromo)thienyl, $-CH_2$-3-isoxazolyl, $-CH_2$-5-isoxazolyl, $-CH_2$-5-(3-phenyl)isoxazolyl, $-CH_2$-3-(2-bromo)pyridyl, $-CH_2$-3-thienyl, $-CH_2$-2-(5-$CO_2CH_2CH_3$)furanyl, $-CH_2$-4-(2-methyl)thiazolyl, $-CH_2$-2-(5-$CO_2CH_3$)furanyl, $-CH_2$-5-(3-methyl)isoxazolyl, or $-CH_2-CH(CH_3)$phenyl.

Embodiment 2. The compound of embodiment 1, wherein if $L^1$ is $-CH_2-$ and $R^6$ is phenyl, then $R^{6A}$ is not $-F$, $-CF_3$, $-OCHF_2$, $-NO_2$, $-OCF_3$, $-CH_3$, $-CN$, or $-Cl$.

Embodiment 3. The compound of embodiment 1, wherein if $L^1$ is $-CH_2-$ and $R^6$ is phenyl, then $R^{6A}$ is not halogen, $-CX^f{}_3$, $-OR^{19}$, or substituted or unsubstituted $C_1$-$C_5$ alkyl, wherein $X^f$ is halogen and $R^{19}$ is substituted or unsubstituted $C_1$-$C_5$ alkyl.

Embodiment 4. The compound of embodiment 1, wherein if $L^1$ is $-CH_2-$ and $R^6$ is $R^{6A}$-substituted 6-membered aryl, then $R^{6A}$ is not halogen, $-CX^f{}_3$, $-OR^{19}$, or substituted or unsubstituted $C_1$-$C_5$ alkyl, wherein $X^f$ is halogen and $R^{19}$ is substituted or unsubstituted $C_1$-$C_5$ alkyl.

Embodiment 5. The compound of embodiment 1, wherein if $L^1$ is unsubstituted $C_1$-$C_5$ alkylene and $R^6$ is phenyl, then $R^{6A}$ is not halogen, $-CX^f{}_3$, $-OR^{19}$, or substituted or unsubstituted $C_1$-$C_5$ alkyl, wherein $X^f$ is halogen and $R^{19}$ is substituted or unsubstituted $C_1$-$C_5$ alkyl.

Embodiment 6. The compound of embodiment 1, wherein if $L^1$ is unsubstituted $C_1$-$C_5$ alkylene and $R^6$ is $R^{6A}$-substituted 6-membered aryl, then $R^{6A}$ is not halogen, $-CX^f{}_3$, $-OR^{19}$, or substituted or unsubstituted $C_1$-$C_5$ alkyl, wherein $X^f$ is halogen and $R^{19}$ is substituted or unsubstituted $C_1$-$C_5$ alkyl.

Embodiment 7. The compound of embodiment 1, wherein if $L^1$ is $-CH_2-$ and $R^6$ is furanyl, then $R^{6A}$ is not $-CF_3$, $-NO_2$, $-C(O)OCH_3$ or $-C(O)OCH_2CH_3$.

Embodiment 8. The compound of embodiment 1, wherein if $L^1$ is $-CH_2-$ and $R^6$ is furanyl, then $R^{6A}$ is not $-CX^f{}_3$, or $-C(O)OR^{19}$, wherein $X^f$ is halogen and $R^{19}$ is substituted or unsubstituted $C_1$-$C_5$ alkyl.

Embodiment 9. The compound of embodiment 1, wherein if $L^1$ is $-CH_2-$ and $R^6$ is $R^{6A}$-substituted 5-membered heteroaryl, then $R^{6A}$ is not $-CX^f{}_3$, or $-C(O)OR^{19}$, wherein $X^f$ is halogen and $R^{19}$ is substituted or unsubstituted $C_1$-$C_5$ alkyl.

Embodiment 10. The compound of embodiment 1, wherein if $L^1$ is unsubstituted $C_1$-$C_5$ alkylene and $R^6$ is furanyl, then $R^{6A}$ is not $-CX^f{}_3$, or $-C(O)OR^{19}$, wherein $X^f$ is halogen and $R^{19}$ is substituted or unsubstituted $C_1$-$C_5$ alkyl.

Embodiment 11. The compound of embodiment 1, wherein if $L^1$ is unsubstituted $C_1$-$C_5$ alkylene and $R^6$ is $R^{6A}$-substituted 5-membered heteroaryl, then $R^{6A}$ is not $-CX^f{}_3$, or $-C(O)OR^{19}$ wherein $X^f$ is halogen and $R^{19}$ is substituted or unsubstituted $C_1$-$C_5$ alkyl.

Embodiment 12. The compound of embodiment 1, wherein if $L^1$ is $-CH_2-$ and $R^6$ is thiophene, then $R^{6A}$ is not $-Br$, $-C(O)OCH_3$, or $-C(O)OCH_2CH_3$.

Embodiment 13. The compound of embodiment 1, wherein if $L^1$ is $-CH_2-$ and $R^6$ is thiophene, then $R^{6A}$ is not halogen or $-C(O)OR^{19}$, wherein $R^{19}$ is substituted or unsubstituted $C_1$-$C_5$ alkyl.

Embodiment 14. The compound of embodiment 1, wherein if $L^1$ is $-CH_2-$ and $R^6$ is $R^{6A}$-substituted 5-membered heteroaryl, then $R^{6A}$ is not halogen or $-C(O)OR^{19}$, wherein $R^{19}$ is substituted or unsubstituted $C_1$-$C_5$ alkyl.

Embodiment 15. The compound of embodiment 1, wherein if $L^1$ is unsubstituted $C_1$-$C_5$ alkylene and $R^6$ is thiophene, then $R^{6A}$ is not halogen or $-C(O)OR^{19}$, wherein $R^{19}$ is substituted or unsubstituted $C_1$-$C_5$ alkyl.

Embodiment 16. The compound of embodiment 1, wherein if $L^1$ is unsubstituted $C_1$-$C_5$ alkylene and $R^6$ is $R^{6A}$-substituted 5-membered heteroaryl, then $R^{6A}$ is not halogen or $-C(O)OR^{19}$, wherein $R^{19}$ is substituted or unsubstituted $C_1$-$C_5$ alkyl.

Embodiment 17. The compound of embodiment 1, wherein if $L^1$ is $-CH_2-$ and $R^6$ is oxazolyl, then $R^{6A}$ is not methyl or phenyl.

Embodiment 18. The compound of embodiment 1, wherein if $L^1$ is —$CH_2$— and $R^6$ is oxazolyl, then $R^{6A}$ is not substituted or unsubstituted $C_1$-$C_5$ alkyl or substituted or substituted 6-membered aryl.

Embodiment 19. The compound of embodiment 1, wherein if $L^1$ is —$CH_2$— and $R^6$ is $R^{6A}$-substituted 5-membered heteroaryl, then $R^{6A}$ is not substituted or unsubstituted $C_1$-$C_5$ alkyl or substituted or unsubstituted 6-membered aryl.

Embodiment 20. The compound of embodiment 1, wherein if $L^1$ is unsubstituted $C_1$-$C_5$ alkylene and $R^6$ is oxazolyl, then $R^{6A}$ is not substituted or unsubstituted $C_1$-$C_5$ alkyl or substituted or unsubstituted 6-membered aryl.

Embodiment 21. The compound of embodiment 1, wherein if $L^1$ is unsubstituted $C_1$-$C_5$ alkylene and $R^6$ is $R^{6A}$-substituted 5-membered heteroaryl, then $R^{6A}$ is not substituted or unsubstituted $C_1$-$C_5$ alkyl or substituted or unsubstituted 6-membered aryl.

Embodiment 22. The compound of embodiment 1, wherein if $L^1$ is —$CH_2$— and $R^6$ is pyridyl, then $R^{6A}$ is not —Br.

Embodiment 23. The compound of embodiment 1, wherein if $L^1$ is —$CH_2$— and $R^6$ is pyridyl, then $R^{6A}$ is not halogen.

Embodiment 24. The compound of embodiment 1, wherein if $L^1$ is —$CH_2$— and $R^6$ is $R^{6A}$-substituted 6-membered heteroaryl, then $R^{6A}$ is not halogen.

Embodiment 25. The compound of embodiment 1, wherein if $L^1$ is unsubstituted $C_1$-$C_5$ alkylene and $R^6$ is pyridyl, then $R^{6A}$ is not halogen.

Embodiment 26. The compound of embodiment 1, wherein if $L^1$ is unsubstituted $C_1$-$C_5$ alkylene and $R^6$ is $R^{6A}$-substituted 6-membered heteroaryl, then $R^{6A}$ is not halogen.

Embodiment 27. The compound of embodiment 1, wherein if $L^1$ is —$CH_2$— and $R^6$ is thiazolyl, then $R^{6A}$ is not —$CH_3$ or —$C(O)OCH_3$.

Embodiment 28. The compound of embodiment 1, wherein if $L^1$ is —$CH_2$— and $R^6$ is thiazolyl, then $R^{6A}$ is not substituted or unsubstituted $C_1$-$C_5$ alkyl or —$C(O)OR^{19}$, wherein $R^{19}$ is substituted or unsubstituted $C_1$-$C_5$ alkyl.

Embodiment 29. The compound of embodiment 1, wherein if $L^1$ is —$CH_2$— and $R^6$ is $R^{6A}$-substituted 5-membered heteroaryl, then $R^{6A}$ is not substituted or unsubstituted $C_1$-$C_5$ alkyl or —$C(O)OR^{19}$, wherein $R^{19}$ is substituted or unsubstituted $C_1$-$C_5$ alkyl.

Embodiment 30. The compound of embodiment 1, wherein if $L^1$ is unsubstituted $C_1$-$C_5$ alkylene and $R^6$ is thiazolyl, then $R^{6A}$ is not substituted or unsubstituted $C_1$-$C_5$ alkyl or —$C(O)OR^{19}$, wherein $R^{19}$ is substituted or unsubstituted $C_1$-$C_5$ alkyl.

Embodiment 31. The compound of embodiment 1, wherein if $L^1$ is unsubstituted $C_1$-$C_5$ alkylene and $R^6$ is $R^{6A}$-substituted 5-membered heteroaryl, then $R^{6A}$ is not substituted or unsubstituted $C_1$-$C_5$ alkyl or —$C(O)OR^{19}$, wherein $R^{19}$ is substituted or unsubstituted $C_1$-$C_5$ alkyl.

Embodiment 32. The compound of embodiment 1, wherein $R^1$ is —Br, —$SR^9$, —$OR^9$, —$NO_2$, —CN, or substituted or unsubstituted $C_1$-$C_{10}$ alkyl.

Embodiment 33. The compound of embodiment 1, wherein $R^1$ is —$SR^9$ and $R^9$ is substituted or unsubstituted $C_1$-$C_{10}$ alkyl.

Embodiment 34. The compound of embodiment 1, wherein $R^1$ is —$SR^9$ and $R^9$ is substituted or unsubstituted $C_1$-$C_5$ alkyl.

Embodiment 35. The compound of embodiment 1, wherein $R^1$ is —$SR^9$ and $R^9$ is unsubstituted $C_1$-$C_5$ alkyl.

Embodiment 36. The compound of embodiment 1, wherein $R^1$ is —$SR^9$ and $R^9$ is methyl.

Embodiment 37. The compound of embodiment 1, wherein $R^1$ is —$OR^9$ and $R^9$ is substituted or unsubstituted $C_2$-$C_{10}$ alkyl.

Embodiment 38. The compound of embodiment 1, wherein $R^1$ is —$OR^9$ and $R^9$ is substituted or unsubstituted $C_2$-$C_5$ alkyl.

Embodiment 39. The compound of embodiment 1, wherein $R^1$ is —$OR^9$ and $R^9$ is unsubstituted $C_2$-$C_5$ alkyl.

Embodiment 40. The compound of embodiment 1, wherein $R^1$ is substituted or unsubstituted $C_1$-$C_5$ alkyl.

Embodiment 41. The compound of embodiment 1, wherein $R^1$ is unsubstituted $C_1$-$C_5$ alkyl.

Embodiment 42. The compound of embodiment 1, wherein $R^1$ is unsubstituted branched $C_1$-$C_5$ alkyl.

Embodiment 43. The compound of embodiment 41, wherein $R^1$ is unsubstituted ethyl.

Embodiment 44. The compound of embodiment 41, wherein $R^1$ is unsubstituted isopropyl.

Embodiment 45. The compound of one of embodiments 1 or 33 to 44, wherein $R^2$ is —Br, —$SR^{11}$, —$OR^{11}$, —$NO_2$, —CN, or substituted or unsubstituted $C_1$-$C_{10}$ alkyl.

Embodiment 46. The compound of one of embodiments 1 or 33 to 44, wherein $R^2$ is —$SR^{11}$ and $R^{11}$ is substituted or unsubstituted $C_1$-$C_{10}$ alkyl.

Embodiment 47. The compound of one of embodiments 1 or 33 to 44, wherein $R^2$ is —$SR^{11}$ and $R^{11}$ is substituted or unsubstituted $C_1$-$C_5$ alkyl.

Embodiment 48. The compound of one of embodiments 1 or 33 to 44, wherein $R^2$ is —$SR^{11}$ and $R^{11}$ is unsubstituted $C_1$-$C_5$ alkyl.

Embodiment 49. The compound of one of embodiments 1 or 33 to 44, wherein $R^2$ is —$SR^{11}$ and $R^{11}$ is methyl.

Embodiment 50. The compound of one of embodiments 1 or 33 to 44, wherein $R^2$ is —$OR^{11}$ and $R^{11}$ is substituted or unsubstituted $C_2$-$C_{10}$ alkyl.

Embodiment 51. The compound of one of embodiments 1 or 33 to 44, wherein $R^2$ is —$OR^{11}$ and $R^{11}$ is substituted or unsubstituted $C_2$-$C_5$ alkyl.

Embodiment 52. The compound of one of embodiments 1 or 33 to 44, wherein $R^2$ is —$OR^{11}$ and $R^{11}$ is unsubstituted $C_2$-$C_5$ alkyl.

Embodiment 53. The compound of one of embodiments 1 or 33 to 44, wherein $R^2$ is substituted or unsubstituted $C_1$-$C_5$ alkyl.

Embodiment 54. The compound of one of embodiments 1 or 33 to 44, wherein $R^2$ is unsubstituted $C_1$-$C_5$ alkyl.

Embodiment 55. The compound of one of embodiments 1 or 33 to 44, wherein $R^2$ is unsubstituted branched $C_1$-$C_5$ alkyl.

Embodiment 56. The compound of one of embodiments 1 or 33 to 44, wherein $R^2$ is unsubstituted ethyl.

Embodiment 57. The compound of one of embodiments 1 or 33 to 44, wherein $R^2$ is unsubstituted isopropyl.

Embodiment 58. The compound of one of embodiments 1 or 33 to 57, wherein $R^3$ is —Br, —$SR^{13}$, —$OR^{13}$, —$NO_2$, —CN, or substituted or unsubstituted $C_1$-$C_{10}$ alkyl.

Embodiment 59. The compound of one of embodiments 1 or 33 to 57, wherein $R^3$ is —$SR^{13}$ and $R^{13}$ is substituted or unsubstituted $C_1$-$C_{10}$ alkyl.

Embodiment 60. The compound of one of embodiments 1 or 33 to 57, wherein $R^3$ is —$SR^{13}$ and $R^{13}$ is substituted or unsubstituted $C_1$-$C_5$ alkyl.

Embodiment 61. The compound of one of embodiments 1 or 33 to 57, wherein $R^3$ is —$SR^{13}$ and $R^{13}$ is unsubstituted $C_1$-$C_5$ alkyl.

Embodiment 62. The compound of one of embodiments 1 or 33 to 57, wherein $R^3$ is —$SR^{13}$ and $R^{13}$ is methyl.

Embodiment 63. The compound of one of embodiments 1 or 33 to 57, wherein $R^3$ is —$OR^{13}$ and $R^{13}$ is substituted or unsubstituted $C_2$-$C_{10}$ alkyl.

Embodiment 64. The compound of one of embodiments 1 or 33 to 57, wherein $R^3$ is —$OR^{13}$ and $R^{13}$ is substituted or unsubstituted $C_2$-$C_5$ alkyl.

Embodiment 65. The compound of one of embodiments 1 or 33 to 57, wherein $R^3$ is —$OR^{13}$ and $R^{13}$ is unsubstituted $C_2$-$C_5$ alkyl.

Embodiment 66. The compound of one of embodiments 1 or 33 to 57, wherein $R^3$ is substituted or unsubstituted $C_1$-$C_5$ alkyl.

Embodiment 67. The compound of one of embodiments 1 or 33 to 57, wherein $R^3$ is unsubstituted $C_1$-$C_5$ alkyl.

Embodiment 68. The compound of one of embodiments 1 or 33 to 57, wherein $R^3$ is unsubstituted branched $C_1$-$C_5$ alkyl.

Embodiment 69. The compound of one of embodiments 1 or 33 to 57, wherein $R^3$ is unsubstituted ethyl.

Embodiment 70. The compound of one of embodiments 1 or 33 to 57, wherein $R^3$ is unsubstituted isopropyl.

Embodiment 71. The compound of one of embodiments 1 or 33 to 70, wherein $R^8$ is —Br, —CN, —$SR^{15}$, —$OR^{15}$, —$NR^{15}R^{16}$, or substituted or unsubstituted $C_1$-$C_{10}$ alkyl.

Embodiment 72. The compound of one of embodiments 1 or 33 to 70, wherein $R^8$ is —$SR^{15}$ and $R^{15}$ is hydrogen or substituted or unsubstituted $C_1$-$C_{10}$ alkyl.

Embodiment 73. The compound of one of embodiments 1 or 33 to 70, wherein $R^8$ is —$SR^{15}$ and $R^{15}$ is substituted or unsubstituted $C_1$-$C_5$ alkyl.

Embodiment 74. The compound of one of embodiments 1 or 33 to 70, wherein $R^8$ is —$SR^{15}$ and $R^{15}$ is unsubstituted $C_1$-$C_5$ alkyl.

Embodiment 75. The compound of one of embodiments 1 or 33 to 70, wherein $R^8$ is —$SR^{15}$ and $R^{15}$ is methyl.

Embodiment 76. The compound of one of embodiments 1 or 33 to 70, wherein $R^8$ is —$SR^{15}$ and $R^{15}$ is ethyl.

Embodiment 77. The compound of one of embodiments 1 or 33 to 70, wherein $R^8$ is —$OR^{15}$ and $R^{15}$ is hydrogen or substituted or unsubstituted $C_2$-$C_{10}$ alkyl.

Embodiment 78. The compound of one of embodiments 1 or 33 to 70, wherein $R^8$ is —$OR^{15}$ and $R^{15}$ is substituted or unsubstituted $C_2$-$C_5$ alkyl.

Embodiment 79. The compound of one of embodiments 1 or 33 to 70, wherein $R^8$ is —$OR^{15}$ and $R^{15}$ is unsubstituted $C_2$-$C_5$ alkyl.

Embodiment 80. The compound of one of embodiments 1 or 33 to 70, wherein $R^8$ is —$OR^{15}$ and $R^{15}$ is hydrogen, methyl, ethyl or isopropyl.

Embodiment 81. The compound of one of embodiments 1 or 33 to 70, wherein $R^8$ is —$NR^{15}R^{16}$ and $R^{15}$ and $R^{16}$ are independently hydrogen, 0 or substituted or unsubstituted $C_2$-$C_{10}$ alkyl.

Embodiment 82. The compound of one of embodiments 1 or 33 to 70, wherein $R^8$ is —$NR^{15}R^{16}$ and $R^{15}$ and $R^{16}$ are independently hydrogen, 0, methyl or ethyl.

Embodiment 83. The compound of one of embodiments 1 or 33 to 70, wherein $R^8$ is substituted or unsubstituted $C_1$-$C_5$ alkyl.

Embodiment 84. The compound of one of embodiments 1 or 33 to 70, wherein $R^8$ is unsubstituted $C_1$-$C_5$ alkyl.

Embodiment 85. The compound of one of embodiments 1 or 33 to 70, wherein $R^8$ is unsubstituted branched $C_1$-$C_5$ alkyl.

Embodiment 86. The compound of one of embodiments 1 or 33 to 70, wherein $R^8$ is unsubstituted ethyl.

Embodiment 87. The compound of one of embodiments 1 or 33 to 70, wherein $R^8$ is unsubstituted isopropyl.

Embodiment 88. The compound of one of embodiments 1 or 33 to 87, wherein $R^4$ is substituted or unsubstituted $C_1$-$C_{10}$ alkyl.

Embodiment 89. The compound of one of embodiments 1 or 33 to 87, wherein $R^4$ is substituted or unsubstituted $C_1$-$C_5$ alkyl.

Embodiment 90. The compound of one of embodiments 1 or 33 to 87, wherein $R^4$ is unsubstituted $C_1$-$C_5$ alkyl.

Embodiment 91. The compound of one of embodiments 1 or 33 to 87, wherein $R^4$ is methyl.

Embodiment 92. The compound of one of embodiments 1 or 33 to 91, wherein $R^5$ is halogen or substituted or unsubstituted $C_1$-$C_{10}$ alkyl.

Embodiment 93. The compound of one of embodiments 1 or 33 to 91, wherein $R^5$ is halogen or unsubstituted $C_1$-$C_5$ alkyl.

Embodiment 94. The compound of one of embodiments 1 or 33 to 92, wherein $R^6$ is $R^{6A}$-substituted heterocycloalkyl, $R^{6A}$-substituted aryl or $R^{6A}$-substituted heteroaryl.

Embodiment 95. The compound of one of embodiments 1 or 33 to 94, wherein $R^6$ is $R^{6A}$-substituted 5-6 membered heterocycloalkyl, $R^{6A}$-substituted $C_5$-$C_6$ aryl or $R^{6A}$-substituted 5 to 6 membered heteroaryl.

Embodiment 96. The compound of one of embodiments 1 or 33 to 95, wherein $R^6$ is $R^{6A}$-substituted phenyl.

Embodiment 97. The compound of one of embodiments 1 or 33 to 95, wherein $R^{6A}$ is —Br, —$SR^{19}$, —$SO_{n6}R^{19}$, —C(O)—$OR^{19}$, —$OR^{19}$, substituted or unsubstituted alkyl or substituted or unsubstituted aryl.

Embodiment 98. The compound of one of embodiments 1 or 33 to 95, wherein $R^{6A}$ is —$SR^{19}$ and $R^{19}$ is substituted or unsubstituted $C_1$-$C_5$ alkyl.

Embodiment 99. The compound of one of embodiments 1 or 33 to 95, wherein $R^{6A}$ is —$SR^{19}$ and $R^{19}$ is methyl or ethyl.

Embodiment 100. The compound of one of embodiments 1 or 33 to 95, wherein $R^{19}$ is substituted $C_1$-$C_5$ alkyl.

Embodiment 101. The compound of one of embodiments 1 or 33 to 98, wherein $R^{19}$ is substituted $C_1$ alkyl.

Embodiment 102. The compound of one of embodiments 1 or 33 to 98, wherein $R^{19}$ is trifluoromethyl.

Embodiment 103. The compound of one of embodiments 1 or 33 to 95, wherein $R^{6A}$ is —$SO_{n6}R^{19}$, $n_6$ is 1 or 2 and $R^{19}$ is substituted or unsubstituted $C_1$-$C_5$ alkyl.

Embodiment 104. The compound of one of embodiments 1 or 33 to 103, wherein $R^{19}$ is unsubstituted $C_1$-$C_5$ alkyl.

Embodiment 105. The compound of one of embodiments 1 or 33 to 103, wherein $R^{19}$ is unsubstituted $C_1$-$C_3$ alkyl.

Embodiment 106. The compound of one of embodiments 1 or 33 to 103, wherein $R^{19}$ is methyl or ethyl.

Embodiment 107. The compound of one of embodiments 1 or 33 to 95, wherein $R^{6A}$ is —C(O)—$OR^{19}$ and $R^{19}$ is hydrogen or substituted or unsubstituted $C_1$-$C_5$ alkyl.

Embodiment 108. The compound of one of embodiments 1 or 33 to 107, wherein $R^{19}$ is hydrogen.

Embodiment 109. The compound of one of embodiments 1 or 33 to 107, wherein $R^{19}$ is unsubstituted $C_1$-$C_5$ alkyl.

Embodiment 110. The compound of one of embodiments 1 or 33 to 107, wherein $R^{19}$ is unsubstituted $C_1$-$C_3$ alkyl.

Embodiment 111. The compound of one of embodiments 1 or 33 to 107, wherein $R^{19}$ is methyl.

Embodiment 112. The compound of one of embodiments 1 or 33 to 107, wherein $R^{19}$ is ethyl.

Embodiment 113. The compound of one of embodiments 1 or 33 to 107, wherein $R^{19}$ is isopropyl.

Embodiment 114. The compound of one of embodiments 1 or 33 to 95, wherein $R^{64}$ is —$OR^{19}$ and $R^{19}$ is trifluoromethyl or substituted or unsubstituted $C_1$-$C_5$ alkyl.

Embodiment 115. The compound of one of embodiments 1 or 33 to 114, wherein $R^{19}$ is trifluoromethyl.

Embodiment 116. The compound of one of embodiments 1 or 33 to 114, wherein $R^{19}$ is unsubstituted $C_1$-$C_5$ alkyl.

Embodiment 117. The compound of one of embodiments 1 or 33 to 114, wherein $R^{19}$ is unsubstituted $C_1$-$C_3$ alkyl.

Embodiment 118. The compound of one of embodiments 1 or 33 to 114, wherein $R^{19}$ is methyl.

Embodiment 119. The compound of one of embodiments 1 or 33 to 114, wherein $R^{19}$ is ethyl.

Embodiment 120. The compound of one of embodiments 1 or 33 to 114, wherein $R^{19}$ is isopropyl.

Embodiment 121. The compound of one of embodiments 1 or 33 to 114, wherein $R^{19}$ is substituted $C_1$-$C_5$ alkyl.

Embodiment 122. The compound of one of embodiments 1 or 33 to 114, wherein $R^{19}$ is substituted ethyl.

Embodiment 123. The compound of one of embodiments 1 or 33 to 95, wherein $R^{64}$ is substituted or unsubstituted $C_1$-$C_{10}$ alkyl.

Embodiment 124. The compound of one of embodiments 1 or 33 to 95, wherein $R^{64}$ is substituted or unsubstituted $C_1$-$C_5$ alkyl.

Embodiment 125. The compound of one of embodiments 1 or 33 to 95, wherein $R^{64}$ is substituted or unsubstituted $C_1$-$C_3$ alkyl.

Embodiment 126. The compound of one of embodiments 1 or 33 to 95, wherein $R^{64}$ is substituted $C_1$-$C_3$ alkyl.

Embodiment 127. The compound of one of embodiments 1 or 33 to 95, wherein $R^{64}$ is hydroxymethyl.

Embodiment 128. The compound of one of embodiments 1 or 33 to 95, wherein $R^6$ is $R^{64}$-substituted furanyl.

Embodiment 129. The compound of one of embodiments 1, 33 to 128, wherein $R^{64}$ is —Br, —$SR^{19}$, —$SO_{n6}R^{19}$, —C(O)—$OR^{19}$, —$OR^{19}$, substituted or unsubstituted alkyl or substituted or unsubstituted aryl.

Embodiment 130. The compound of one of embodiments 1 or 33 to 95, wherein $R^6$ is $R^{64}$-substituted thiophene.

Embodiment 131. The compound of one of embodiments 1 or 33 to 130, wherein $R^{64}$ is substituted or unsubstituted $C_1$-$C_{10}$ alkyl.

Embodiment 132. The compound of one of embodiments 1 or 33 to 130, wherein $R^{64}$ is substituted or unsubstituted $C_1$-$C_5$ alkyl.

Embodiment 133. The compound of one of embodiments 1 or 33 to 130, wherein $R^{64}$ is unsubstituted $C_1$-$C_5$ alkyl.

Embodiment 134. The compound of one of embodiments 1 or 33 to 130, wherein $R^{64}$ is methyl.

Embodiment 135. The compound of one of embodiments 1 or 33 to 95, wherein $R^6$ is $R^{64}$-substituted oxazolyl.

Embodiment 136. The compound of one of embodiments 1 or 33 to 135, wherein $R^{64}$ is trifluoromethyl, —Br, —$SR^{19}$, —$SO_{n6}R^{19}$, —C(O)—$OR^{19}$, —$OR^{19}$, substituted or unsubstituted alkyl or substituted or unsubstituted aryl.

Embodiment 137. The compound of one of embodiments 1 or 33 to 95, wherein $R^6$ is $R^{64}$-substituted pyridyl.

Embodiment 138. The compound of one of embodiments 1, 33 to 137, wherein $R^{64}$ is —Cl, —F. —$CX^f_3$, —$SR^{19}$, —$SO_{n6}R^{19}$, —C(O)—$OR^{19}$, —$OR^{19}$, substituted or unsubstituted alkyl or substituted or unsubstituted aryl.

Embodiment 139. The compound of one of embodiments 1 or 33 to 95, wherein $R^6$ is $R^{64}$-substituted thiazole.

Embodiment 140. The compound of one of embodiments 1 or 33 to 139, wherein $R^{64}$ is —Cl or —$NR^{19}R^2$ Embodiment 141. The compound of one of embodiments 1 or 33 to 139, wherein $R^{64}$ is —$NR^{19}R^{20}$, $R^{19}$ is hydrogen and $R^{20}$ is —OC(O)$CH_3$.

Embodiment 142. The compound of one of embodiments 1 or 33 to 141, wherein $R^7$ is substituted or unsubstituted $C_1$-$C_{10}$ alkyl.

Embodiment 143. The compound of one of embodiments 1 or 33 to 141, wherein $R^7$ is substituted or unsubstituted $C_1$-$C_5$ alkyl.

Embodiment 144. The compound of one of embodiments 1 or 33 to 141, wherein $R^7$ is unsubstituted $C_1$-$C_5$ alkyl.

Embodiment 145. The compound of one of embodiments 1 or 33 to 141, wherein $R^7$ is unsubstituted ethyl.

Embodiment 146. The compound of one of embodiments 1 or 33 to 141, wherein $R^7$ is methyl.

Embodiment 147. The compound of one of embodiments 1 or 33 to 141, wherein $R^7$ is saturated or unsaturated unsubstituted $C_1$-$C_5$ alkyl.

Embodiment 148. The compound of one of embodiments 1 or 33 to 141, wherein $R^7$ is unsaturated unsubstituted $C_1$-$C_5$ alkyl.

Embodiment 149. The compound of one of embodiments 1 or 33 to 141, wherein $R^7$ is unsaturated unsubstituted $C_1$-$C_3$ alkyl.

Embodiment 150. The compound of one of embodiments 1 or 33 to 141, wherein $R^7$ is propenyl.

Embodiment 151. The compound of one of embodiments 1 or 33 to 150, wherein $L^1$ is substituted or unsubstituted $C_1$-$C_{10}$ alkylene.

Embodiment 152. The compound of one of embodiments 1 or 33 to 150, wherein $L^1$ is substituted or unsubstituted $C_1$-$C_5$ alkylene.

Embodiment 153. The compound of one of embodiments 1 or 33 to 150, wherein $L^1$ is unsubstituted $C_1$-$C_5$ alkylene.

Embodiment 154. The compound of one of embodiments 1 or 33 to 150, wherein $L^1$ is unsubstituted $C_1$-$C_3$ alkylene.

Embodiment 155. The compound of one of embodiments 1 or 33 to 150, wherein $L^1$ is methylene or ethylene.

Embodiment 156. A pharmaceutical composition comprising a pharmaceutically acceptable excipient and a compound of one of embodiments 1-155.

Embodiment 157. A method of treating a Hsp70-mediated disease in a patient in need of such treatment, said method comprising administering a therapeutically effective amount of a compound of one of embodiments 1-155.

Embodiment 158. The method of embodiment 157, wherein the disease is cancer, an infectious disease or a neurodegenerative disease.

Embodiment 159. The method of embodiment 158, wherein said cancer is acute T cell leukemia, breast cancer, multiple myeloma, malignant melanoma, ovarian cancer, colorectal adenocarcinoma, endometrial cancer, cervical cancer or bladder cancer.

Embodiment 160. The method of embodiment 158, wherein said neurodegenerative disease is a polyglutamine expansion disorder.

Embodiment 161. The method of embodiment 160, wherein said polyglutamine expansion disorder is Kennedy's disease.

Embodiment 162. The method of embodiment 158, wherein said neurodegenerative disease is a tauopathy.

Embodiment 163. The method of embodiment 162, wherein said tauopathy is Alzheimer's disease.

Embodiment 164. The method of embodiment 158, wherein said infectious disease is Dengue fever.

Embodiment 165. The method of embodiment 158, wherein said infectious disease is a Hepatitis C virus (HCV) disease.

Embodiment 166. The method of embodiment 158, wherein said infectious disease is influenza.

Embodiment 167. A method of inhibiting the activity of Hsp70 in a cell, said method comprising contacting said cell with a compound of one of embodiments 1-155.

What is claimed is:
1. A compound of formula:

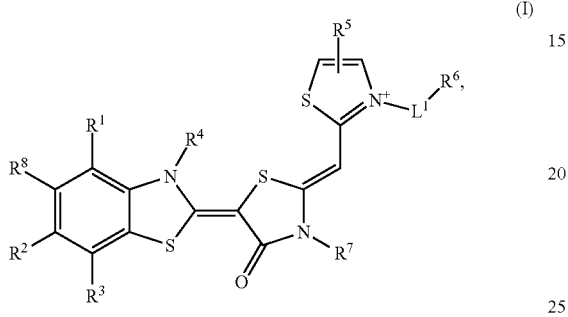

(I)

wherein:
R$^1$ is hydrogen, halogen, —CX$^a_3$, —CN, —SR$^9$, —SO$_2$Cl, —SO$_{n1}$R$^9$, —SO$_{v1}$NR$^9$R$^{10}$, —NHNH$_2$, —ONR$^9$R$^{10}$, —NHC=(O)NHNH$_2$, —NHC=(O)NR$^9$R$^{10}$, —N(O)$_{m1}$, —NR$^9$R$^{10}$, —NH—O—R$^9$, —NHC(O)R$^9$, —C(O)R$^9$, —C(O)—OR$^9$, —C(O)NR$^9$R$^{10}$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein each substituted alkyl, substituted heteroalkyl, substituted cycloalkyl, substituted heterocycloalkyl, substituted aryl, or substituted heteroaryl is substituted with at least one substituent group;

R$^2$ is hydrogen, halogen, —CX$^b_3$, —CN, —SR$^{11}$, —SO$_2$Cl, —SO$_{n2}$R$^{11}$, —SO$_{v2}$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_{m2}$, —NR$^{11}$R$^{12}$, —NH—O—R$^{11}$, —NHC(O)R$^{11}$, —C(O)R$^{11}$, —C(O)—OR$^{11}$, —C(O)NR$^{11}$R$^{12}$, —OR$^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein each substituted alkyl, substituted heteroalkyl, substituted cycloalkyl, substituted heterocycloalkyl, substituted aryl, or substituted heteroaryl is substituted with at least one substituent group;

R$^3$ is hydrogen, halogen, —CX$^c_3$, —CN, —SR$^{13}$, —SO$_2$Cl, —SO$_{n3}$R$^{13}$, —SO$_{v3}$NR$^{13}$R$^{14}$, —NHNH$_2$, —ONR$^{13}$R$^{14}$, —NHC=(O)NHNH$_2$, —NHC=(O)NR$^{13}$R$^{14}$, —N(O)$_{m3}$, —NR$^{13}$R$^{14}$, —NH—O—R$^{13}$, —NHC(O)R$^{13}$, —C(O)R$^{13}$, —C(O)—OR$^{13}$, —C(O)NR$^{13}$R$^{14}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein each substituted alkyl, substituted heteroalkyl, substituted cycloalkyl, substituted heterocycloalkyl, substituted aryl, or substituted heteroaryl is substituted with at least one substituent group;

R$^8$ is hydrogen, halogen, —CX$^d_3$, —CN, —SR$^{15}$, —SO$_2$Cl, —SO$_{n4}$R$^{15}$, —SO$_{v4}$NR$^{15}$R$^{16}$, —NHNH$_2$, —ONR$^{15}$R$^{16}$, —NHC=(O)NHNH$_2$, —NHC=(O)NR$^{15}$R$^{16}$, —N(O)$_{m4}$, —NR$^{15}$R$^{16}$, —NH—O—R$^{15}$, —NHC(O)R$^{15}$, —C(O)R$^{15}$, —C(O)—OR$^{15}$, —C(O)NR$^{15}$R$^{16}$, —OR$^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein each substituted alkyl, substituted heteroalkyl, substituted cycloalkyl, substituted heterocycloalkyl, substituted aryl, or substituted heteroaryl is substituted with at least one substituent group;

R$^4$ is unsubstituted alkyl, unsubstituted heteroalkyl, unsubstituted cycloalkyl, unsubstituted heterocycloalkyl, unsubstituted aryl, or unsubstituted heteroaryl;

R$^5$ is hydrogen, halogen, —CX$^e_3$, —CN, —SR$^{17}$, —SO$_2$Cl, —SO$_{n5}$R$^{17}$, —SO$_{v5}$NR$^{17}$R$^{18}$, —NHNH$_2$, —ONR$^{17}$R$^{18}$, —NHC=(O)NHNH$_2$, —NHC=(O)NR$^{17}$R$^{18}$, —NH—O—R$^{17}$, —NHC(O)R$^{17}$, —C(O)R$^{17}$, —C(O)—OR$^{17}$, —C(O)NR$^{17}$R$^{18}$, —OR$^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein each substituted alkyl, substituted heteroalkyl, substituted cycloalkyl, substituted heterocycloalkyl, substituted aryl, or substituted heteroaryl is substituted with at least one substituent group;

R$^6$ is R$^{6A}$-substituted cycloalkyl, R$^{6A}$-substituted heterocycloalkyl, R$^{6A}$-substituted aryl or R$^{6A}$-substituted heteroaryl;

R$^{6A}$ is independently halogen, —CX$^f_3$, —CN, —SR$^{19}$, —SO$_2$Cl, —SO$_{n6}$R$^{19}$, —SO$_{v6}$NR$^{19}$R$^{20}$, —NHNH$_2$, —ONR$^{19}$R$^{20}$, —NHC=(O)NHNH$_2$, —NHC=(O)NR$^{19}$R$^{20}$, —N(O)$_{m6}$, —NR$^{19}$R$^{20}$, —NH—O—R$^{19}$, —NHC(O)R$^{19}$, —C(O)R$^{19}$, —C(O)—OR$^{19}$, —C(O)NR$^{19}$R$^{20}$, —OR$^{19}$, unsubstituted alkyl, R$^{6B}$-substituted or unsubstituted heteroalkyl, R$^{6B}$-substituted or unsubstituted cycloalkyl, R$^{6B}$-substituted or unsubstituted heterocycloalkyl, R$^{6B}$-substituted or unsubstituted aryl, or R$^{6B}$-substituted or unsubstituted heteroaryl;

R$^{6B}$ is hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl;

R$^7$ is hydrogen, halogen, —CX$^g_3$, —CN, —SR$^{21}$, —SO$_2$Cl, —SO$_{n7}$R$^{21}$, —SO$_{v7}$NR$^{21}$R$^{22}$, —NHNH$_2$, —ONR$^{21}$R$^{22}$, —NHC=(O)NHNH$_2$, —NHC=(O)NR$^{21}$R$^{22}$, —N(O)$_{m7}$, —NR$^{21}$R$^{22}$, —NH—O—R$^{21}$, —NHC(O)R$^{21}$, —C(O)R$^{21}$, —C(O)—OR$^{21}$, —C(O)NR$^{21}$R$^{22}$, —OR$^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein each substituted alkyl, substituted heteroalkyl, substituted cycloalkyl, substituted heterocycloalkyl, substituted aryl, or substituted heteroaryl is substituted with at least one substituent group;

$L^1$ is a bond, —S(O)—, —S(O)$_2$NH—, —NHS(O)$_2$—, —C(O)O—, —OC(O)—, —C(O)—, —C(O)NH—, —NH—, —NHC(O)—, —O—, —S—, $R^{L1}$-substituted or unsubstituted alkylene, $R^{L1}$-substituted or unsubstituted heteroalkylene, $R^{L1}$-substituted or unsubstituted cycloalkylene, $R^{L1}$-substituted or unsubstituted heterocycloalkylene, $R^{L1}$-substituted or unsubstituted arylene, or $R^{L1}$-substituted or unsubstituted heteroarylene;

$R^{L1}$ is hydrogen, halogen, =O, =S, —CF$_3$, —CN, —CC$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl;

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently is hydrogen, halogen, =O, =S, —CF$_3$, —CN, —CCl$_3$, —COOH, —CH$_2$COOH, —COCH$_3$, —CONH$_2$, —OH, —OC(O)CH$_3$, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein each substituted alkyl, substituted heteroalkyl, substituted cycloalkyl, substituted heterocycloalkyl, substituted aryl, or substituted heteroaryl is substituted with at least one substituent group;

$X^a$, $X^b$, $X^c$, $X^d$, $X^e$, $X^f$ and $X^g$ are independently —F, —Cl, —Br, or —I;

$n_1$, $n_2$, $n_3$, $n_4$, $n_5$, $n_6$ and $n_7$ are independently an integer from 0 to 4;

$m_1$, $m_2$, $m_3$, $m_4$, $m_5$, $m_6$ and $m_7$ are independently an integer from 1 to 2; and $v_1$, $v_2$, $v_3$, $v_4$, $v_5$, $v_6$ and $v_7$ are independently an integer from 1 to 2;

wherein if $R^1$, $R^2$, and $R^3$ are independently hydrogen, —Cl, —F, —OCH$_3$, or —CF$_3$, then —L$^1$—R$^6$ is not —CH$_2$pyridyl, -benzyl,—CH$_2$-difluorophenyl, —CH$_2$-cyclopropyl, —CH$_2$-4-(CH$_2$NHC(O)-tbutyl)phenyl, —CH$_2$-5-nitrofuranyl, —CH$_2$CH$_2$-5-nitrofuranyl, —CH$_2$-2-(5-CF$_3$)furanyl, —CH$_2$-fluorophenyl, —CH$_2$-chlorophenyl, —CH$_2$-nitrophenyl, —CH$_2$-cyanophenyl, —CH(CH$_3$)C(O)Ph, —CH$_2$-(methyl)phenyl, —CH$_2$-trifluoromethylphenyl, —CH$_2$-trifluoromethoxyphenyl, —CH$_2$-difluoromethoxyphenyl, —CH$_2$-3-(2-CO$_2$CH$_3$)thienyl, —CH$_2$-3-(2-bromo)thienyl, —CH$_2$-3-isoxazolyl, —CH$_2$-5-isoxazolyl, —CH$_2$-5-(3-phenyl)isoxazolyl, —CH$_2$-3-(2-bromo)pyridyl, —CH$_2$-3-thienyl, —CH$_2$-2-(5-CO$_2$CH$_2$CH$_3$)furanyl, —CH$_2$-4-(2-methyl)thiazolyl, —CH$_2$-2-(5-CO$_2$CH$_3$)furanyl, —CH$_2$-5-(3-methyl)isoxazolyl, or —CH$_2$—CH(CH$_3$)phenyl.

2. The compound of claim 1, wherein if $L^1$ is —CH$_2$— and $R^6$ is phenyl, then $R^{6A}$ is not —F, —CF$_3$, —OCHF$_2$, —NO$_2$, —OCF$_3$, —CH$_3$, —CN, or —Cl.

3. The compound of claim 1, wherein if $L^1$ is —CH$_2$— and $R^6$ is furanyl, then $R^{6A}$ is not —CF$_3$, —NO$_2$, —C(O)OCH$_3$ or —C(O)OCH$_2$CH$_3$.

4. The compound of claim 1, wherein if $L^1$ is —CH$_2$— and $R^6$ is thiophene, then $R^{6A}$ is not —Br, —C(O)OCH$_3$, or —C(O)OCH$_2$CH$_3$.

5. The compound of claim 1, wherein if $L^1$ is —CH$_2$— and $R^6$ is oxazolyl, then $R^{6A}$ is not methyl or phenyl.

6. The compound of claim 1, wherein if $L^1$ is —CH$_2$— and $R^6$ is pyridyl, then $R^{6A}$ is not —Br.

7. The compound of claim 1, wherein if $L^1$ is —CH$_2$— and $R^6$ is thiazolyl, then $R^{6A}$ is not —CH$_3$ or —C(O)OCH$_3$.

8. The compound of claim 1, wherein $R^1$ is —Br, —SR$^9$, —OR$^9$, —NO$_2$, —CN, or substituted or unsubstituted C$_1$-C$_{10}$ alkyl.

9. The compound of claim 1, wherein $R^2$ is —Br, —SR$^{11}$, —OR$^{11}$, —NO$_2$, —CN, or substituted or unsubstituted C$_1$-C$_{10}$ alkyl.

10. The compound of claim 1, wherein $R^3$ is —Br, —SR$^{13}$, —OR$^{13}$, —NO$_2$, —CN, or substituted or unsubstituted C$_1$-C$_{10}$ alkyl.

11. The compound of claim 1, wherein $R^8$ is —Br, —CN, —SR$^{15}$, —OR$^{15}$, —NR$^{15}$R$^{16}$, or substituted or unsubstituted C$_1$-C$_{10}$ alkyl.

12. The compound of claim 1, wherein $R^4$ is substituted or unsubstituted C$_1$-C$_{10}$ alkyl.

13. The compound of claim 1, wherein $R^5$ is halogen or substituted or unsubstituted C$_1$-C$_{10}$ alkyl.

14. The compound of claim 1, wherein $R^6$ is $R^{6A}$-substituted heterocycloalkyl, $R^{6A}$-substituted aryl or $R^{6A}$-substituted heteroaryl.

15. The compound of claim 1, wherein $R^6$ is $R^{6A}$-substituted phenyl.

16. The compound of claim 15, wherein $R^{6A}$ is —Br, —SR$^{19}$, —SO$_{n6}$R$^{19}$, —C(O)—OR$^{19}$, —OR$^{19}$, unsubstituted alkyl or substituted or unsubstituted aryl.

17. The compound of claim 16, wherein $R^{19}$ is substituted C$_1$ alkyl.

18. The compound of claim 16, wherein $R^{19}$ is trifluoromethyl.

19. The compound of claim 16, wherein $R^{19}$ is methyl or ethyl.

20. The compound of claim 16, wherein $R^{19}$ is hydrogen.

21. The compound of claim 1, wherein $R^6$ is $R^{6A}$-substituted furanyl.

22. The compound of claim 21, wherein $R^{6A}$ is —Br, —SR$^{19}$, —SO$_{n6}$R$^{19}$, —C(O)—OR$^{19}$, —OR$^{19}$, unsubstituted alkyl or substituted or unsubstituted aryl.

23. The compound of claim 1, wherein $R^6$ is $R^{6A}$-substituted oxazolyl.

24. The compound of claim 23, wherein $R^{6A}$ is trifluoromethyl, —Br, —SR$^{19}$, —SO$_{n6}$R$^{19}$, —C(O)—OR$^{19}$, —OR$^{19}$, unsubstituted alkyl or substituted or unsubstituted aryl.

25. The compound of claim 1, wherein $R^6$ is $R^{6A}$-substituted pyridyl.

26. The compound of claim 25, wherein $R^{6A}$ is —Cl, —F. —CX$^f_3$, —SR$^{19}$, —SO$_{n6}$R$^{19}$, —C(O)—OR$^{19}$, —OR$^{19}$, unsubstituted alkyl or substituted or unsubstituted aryl.

27. The compound of claim 1, wherein $R^6$ is $R^{6A}$-substituted thiazole.

28. The compound of claim 27, wherein $R^{6A}$ is —Cl or —NR$^{19}$R$^{20}$.

29. The compound of claim 1, wherein $R^7$ is substituted or unsubstituted C$_1$-C$_5$ alkyl.

30. The compound of claim 1, wherein $L^1$ is substituted or unsubstituted C$_1$-C$_{10}$ alkylene.

31. The compound of claim 1, wherein $L^1$ is methylene or ethylene.

32. A pharmaceutical composition comprising a pharmaceutically acceptable excipient and a compound of claim 1.

33. A method of treating a Hsp70-mediated disease in a patient in need of such treatment, said method comprising administering a therapeutically effective amount of a compound of claim 1, wherein the Hsp70-mediated disease is cancer, an infectious disease or a neurodegenerative disease.

34. The method of claim 33, wherein said cancer is acute T-cell leukemia, breast cancer, multiple myeloma, malignant melanoma, ovarian cancer, colorectal adenocarcinoma, endometrial cancer, cervical cancer or bladder cancer.

35. The method of claim 33, wherein said neurodegenerative disease is Kennedy's disease or Alzheimer's disease.

36. The method of claim 33, wherein said infectious disease is Dengue fever, a Hepatitis C virus (HCV) disease, or influenza.

\* \* \* \* \*